(12) United States Patent
Yokota et al.

(10) Patent No.: US 7,774,852 B2
(45) Date of Patent: Aug. 10, 2010

(54) HEALTH CARE SYSTEM, KEY MANAGEMENT SERVER AND METHOD FOR MANAGING KEY, AND ENCRYPTING DEVICE AND METHOD FOR ENCRYPTING VITAL SIGN DATA

(75) Inventors: Kaoru Yokota, Hyogo (JP); Masao Nonaka, Osaka (JP); Yuichi Futa, Osaka (JP); Natsume Matsuzaki, Osaka (JP); Shunji Harada, Osaka (JP)

(73) Assignee: Panasonic Corporation, Osaka (JP)

( * ) Notice: Subject to any disclaimer, the term of this patent is extended or adjusted under 35 U.S.C. 154(b) by 75 days.

(21) Appl. No.: 12/249,185

(22) Filed: Oct. 10, 2008

(65) Prior Publication Data

US 2009/0099967 A1 Apr. 16, 2009

(51) Int. Cl.
G06F 7/04 (2006.01)
G06F 17/30 (2006.01)
G06F 19/00 (2006.01)
G06Q 50/00 (2006.01)
(52) U.S. Cl. ............... 726/27; 705/2; 705/3; 713/189; 713/193; 726/28; 726/29
(58) Field of Classification Search .............. 713/189, 713/193; 705/2–3; 726/27–29
See application file for complete search history.

(56) References Cited

U.S. PATENT DOCUMENTS 6,302,844 B1 * 10/2001 Walker et al. .......... 600/300
7,609,145 B2 * 10/2009 Martis et al. .......... 340/5.1
7,683,759 B2 * 3/2010 Martis et al. .......... 340/5.83

2001/0027384 A1 * 10/2001 Schulze et al. .......... 702/188
2002/0010596 A1 * 1/2002 Matory .......... 705/2
2003/0069752 A1 * 4/2003 LeDain et al. .......... 705/2
2003/0216940 A1 * 11/2003 Sobel .......... 705/2
2004/0172290 A1 * 9/2004 Leven .......... 705/2

(Continued)

FOREIGN PATENT DOCUMENTS

JP 2005-245833 9/2005

(Continued)

OTHER PUBLICATIONS

Ascii Media Works, Mar. 8, 2007, "*Tanita Starts Healthcare Service "Monitoring Your Health" Using Network*", retrieved on Oct. 11, 2007 from <http://ascii24.com/news/i/serv/article/2007/03/08/667789-000.html>.

*Primary Examiner*—Benjamin E Lanier
(74) *Attorney, Agent, or Firm*—Wenderoth, Lind & Ponack, L.L.P.

(57) ABSTRACT

Provided is a health care system including a key management server that receives from a server a request for a decryption key, with first identification information identifying a measuring apparatus, second identification information identifying vital sign data, and third identification information identifying the server. The key management server generates the decryption key using the first identification information, and stores fourth identification information identifying a server predetermined as a destination of the decryption key, and fifth identification information indicating the category of the vital sign data in correspondence with the fourth identification information. The key management server transmits the decryption key to the server, when the received third identification information matches the fourth identification information, and the received second identification information matches the fifth identification information.

16 Claims, 35 Drawing Sheets

U.S. PATENT DOCUMENTS

| | | | |
|---|---|---|---|
| 2005/0182655 A1* | 8/2005 | Merzlak et al. | 705/2 |
| 2008/0004904 A1* | 1/2008 | Tran | 705/2 |
| 2008/0021730 A1* | 1/2008 | Holla et al. | 705/2 |
| 2008/0021741 A1* | 1/2008 | Holla et al. | 705/3 |
| 2008/0021834 A1* | 1/2008 | Holla et al. | 705/51 |
| 2008/0077435 A1* | 3/2008 | Muradia | 705/2 |
| 2008/0287748 A1* | 11/2008 | Sapounas et al. | 600/300 |
| 2010/0082988 A1* | 4/2010 | Huebner et al. | 713/171 |

FOREIGN PATENT DOCUMENTS

JP      2007-229116      9/2007

* cited by examiner

FIG. 6

22 — Measuring-apparatus information

| Part number | Model ID | Data category | Transmission necessity |
|---|---|---|---|
| KC-289B | 12345678 | 001 | 1 |
| | | 002 | 1 |
| | | 005 | 0 |

FIG. 8

Connected apparatus information — 23

| Measuring-apparatus-card ID | Model ID | Data category | Accumulation necessity |
|---|---|---|---|
| 186512 | 12345678 | 001 | 1 |
| | | 002 | 1 |
| | | 007 | 0 |
| 392138 | 2468912 | 004 | 1 |
| 912356 | 8642013 | 006 | 0 |

FIG. 10

Service information 25

| Use service ID | Necessary data category | Data obtainment measuring-apparatus-card ID | Data obtainment model ID |
|---|---|---|---|
| 0002 | 001 | 186512 | 12345678 |
|  | 004 | 392138 | 24689912 |
| 0148 | 002 | 186512 | 12345678 |

FIG. 24

Measuring-apparatus information ~72

| Part number | Model ID | Data category | Transmission necessity |
|---|---|---|---|
| KC-289B | 12345678 | 001 | 1 |
| | | 002 | 0 |
| | | 005 | 0 |

Connected apparatus information

| Measuring-apparatus -card ID | Model ID | Accumulation necessity |
|---|---|---|
| 186512 | 12345678 | 1 |
| 392138 | 2468912 | 1 |
| 912356 | 8642013 | 0 |

HEALTH CARE SYSTEM, KEY MANAGEMENT SERVER AND METHOD FOR MANAGING KEY, AND ENCRYPTING DEVICE AND METHOD FOR ENCRYPTING VITAL SIGN DATA

BACKGROUND OF THE INVENTION (1) Field of the Invention

The present invention relates to a health care system that can protect confidentiality of health information of a user, such as a body weight and a blood pressure, when the health information is obtained from the user and received via a network, and a health care service including health advice is provided back to the user based on the health information.

(2) Description of the Related Art

In recent years, people have been increasingly concerned about health, and various measuring apparatuses have been sold and have become widespread. Such measuring apparatuses can be easily used for obtaining health information, such as a body weight, a blood pressure, and body composition in households. Furthermore, new health care services have emerged that perform health management instead of a user and provide feedback on health advice to the user (for example, see Non-patent reference 1: Ascii Media Works. (Mar. 8, 2007). "Tanita, nettowaaku wo riyoushita herusu kea saabisu 'monitaringu yua herusu' wo kaishi (Tanita launches healthcare service "Monitoring Your Health" using network) ". Retrieved on Oct. 11, 2007 from <http://ascii24.com/news/i/serv/article/2007/03/08/667,789-000. html>.

In such health care services, various measuring apparatuses transmit the obtained various health information to devices in a household, such as a personal computer (PC) and a special purpose terminal. Then, such devices in a household uniformly manage the transmitted various health information through accumulation of data. Furthermore, the devices transmit various health information to servers via networks on a regular basis. Then, the servers provide health care services that perform health management instead of a user and provide feedback on health advice to the user.

On the other hand, health information of a user is personal information to the user. Thus, when health information of a user is transmitted via wireless communication or via the Internet, measures for preventing third persons from tapping and leaking information need to be taken.

In general, in order to protect user's health information to be transmitted through a communication path, data is encrypted. In a system where devices in a household temporarily collect data of health information that has been obtained by various measuring apparatuses and transmit the collected data to a server via a network, each of the measuring apparatuses and the server share a key and each of the measuring apparatuses encrypts the obtained data using the key. The encrypted data is transmitted to the server through each of the devices in a household. Then, the data is decrypted by the server using the shared key. Since the data is decrypted thus never converted into plain text during the transmission, health information may not be disclosed through tapping and leaking of information.

However, conventionally, when the user use several health care services, the measuring apparatuses have a problem of increased processing load for encrypting data. For example, assume that the user uses 3 health services, and the system needs to transmit blood pressure information of the user to 3 different servers. Thus, a blood pressure meter needs to encrypt the obtained blood pressure data using respective keys for each of the servers. In other words, the blood pressure meter needs to encrypt data 3 times per measurement of a blood pressure. In other words, when the user uses N number of services that respectively need to transmit blood pressure information, the blood pressure meter needs to encrypt the information N number of times.

As described above, there is a problem that the more the number of services increases, the more an amount of processing increases in a measuring apparatus. In general, the measuring apparatuses are portable devices driven by batteries. In order to extend the battery life as long as possible, the amount of processing needs to be reduced as much as possible. Thus, the number of processing for encrypting a large amount of data needs to be reduced as much as possible. In other words, when manufactured, the measuring apparatuses may not support increased number of processing for encrypting data, along with the increased number of services.

The present invention has been conceived for solving such problems, and has an object of providing a health care system and others that can suppress an amount of processing for encrypting data, regardless of the number of services to be used by a user.

SUMMARY OF THE INVENTION

In order to solve the aforementioned problems, a health care system according to one aspect of the present invention includes a key management server connected to a server. A measuring apparatus encrypts using the encryption key the vital sign data obtained through measurement, and transmits to the server the encrypted vital sign data. The key management server receives, from the server, a request for a decryption key corresponding to the encryption key, with first identification information identifying the measuring apparatus, second identification information identifying the vital sign data, and third identification information identifying the server. The key management server generates the decryption key using the first identification information, and stores fourth identification information identifying a server predetermined as a destination of the decryption key, and fifth identification information indicating the category of the vital sign data in correspondence with the fourth identification information. The key management server transmits the decryption key to the server, when the received third identification information matches the stored fourth identification information, and the received second identification information matches the stored fifth identification information.

FURTHER INFORMATION ABOUT TECHNICAL BACKGROUND TO THIS APPLICATION

The disclosures of Japanese Patent Application No. 2007-266742 filed on Oct. 12, 2007 and Japanese Patent Application No. 2008-220207 filed on Aug. 28, 2008 each including specification, drawings and claims are incorporated herein by reference in its entirety.

BRIEF DESCRIPTION OF THE DRAWINGS

These and other objects, advantages and features of the invention will become apparent from the following description thereof taken in conjunction with the accompanying drawings that illustrate a specific embodiment of the invention. In the Drawings:

FIG. 6 shows an example of measuring apparatus information according to the first to third embodiments;

FIG. 8 shows an example of connected apparatus information according to the first to third embodiments;

FIG. 10 shows an example of service information according to the first and third embodiments;

FIG. 24 shows an example of measuring apparatus information according to the second embodiment;

FIG. 25 shows an example of connected apparatus information according to the second embodiment;

DESCRIPTION OF THE PREFERRED EMBODIMENTS

Figure 1:
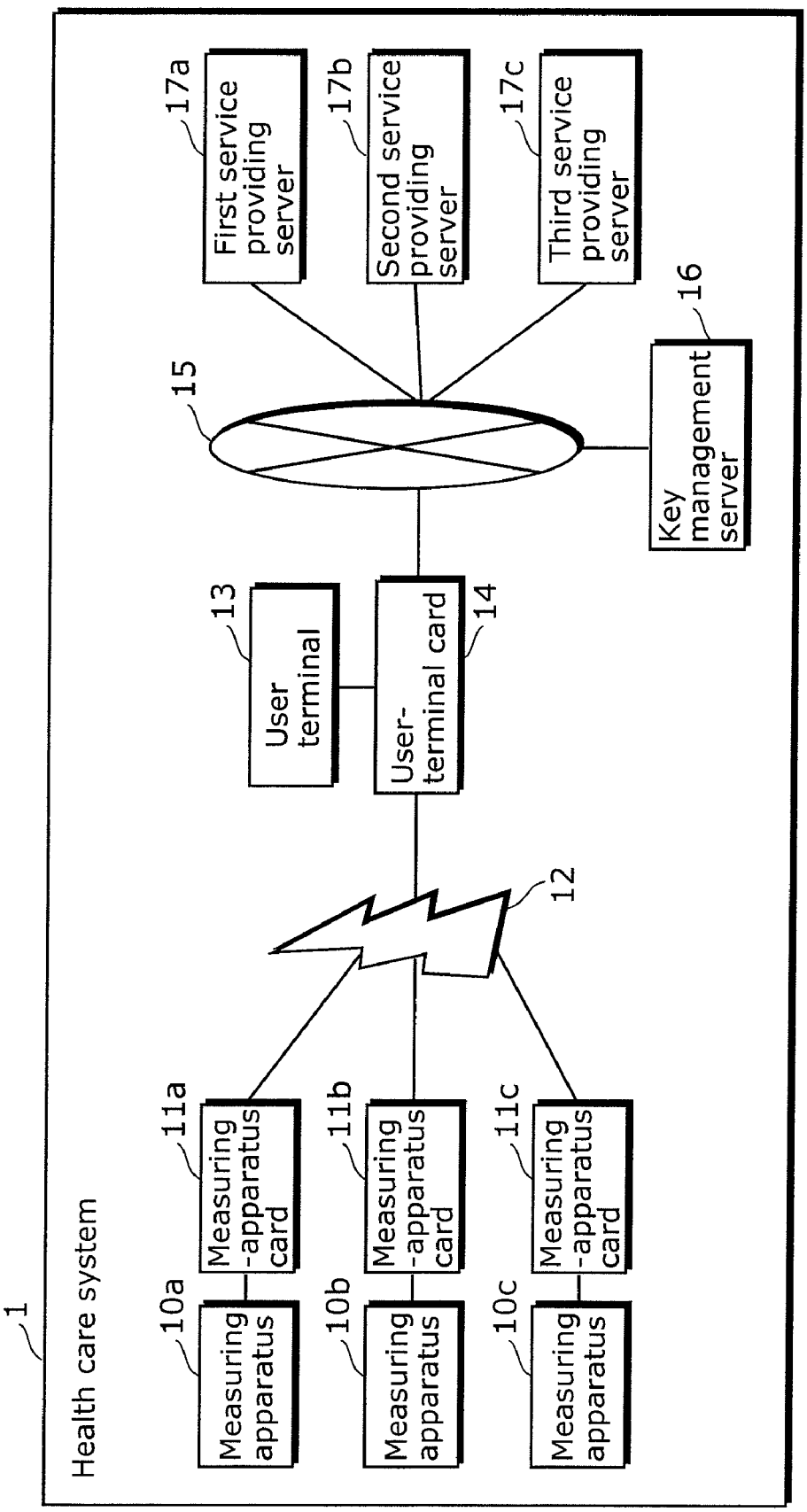
FIG. 1 illustrates a block diagram of an entire configuration of the health care system according to the first to third embodiments.

The health care system according to a first aspect of the present invention includes: a measuring apparatus that obtains vital sign data through measurement and encrypts the obtained vital sign data; a server that obtains the encrypted vital sign data from the measuring apparatus and provides a service related to health; and a key management server that provides a decryption key for decrypting the encrypted vital sign data to the server, wherein the measuring apparatus includes: a measuring unit configured to obtain the vital sign data of a user of the measuring apparatus through measurement of the user of the measuring apparatus; a first storing unit configured to store first identification information identifying the measuring apparatus; a first key generating unit configured to generate an encryption key using the first identification information; an encrypting unit configured to encrypt the obtained vital sign data using the encryption key to generate the encrypted vital sign data; and a first communicating unit configured to transmit, to the server, the first identification information, second identification information, and the encrypted vital sign data, the second identification information identifying a category of the vital sign data, the server includes: a second storing unit configured to store the first identification information, the second identification information, and the encrypted vital sign data transmitted by the first communicating unit; a third storing unit configured to store third identification information identifying the server; and a second communicating unit configured to transmit, to the key management server, a request for transmitting to the server a decryption key corresponding to the encryption key, together with the first identification information, the second identification information, and the third identification information, and the key management server includes: a second key generating unit configured to generate the decryption key corresponding to the encryption key using the first identification information; a fourth storing unit configured to store fourth identification information identifying a server predetermined as a destination of the decryption key, and fifth identification information indicating the category of the vital sign data in correspondence with the fourth identification information; and a control unit configured to transmit the decryption key to the server, upon receipt of the request for transmitting the decryption key from the server, together with the first identification information, the second identification information, and the third identification information, when the received third identification information matches the stored fourth identification information and the received second identification information matches the fifth identification information stored in the fourth storing unit in correspondence with the matched fourth identification information, wherein the server decrypts the encrypted vital sign data using the decryption key.

With this configuration, a key management server generates a decryption key for decrypting encrypted vital sign data stored in a server, and determines the server that transmits the generated decryption key. Thus, when a measuring apparatus encrypts the obtained vital sign data using a predetermined encryption key, there is no need to change a category of the encryption key for use in encrypting the vital sign data, depending on a service provided by a server where the vital sign data is to be transmitted. In other words, regardless of a server to which the vital sign data is transmitted, as long as the measuring apparatus encrypts the data using a shared encryption key and transmits the encrypted data, the key management server determines a server that transmits the decryption key. Thus, only the server selected by the key management server can obtain the decryption key and decrypt the encrypted vital sign data. As a result, the health care system can eliminate encryption processing for encrypting vital sign data using different encryption keys in a measuring apparatus according to a category of each server that provides a service.

Furthermore, the key management server includes fourth storing unit in which fourth identification information identifying a destination of the decryption key is stored, and fifth identification information indicating the category of the vital sign data is stored in correspondence with the fourth identification information, the vital sign data being managed by the server. Then, the key management server transmits the decryption key to the server, upon receipt of the request for transmitting the decryption key from the server, together with the first identification information, the second identification information, and the third identification information, when the received third identification information matches the stored fourth identification information and the received second identification information matches the fifth identification information stored in the fourth storing unit in correspondence with the matched fourth identification information. Thereby, since the key management server has only to store a table indicating a correspondence between the fourth identification information and the fifth identification information in the fourth storing unit, the number of tables that the key management server holds can be reduced.

Furthermore, the health care system according to a second aspect of the present invention includes: a measuring apparatus that obtains vital sign data through measurement and encrypts the obtained vital sign data; a server that obtains the encrypted vital sign data from the measuring apparatus and provides a service related to health; and a key management server that provides a decryption key for decrypting the encrypted vital sign data to the server, wherein the measuring apparatus includes: a measuring unit configured to obtain the vital sign data of a user of the measuring apparatus through measurement of the user of the measuring apparatus; a first storing unit configured to store first identification information identifying the measuring apparatus; a first key generating unit configured to generate an encryption key using the first identification information; an encrypting unit configured to encrypt the obtained vital sign data using the encryption key to generate the encrypted vital sign data; and a first communicating unit configured to transmit, to the server, the first identification information and the encrypted vital sign data, the server includes: a second storing unit configured to store the first identification information and the encrypted vital sign data transmitted by the first communicating unit; a third storing unit configured to store second identification information identifying the server; and a second communicating unit configured to transmit, to the key management server, a request for transmitting to the server the decryption key corresponding to the encryption key, together with the first identification information and the second identification information, and the key management server includes: a fourth storing unit in which a category of the vital sign data obtained by the measuring apparatus is stored in correspondence with the first identification information; a fifth storing unit configured to store a category of the vital sign data managed by the server in correspondence with the second identification information; a second key generating unit configured to generate the decryption key corresponding to the encryption key using the first identification information; and a control unit configured to transmit the decryption key to the server, upon receipt of, from the server, the request for transmitting the decryption key to the server, together with the first identification information and the second identification information, when the category of vital sign data that is stored in the fourth storing unit and corresponds to the received first identification information matches the category of vital sign data that is stored in the fifth storing unit and corresponds to the received second identification information, wherein the server decrypts the encrypted vital sign data using the decryption key.

With this configuration, a key management server generates a decryption key for decrypting encrypted vital sign data stored in a server, and determines the server that transmits the generated decryption key. Thus, when a measuring apparatus encrypts the obtained vital sign data using a predetermined encryption key, there is no need to change a category of the encryption key for use in encrypting the vital sign data, depending on a service provided by a server where the vital sign data is to be transmitted. In other words, regardless of a server to which the vital sign data is transmitted, as long as the measuring apparatus encrypts the data using a shared encryption key and transmits the encrypted data, the key management server determines a server that transmits the decryption key. Thus, only the server selected by the key management server can obtain the decryption key and decrypt the encrypted vital sign data. As a result, the health care system can eliminate encryption processing for encrypting vital sign data using different encryption keys in a measuring apparatus according to a category of each server that provides a service.

Furthermore, the key management server includes: a fourth storing unit in which a category of the vital sign data obtained by the measuring apparatus is stored in correspondence with the first identification information identifying the measuring apparatus; and a fifth storing unit in which a category of the vital sign data managed by the server is stored in correspondence with the second identification information identifying the server. Then, the key management server transmits the decryption key to the server, upon receipt of, from the server, the request for transmitting the decryption key to the server, together with the first identification information and the second identification information, when the category of vital sign data that is stored in the fourth storing unit and corresponds to the received first identification information matches the category of vital sign data that is stored in the fifth storing unit and corresponds to the received second identification information.

Since the key management server can reduce the data categories received from the server to two categories, the first identification information and the second identification information, the processing amount for the judgment on a category can be reduced.

Furthermore, the health care system according to the first and second aspects of the present invention may include an encrypting device including the first key generating unit, the encrypting unit, and the first communicating unit.

According to the aspects of the present invention, the encryption device attached to the measuring apparatus includes the first key generating unit and the encrypting unit. Thus, without substantially adding any constituent elements unnecessary for obtaining data through measurement to the measuring apparatus, the encryption device can generate a predetermined encryption key, generate the encrypted vital sign data using the predetermined encryption key, and transmit the generated vital sign data. Thereby, the configuration of the measuring apparatus can be simplified and the user can be provided with a service related to health.

Furthermore, according to the health care system of the first and second aspects of the present invention, the encrypting device may be a memory card attached to the measuring apparatus.

Furthermore, according to the health care system of the first and second aspects of the present invention, the measuring apparatus may include a first master key holding unit configured to hold a first master key, the first key generating unit may be configured to generate the encryption key using the first identification information and the first master key, the key management server may include a second master key holding unit configured to hold a second master key identical to the first master key, and the second key generating unit may be configured to generate the decryption key corresponding to the encryption key, using the first identification information and the second master key.

According to the aspects of the present invention, the measuring apparatus and the key management server generates the predetermined encryption key and the decryption key corresponding to the encryption key using a shared master key. When the measuring apparatus passes the first identification information identifying the measuring apparatus to the server and the server passes the first identification information to the key management server, the key management server can generate the decryption key corresponding to the encryption key, without transmitting the master key itself through any communication path. Thereby, the health care system can ensure confidentiality of a decryption key.

Furthermore, according to the health care system of the first and second aspects of the present invention, the measuring apparatus may include an encrypting device, the encrypting device may include the first key generating unit, the encrypting unit, the first master key holding unit, and the first communicating unit, and the first key generating unit may be configured to generate the encryption key using the first identification information and the master key.

According to the aspects of the present invention, the encryption device attached to the measuring apparatus includes the first key generating unit, the encrypting unit, and the master key holding unit. Thus, without substantially adding any constituent elements unnecessary for obtaining data through measurement to the measuring apparatus, the encryption device can generate a predetermined encryption key, generate the encrypted vital sign data using the predetermined encryption key, and transmit the generated vital sign data. Thereby, the configuration of the measuring apparatus can be simplified and the user can be provided with a service related to health.

Furthermore, according to the health care system of the first and second aspects of the present invention, the encrypting device may be a memory card attached to the measuring apparatus.

Furthermore, the health care system according to a third aspect of the present invention, the first key generating unit may be configured to generate the encryption key using the first identification information as a public key, the key management server may include a master information holding unit configured to hold master information for generating the decryption key, and the second key generating unit may be configured to generate the decryption key as a secret key corresponding to the public key, using the received first identification information and the held master information.

According to the aspect of the present invention, the measuring apparatus generates, as a public key, the encryption key using the first identification information identifying the measuring apparatus. There is no need to store a master key in the measuring apparatus by encrypting the vital sign data using the generated public key. Thus, the health care system can prevent confidentiality of vital sign data from being impaired through analysis on the measuring apparatus itself and disclosure of a master key.

Furthermore, the measuring apparatus generates, as a public key, the encryption key using the first identification information identifying the measuring apparatus. Thus, as long as the key management server holds master information for generating the decryption key, even when the first identification information is disclosed outside, the encrypted vital sign data can not be decrypted. In other words, the health care system can ensure confidentiality of the vital sign data.

Furthermore, the key management server according to the first aspect of the present includes: a communicating unit configured to receive, from a server, a request for transmitting a decryption key corresponding to an encryption key to the server, together with first identification information identifying a measuring apparatus that obtains vital sign data through measurement, second identification information identifying the vital sign data, and third identification information identifying the server, the communicating unit being connected to the server (i) that receives, from the measuring apparatus, the vital sign data encrypted by the measuring apparatus using the encryption key, and (ii) that provides a service related to health; a key generating unit configured to generate the decryption key using the first identification information; a storing unit in which fourth identification information identifying a destination of the decryption key is stored, and fifth identification information indicating the category of the vital sign data is stored in correspondence with the fourth identification information, the vital sign data being managed by the server; and a control unit configured to transmit the decryption key to the server, when the received third identification information matches the stored fourth identification information, and the received second identification information matches the stored fifth identification information.

With this configuration, a key management server generates a decryption key for decrypting encrypted vital sign data stored in a server, and determines the server that transmits the generated decryption key. Thus, when a measuring apparatus encrypts the obtained vital sign data using a predetermined encryption key, there is no need to change a category of the encryption key for use in encrypting the vital sign data, depending on a service provided by a server where the vital sign data is to be transmitted. In other words, regardless of a server to which the vital sign data is transmitted, as long as the measuring apparatus encrypts the data using a shared encryption key and transmits the encrypted data, the key management server determines a server that transmits the decryption key. Thus, only the server selected by the key management server can obtain the decryption key and decrypt the encrypted vital sign data. As a result, the health care system can eliminate encryption processing for encrypting vital sign data using different encryption keys in a measuring apparatus according to a category of each server that provides a service.

The key management server includes a fourth storing unit in which fourth identification information identifying a destination of the decryption key is stored, and fifth identification information indicating the category of the vital sign data is stored in correspondence with the fourth identification information, the vital sign data being managed by the server. Then, the key management server transmits the decryption key to the server, upon receipt of the request for transmitting the decryption key to the server, together with the first identification information identifying the measuring apparatus, the second identification information identifying the category of the vital sign data, and the third identification information identifying the server, when the received third identification information matches the stored fourth identification information and the received second identification information matches the fifth identification information stored in the fourth storing unit in correspondence with the matched fourth identification information. Thereby, since the key management server has only to store a table indicating a correspondence between the fourth identification information and the fifth identification information, the number of tables that the key management server holds can be reduced.

Furthermore, the key management server according to the second aspect of the present invention is connected to a server, the server receiving, from a measuring apparatus, vital sign data encrypted by the measuring apparatus using an encryption key, and providing a service related to health, the measuring apparatus obtaining the vital sign data of a user of the measuring apparatus through measurement of the user of the measuring apparatus, encrypting the obtained vital sign data using the encryption key, and transmitting to the server the encrypted vital sign data, and the key management server includes: a communicating unit configured to receive, from the server, a request for transmitting to the server a decryption key corresponding to the encryption key, together with first identification information, second identification information, and third identification information, the first identification information identifying the measuring apparatus, the second identification information identifying the vital sign data, and the third identification information identifying the server; a key generating unit configured to generate the decryption key using the first identification information; a storing unit configured to store fourth identification information identifying a server predetermined as a destination of the decryption key, and fifth identification information indicating the category of the vital sign data in correspondence with the fourth identification information; and a control unit configured to transmit the decryption key to the server, when the received third identification information matches the stored fourth identification information, and the received second identification information matches the stored fifth identification information With this configuration, a key management server generates a decryption key for decrypting encrypted vital sign data stored in a server, and determines the server that transmits the generated decryption key. Thus, when a measuring apparatus encrypts the obtained vital sign data using a predetermined encryption key, there is no need to change a category of the encryption key for use in encrypting the vital sign data, depending on a service provided by a server where the vital sign data is to be transmitted. In other words, regardless of a server to which the vital sign data is transmitted, as long as the measuring apparatus encrypts the data using a shared encryption key and transmits the encrypted data, the key management server determines a server that transmits the decryption key. Thus, only the server selected by the key management server can obtain the decryption key and decrypt the encrypted vital sign data. As a result, the health care system can eliminate encryption processing for encrypting vital sign data using different encryption keys in a measuring apparatus according to a category of each server that provides a service.

Furthermore, the key management server includes: a fourth storing unit in which a category of the vital sign data obtained by the measuring apparatus is stored in correspondence with the first identification information identifying the measuring apparatus; and a fifth storing unit in which a category of the vital sign data managed by the server is stored in correspondence with the second identification information identifying the server. Then, the key management server transmits the decryption key to the server, upon receipt of, from the server, the request for transmitting the decryption key to the server, together with the first identification information and the second identification information, when the category of vital sign data corresponding to the received first identification information matches the category of vital sign data corresponding to the received second identification information. Since the key management server can reduce the data categories received from the server to two categories, the first identification information and the second identification information, the processing amount for the judgment on a category can be reduced.

Furthermore, the encrypting device according to the first aspect of the present invention is capable of being attached to a measuring apparatus, the measuring apparatus obtaining vital sign data of a user of the measuring apparatus through measurement of the user of the measuring apparatus and transmitting the vital sign data to a server, the server transmitting a service related to health, and the encrypting device includes: an interface unit configured to receive from the measuring apparatus the vital sign data and identification information identifying the measuring apparatus; a first storing unit configured to store the vital sign data received by the interface unit; a second storing unit configured to store the identification information received by the interface unit; a master key holding unit configured to hold a master key; a key generating unit configured to generate an encryption key using the identification information and the master key; an encrypting unit configured to encrypt the vital sign data using the generated encryption key; and a communicating unit configured to transmit the encrypted vital sign data to the server.

According to the aspect of the present invention, the encryption device attached to the measuring apparatus includes the key generating unit, the encrypting unit, and the master key holding unit. Thus, without substantially adding any constituent elements unnecessary for obtaining data through measurement to the measuring apparatus, the encryption device can generate a predetermined encryption key, generate the encrypted vital sign data using the predetermined encryption key, and transmit the generated vital sign data. Thereby, the configuration of the measuring apparatus can be simplified and the user can be provided with a service related to health.

Furthermore, the encrypting device according to the first aspect of the present invention may be a memory card attached to the measuring apparatus.

According to the aspect of the present invention, the encrypting device may be a memory card attached to the measuring apparatus.

Here, the above-described aspects may be implemented, for example, not only as an apparatus, but also as an integrated circuit including a processing unit included in such an apparatus, as a method having such a processing unit of the apparatus as steps, and as a program causing a computer to execute such steps. Such a program may also be distributed by recording it onto a recording medium, such as a CD-ROM, and via a communication medium, such as the Internet.

The following describes embodiments of the present invention with reference to drawings.

First Embodiment

<Configuration of Health Care System 1>

FIG. 1 illustrates a block diagram of an entire configuration of a health care system 1 according to a first embodiment of the present invention.

The health care system 1 includes: measuring apparatuses 10a, 10b, and 10c; measuring-apparatus cards 11a, 11b, and 11c respectively attached to the measuring apparatuses 10a, 10b, and 10c; a user terminal 13; a user-terminal card 14 attached to the user terminal 13; a first service providing server 17a; a second service providing server 17b; a third service providing server 17c; and a key management server 16.

The measuring apparatuses 10a, 10b, and 10c are examples of measuring apparatuses for obtaining health information, and the measuring-apparatus cards 11a, 11b, and 11c are examples of encrypting devices for encrypting the health information.

The user terminal 13 and the user-terminal card 14 transfer the health information received and encrypted by the measuring-apparatus cards 11a, 11b, and 11c to the first service providing server 17a, the second service providing server 17b, and the third service providing server 17c.

The first service providing server 17a, the second service providing server 17b, and the third service providing server 17c are examples of servers, and provide a service regarding health by decrypting the health information encrypted.

The key management server 16 provides a decryption key for decrypting the health information encrypted each to the first service providing server 17a, the second service providing server 17b, and the third service providing server 17c.

Here, health information is an example of vital sign data, and indicates information of a subject (user) with regard to health, such as a body weight, a body fat, and a blood pressure. Furthermore, the vital sign data indicates information related to a body of living being, such as a subject and a subject animal.

Furthermore, FIG. 1 illustrates a configuration when a user who carries the measuring apparatuses 10a, 10b, and 10c uses health services respectively provided by the first service providing server 17a, the second service providing server 17b, and third service providing server 17c in the health care system 1. In this case, the measuring-apparatus cards 11a, 11b, and 11c are attached to the measuring apparatuses 10a, 10b, and 10c, respectively. Furthermore, the user terminal 13 collects measurement data obtained by each of the measuring apparatuses and then temporarily accumulates the data. Furthermore, the user-terminal card 14 for transmitting the data to each service providing server is attached to the user terminal 13. Communication between the measuring-apparatus cards 11a, 11b, and 11c and the user-terminal card 14 is performed through an internal network 12. The internal network 12 may include a near field communication path, such as Bluetooth (trademark). Communication between: (i) the user-terminal card 14 and (ii) the first service providing server 17a, the second service providing server 17b, and third service providing server 17c; and (i) the first service providing server 17a, the second service providing server 17b, and the third service providing server 17c and (ii) the key management server 16 is performed through an external network 15. The external network 15 may include a wide area communication path, such as the Internet. Hereinafter, constituent elements included in the health care system 1 will be described.

<Configurations of Measuring Apparatuses 10a, 10b, and 10c>

Hereinafter, the configuration of the measuring apparatus 10a will be described. The description of the configurations of the measuring apparatuses 10b and 10c is omitted herein because of the similar configuration as that of the measuring apparatus 10a.

Figure 2:
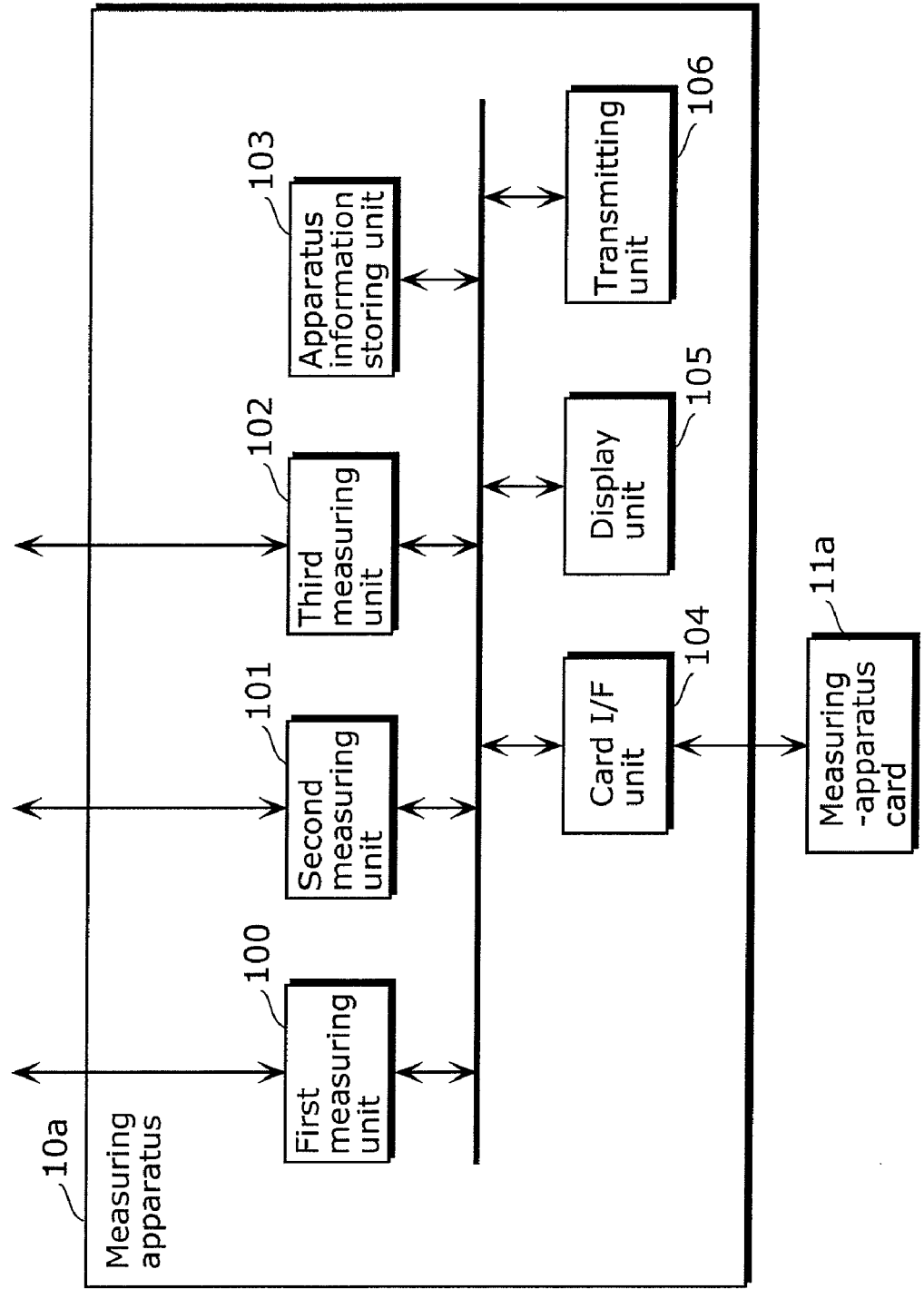
FIG. 2 illustrates a block diagram of a functional configuration of the measuring apparatus according to the first to third embodiments.

FIG. 2 schematically illustrates a functional configuration of the measuring apparatus 10a. As illustrated in FIG. 2, the measuring apparatus 10a includes a first measuring unit 100, a second measuring unit 101, a third measuring unit 102, an apparatus information storing unit 103, a card I/F unit 104, a display unit 105, and a transmitting unit 106.

(First Measuring Unit 100, Second Measuring Unit 101, and Third Measuring Unit 102)

The first measuring unit 100, the second measuring unit 101, and the third measuring unit 102 measure a subject (user) for various health information, such as a body weight and a body fat. Then, the first measuring unit 100, the second measuring unit 101, and the third measuring unit 102 use the obtained various health information as measurement data. Here, the first measuring unit 100 obtains a body weight, the second measuring unit 101 obtains a body fat, and the third measuring unit 102 obtains a pulse. Here, the number of measuring units included in a measuring apparatus depends on the number of categories of health information obtained by such measuring apparatuses. Since the measuring apparatuses 10b and 10c obtain single health information belonging to one category, they only include one measuring unit.

(Apparatus Information Storing Unit 103)

Figure 3:
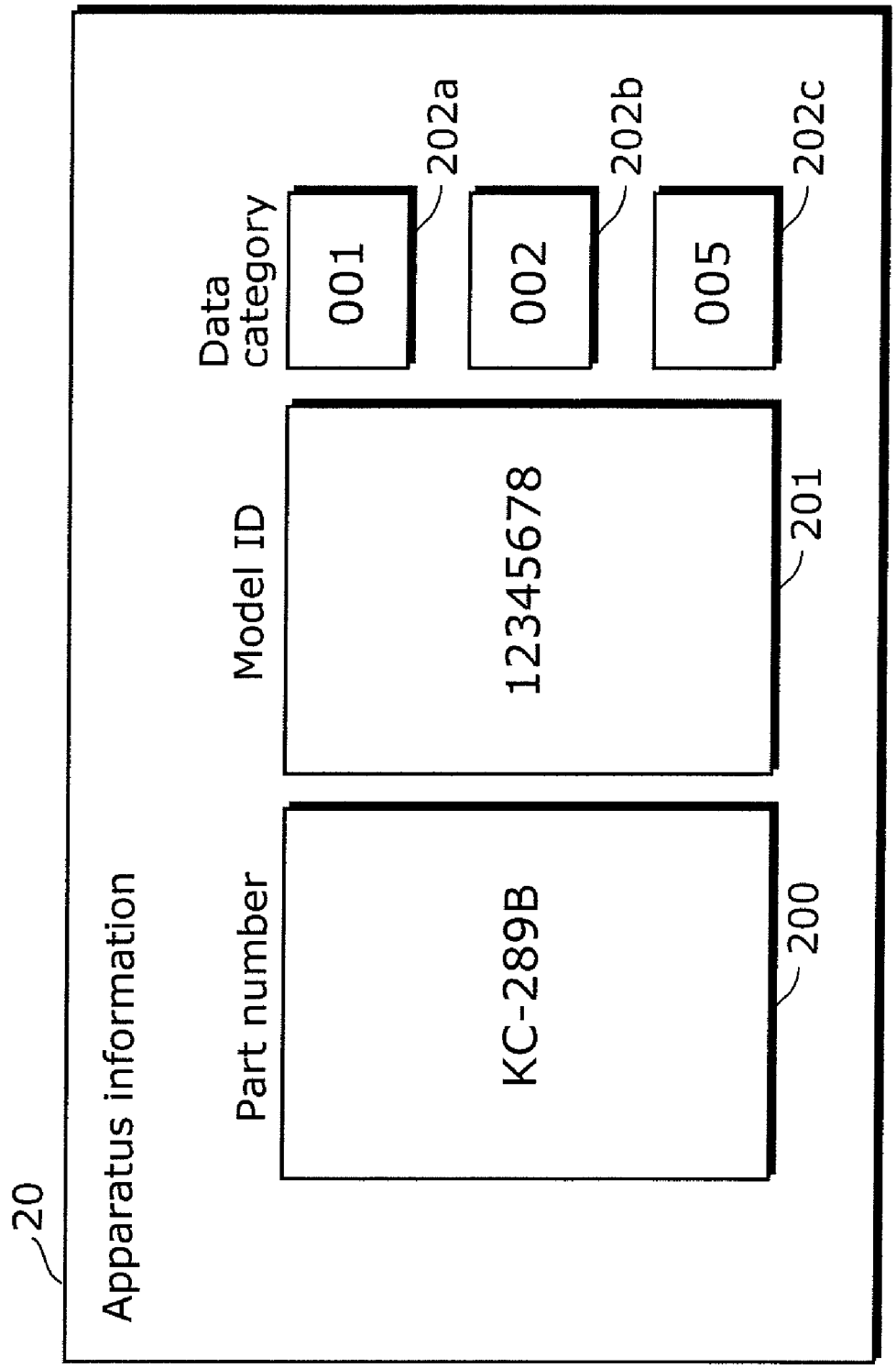
FIG. 3 shows an example of apparatus information according to the first to third embodiments.

Apparatus information 20 of the measuring apparatus 10a is stored in the apparatus information storing unit 103. FIG. 3 shows an example of the apparatus information 20 stored by the apparatus information storing unit 103. The apparatus information 20 includes a part number 200, a model ID 201, and data categories 202a to 202c. A part number is information representing a classification number of a measuring apparatus, and is, for example, composed of alphanumeric characters. In FIG. 3, "KC-289B" is set as a part number. A model ID is information identifying a measuring apparatus. Furthermore, a model ID is information corresponding to a part number of a measuring apparatus on a one-to-one basis, and is, for example, only composed of numeric characters. In FIG. 3, "12345678" is set as a model ID corresponding to the part number "KC-289B". A data category is either information representing a category of health information obtained by a measuring apparatus identified by a part number or a model ID, or information representing a category of measurement data generated by a measuring apparatus identified by a part number or a model ID. A data category is described in accordance with a rule defined for the health care system 1 in advance. For example, "body weight" is described as "001", and "body fat" is described as "002". A measuring apparatus that obtains a plurality of health information sets a plurality of data as data categories. Since the measuring apparatus 10a has a function of obtaining 3 categories of health information (a body weight, a body fat, and a pulse), "001", "002", and "005" each corresponding to the 3 categories of health information are set in the apparatus information 20 in FIG. 3.

(Card I/F Unit 104)

The card I/F unit 104 transmits and receives data to and from the measuring-apparatus card 11a. For example, the card I/F unit 104 transmits, to the measuring-apparatus card 11a, measuring-apparatus transmission data generated by the transmitting unit 106.

(Display Unit 105)

The display unit 105 displays the measurement data obtained by the measuring apparatus 10a to the subject (user).

(Transmitting Unit 106)

The transmitting unit 106 generates measuring-apparatus transmission data including at least measurement data, a model ID, and a data category.

<Configurations of Measuring-Apparatus Cards 11a, 11b, and 11c>

Figure 4:
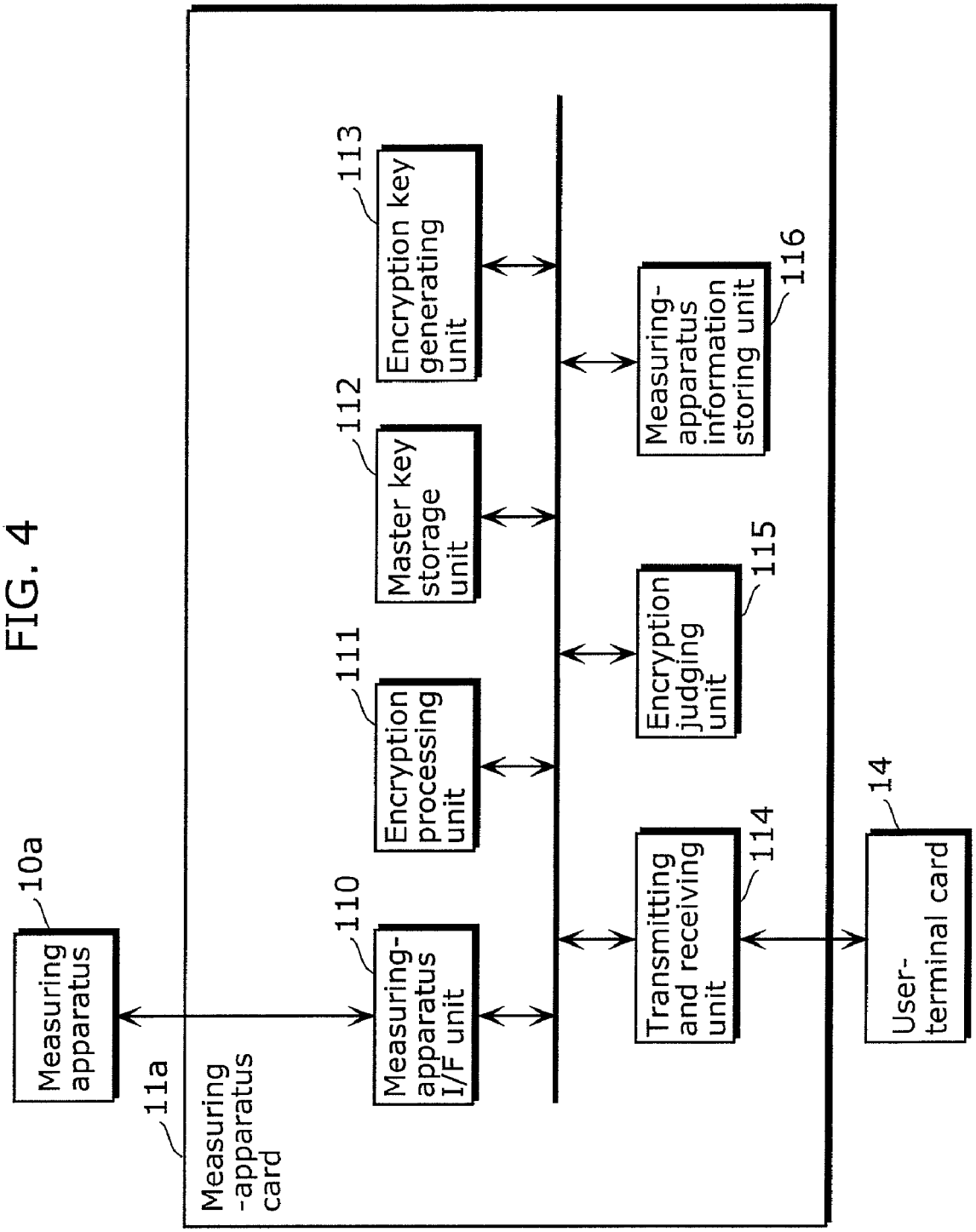
FIG. 4 schematically illustrates a functional configuration of the measuring-apparatus card according to the first and second embodiments.

Hereinafter, the configuration of the measuring-apparatus card 11a will be described. The description of the configurations of the measuring-apparatus cards 11b, and 11c is omitted herein because of the similar configuration as that of the measuring-apparatus card 11a. FIG. 4 schematically illustrates a functional configuration of the measuring-apparatus card 11a. As illustrated in FIG. 4, the measuring-apparatus card 11a includes a measuring-apparatus I/F unit 110, an encryption processing unit 111, a master key storage unit 112, an encryption key generating unit 113, a transmitting and receiving unit 114, an encryption judging unit 115, and a measuring-apparatus information storing unit 116.

(Measuring-Apparatus I/F Unit 110)

The measuring-apparatus I/F unit 110 is an example of an interface unit, and transmits and receives data to and from the measuring apparatus 10a.

(Encryption Processing Unit 111)

Figure 5:
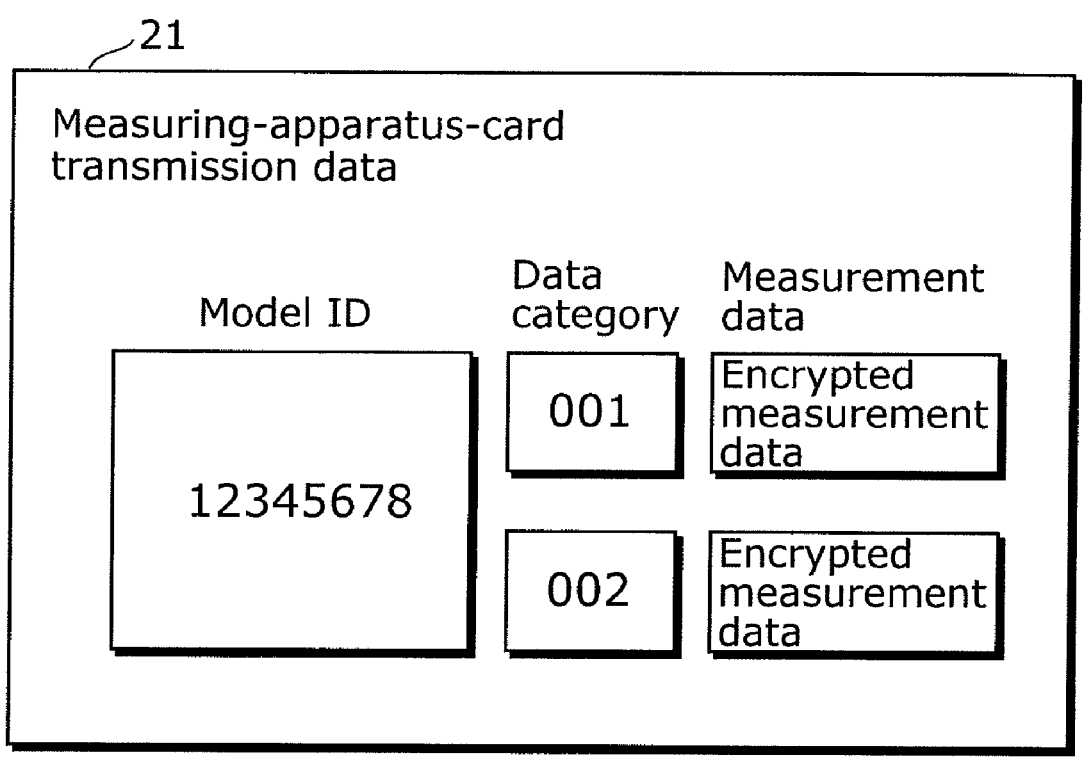
FIG. 5 shows an example of measuring-apparatus-card transmission data according to the first and third embodiments.

The encryption processing unit 111 is an example of an encrypting unit, and encrypts measurement data received from the measuring apparatus 10a to generate the encrypted measurement data. Furthermore, the encryption processing unit 111 generates measuring-apparatus-card transmission data 21 including a model ID, a data category, and encrypted measurement data. FIG. 5 shows an example of the measuring-apparatus-card transmission data 21 generated by the measuring-apparatus card 11a attached to the measuring apparatus 10a. The measuring-apparatus-card transmission data 21 includes the model ID of the measuring apparatus 10a to which the measuring-apparatus card 11a is attached, the data categories of health information obtained by the measuring apparatus 10a, and the encrypted measurement data. Here, details of encryption processing on measurement data by the encryption processing unit 111 will be described later.

(Master Key Storage Unit 112)

A master key is stored in the master key storage unit 112 that is an example of a master key holding unit. A master key is confidential information shared among all of the measuring-apparatus cards, and is set when the measuring-apparatus cards are manufactured.

(Encryption Key Generating Unit 113)

The encryption key generating unit 113 is an example of an encryption key generating unit, and generates an encryption key using a master key, a model ID, and a data category. Thereby, the generated encryption key has a different value depending on a model ID and a data category. Details of generating the encryption key will be described later. Although the first embodiment describes that the encryption key generating unit 113 generates an encryption key, using a master key, a model ID, and a data category, the health care system according to the present invention is not limited to such a health care system. The health care system according to the present invention may be, for example, a health care system in which the encryption key generating unit generates an encryption key using a master key and a model ID.

(Transmitting and Receiving Unit 114)

The transmitting and receiving unit 114 is an example of a communicating unit, and transmits and receives data to and from the user-terminal card 14 through the internal network 12. The transmitting and receiving unit 114 transmits, for example, to the user-terminal card 14, the measuring-apparatus-card transmission data 21 generated by the encryption processing unit 111.

(Encryption Judging Unit 115)

The encryption judging unit 115 judges whether or not the measurement data received from the measuring apparatus 10a needs to be encrypted. The judgment is performed based on measuring-apparatus information 22 stored by the measuring-apparatus information storing unit 116. Details of the judgment will be described later.

(Measuring Apparatus Information Storing Unit 116)

The measuring-apparatus information 22 is stored in the measuring-apparatus information storing unit 116. The measuring-apparatus information 22 includes information regarding the measuring apparatus 10a to which the measuring-apparatus card 11a is attached, and information set according to an instruction from the user-terminal card 14. FIG. 6 shows an example of the measuring-apparatus information 22. The measuring-apparatus information 22 includes the part number, the model ID, the data categories, and transmission necessities. Here, when the measuring-apparatus card 11a is attached to the measuring apparatus 10a, the part number, the model ID, the data categories that are stored by the apparatus information storing unit 103 in the measuring apparatus 10a and that are included in the apparatus information 20 are copied to the measuring-apparatus information 22. More specifically, the part number, the model ID, and the data categories of the apparatus information 20 in FIG. 3 are copied as the part number, the model ID, and the data categories of the measuring-apparatus information 22 in FIG. 6. The transmission necessities are information to be set according to an instruction of the user-terminal card 14 for each data category. More specifically, "1" is set as a transmission necessity when the measuring-apparatus card 11a needs to transmit health information indicated by a data category to the user-terminal card 14, and "0" is set instead when there is no need to transmit the health information thereto. In the measuring-apparatus information 22 in FIG. 6, the transmission necessity "1" (need to be transmitted) is respectively set to the data categories "001" (body weight) and "002" (body fat), and the transmission necessity "0" (need not to be transmitted) is set to the data category "005" (pulse).

Although the first embodiment describes a case where the measuring-apparatus card 11a transmits measurement data received from the measuring apparatus 10a without storing the data, the health care system according to the present invention is not limited to such a health care system. The measuring-apparatus card 11a may include, for example, a storing unit that stores measurement data received from the measuring apparatus 10a.

<Configuration of the User Terminal 13>

The user terminal 13 is a terminal, such as a PC and a television. The user-terminal card 14 is attached to the user terminal 13 that provides a user interface for operating data, mainly in the user-terminal card 14.

<Configuration of User-Terminal Card 14>

Figure 7:
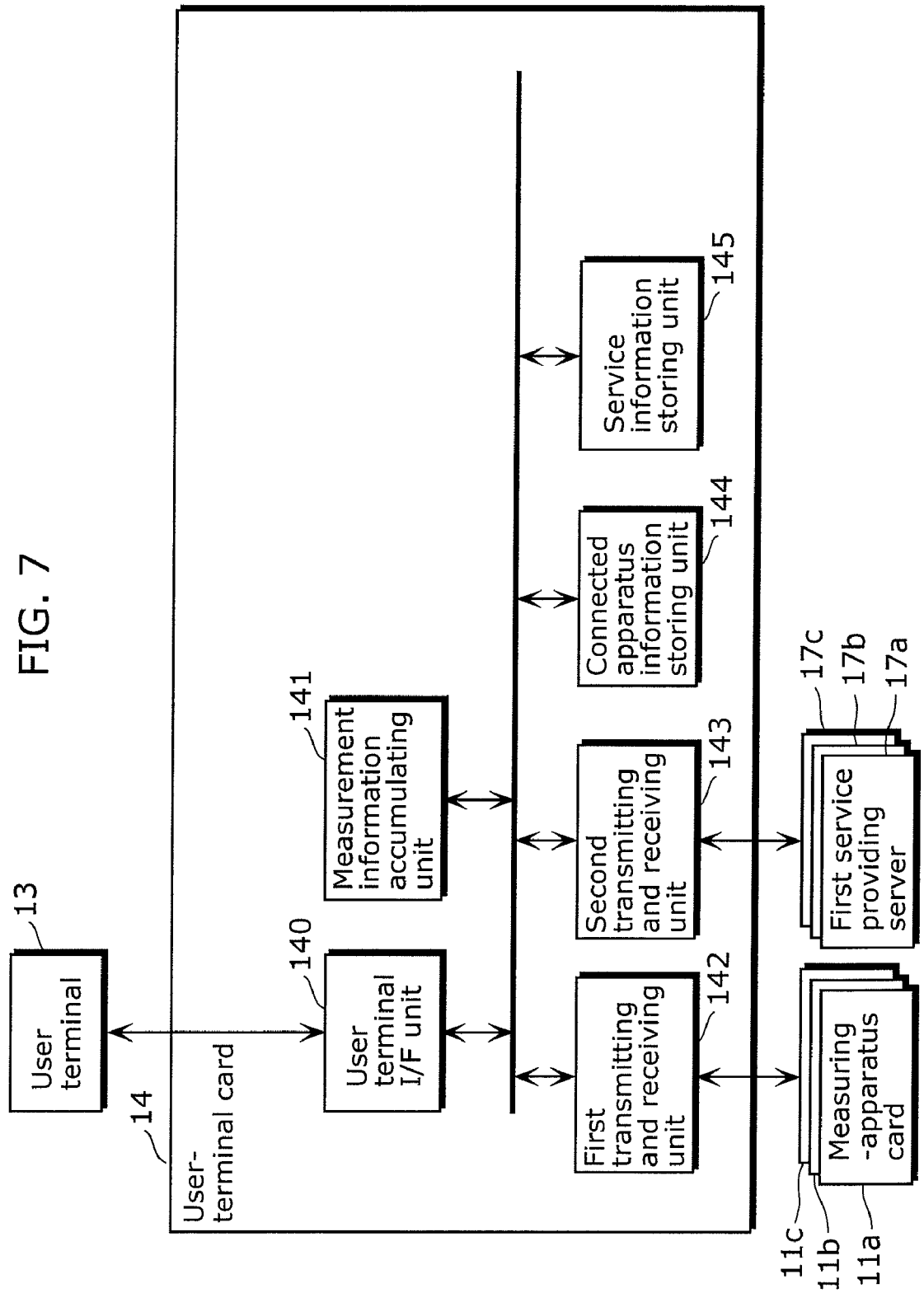
FIG. 7 illustrates a block diagram of a functional configuration of the user-terminal card according to the first to third embodiments.

FIG. 7 schematically illustrates a functional configuration of the user-terminal card 14. As illustrated in FIG. 7, the user-terminal card 14 includes a user terminal I/F unit 140, a measurement information accumulating unit 141, a first transmitting and receiving unit 142, a second transmitting and receiving unit 143, a connected apparatus information storing unit 144, and a service information storing unit 145.

(User Terminal I/F Unit 140)

The user terminal I/F unit 140 is an interface for transmitting and receiving data to and from the user terminal 13.

(Connected Apparatus Information Storing Unit 144)

The connected apparatus information storing unit 144 stores connected apparatus information 23. The connected apparatus information 23 includes information identifying a measuring-apparatus card that is connected to the user-terminal card 14, information of a measuring apparatus to which the measuring-apparatus card is attached, and information of whether or not health information obtained by the measuring apparatus needs to be accumulated in the user-terminal card 14. FIG. 8 shows an example of the connected apparatus information 23. IDs of the measuring-apparatus cards, and the model IDs and data categories of the measuring apparatus information 22 that are stored in the measuring-apparatus information storing unit 116 for each of the measuring-apparatus cards are copied as the measuring-apparatus-card IDs, model IDs, and data categories included in the connected apparatus information 23, when the user-terminal card 14 is connected to each of the measuring-apparatus cards 11a, 11b, and 11c. An accumulation necessity is information to be set for each data category. More specifically, "1" is set as an accumulation necessity when the user-terminal card 14 needs to accumulate health information identified by a data category, and "0" is set instead when there is no need to accumulate the health information. The connected apparatus information 23 in FIG. 8 indicates that the user-terminal card 14 is connected to the user-terminal cards having measuring-apparatus-card IDs, "186512", "392138", and "912356". Moreover, the connected apparatus information 23 indicates that the user-terminal cards are respectively attached to the measuring apparatuses having the model IDs "12345678", "2468912", and "8642013". Furthermore, the connected apparatus information 23 indicates that the measuring apparatus 10a having the model ID "12345678" needs to accumulate measurement data of body weight identified by the data category "001" and body fat identified by the data category "002". On the other hand, the connected apparatus information 23 indicates that the measuring apparatus 10b having the model ID "2468912" needs to accumulate measurement data of a blood pressure identified by the data category "004".

(Measurement Information Accumulating Unit 141)

Figure 9:
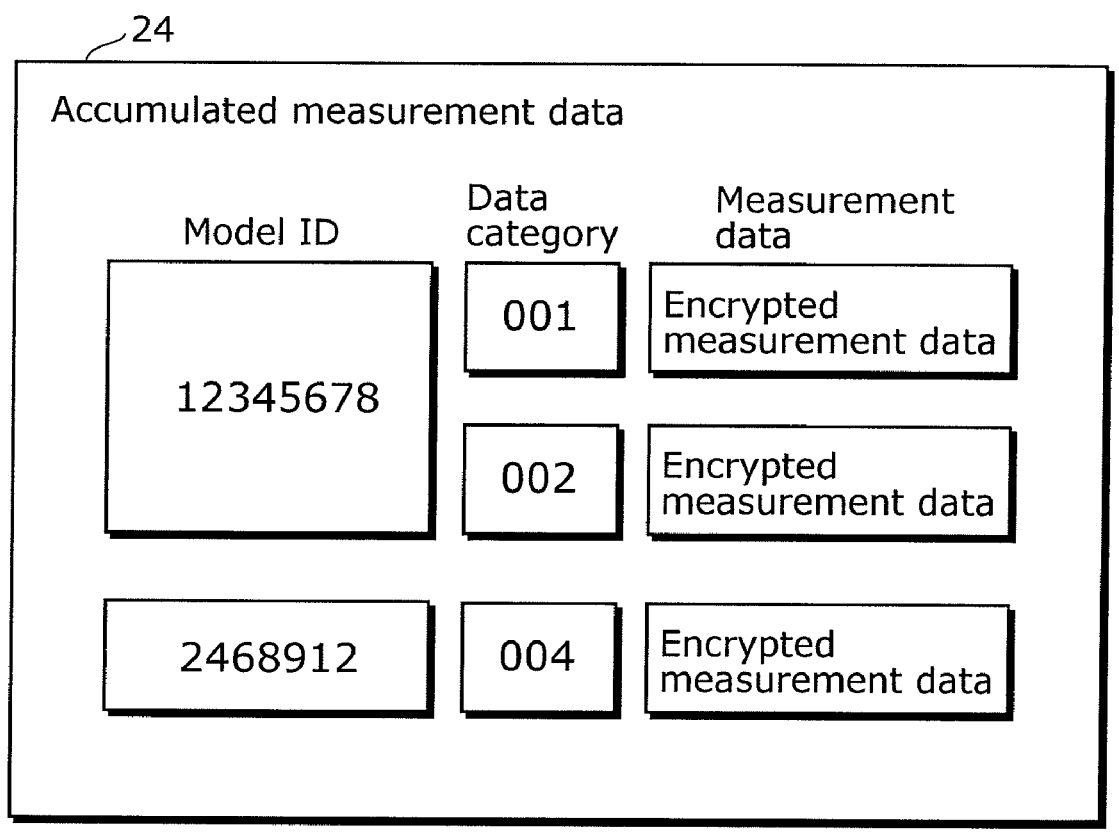
FIG. 9 shows an example of accumulated measurement data according to the first to third embodiments.

The measurement information accumulating unit 141 accumulates, as accumulated measurement data, encrypted measurement data transmitted from each of the measuring apparatuses through each of the measuring-apparatus cards. FIG. 9 shows an example of the accumulated measurement data 24. The accumulated measurement data 24 includes the model IDs, data categories, and measurement data. The model ID and data category corresponding to the accumulation necessity "1" (need to be accumulated) from the connected apparatus information 23 stored in the connected apparatus information storing unit 144 are copied to the accumulated measurement data 24. The measurement data in the accumulated measurement data 24 is data by storing, for each model ID and data category, the encrypted measurement data transmitted from each of the measuring-apparatus cards.

(First Transmitting and Receiving Unit 142)

The first transmitting and receiving unit 142 transmits and receives data to and from the measuring-apparatus cards 11a, 11b, and 11c through the internal network 12.

(Second Transmitting and Receiving Unit 143)

The second transmitting and receiving unit 143 transmits and receives data to and from the first service providing server 17a, the second service providing server 17b, and the third service providing server 17c through the external network 15. For example, the second transmitting and receiving unit 143 transmits, to the first service providing server 17a, the user-terminal-card transmission data including model IDs, data categories, and encrypted measurement data.

(Service Information Storing Unit 145)

The service information storing unit 145 stores service information 25 including services to be used by the user and health information necessary for the services, and information indicating which measuring apparatus provides the health information.

FIG. 10 shows an example of the service information 25.

A service ID identifies a service providing server that provides a service registered for use by the user. Necessary data categories are set for each of the service IDs, and indicate data categories of health information necessary for services indicated by each service ID. When a plurality of health information is necessary for one service, a plurality of necessary data categories is set for one service ID of the one service. A data obtainment measuring-apparatus-card ID is information identifying a measuring-apparatus card that obtains health information identified by a necessary data category. A data obtainment model ID indicates a model ID of a measuring apparatus to which the measuring-apparatus card is attached.

For example, the service information 25 in FIG. 10 indicates that services provided by the service providing servers identified by the service IDs "0002" and "0148" are used. Moreover, the service information 25 indicates that the service providing servers identified by the service IDs "0002" and "0148" need health information identified by the necessary data categories "001" and "004". Furthermore, the service information 25 indicates that the health information identified by the necessary data categories "001", "004", and "002" are obtained from the measuring-apparatus cards identified by the measuring-apparatus-card IDs "186512", "392138", and "186512", respectively. Additionally, the service information 25 indicates that the measuring-apparatus cards identified by the measuring-apparatus-card IDs "186512", "392138", and "186512" obtain measurement data from the measuring apparatuses identified by the model IDs "12345678", "2468912", and "12345678", respectively.

<First Service Providing Server 17a, Second Service Providing Server 17b, and Third Service Providing Server 17c>

Figure 11:
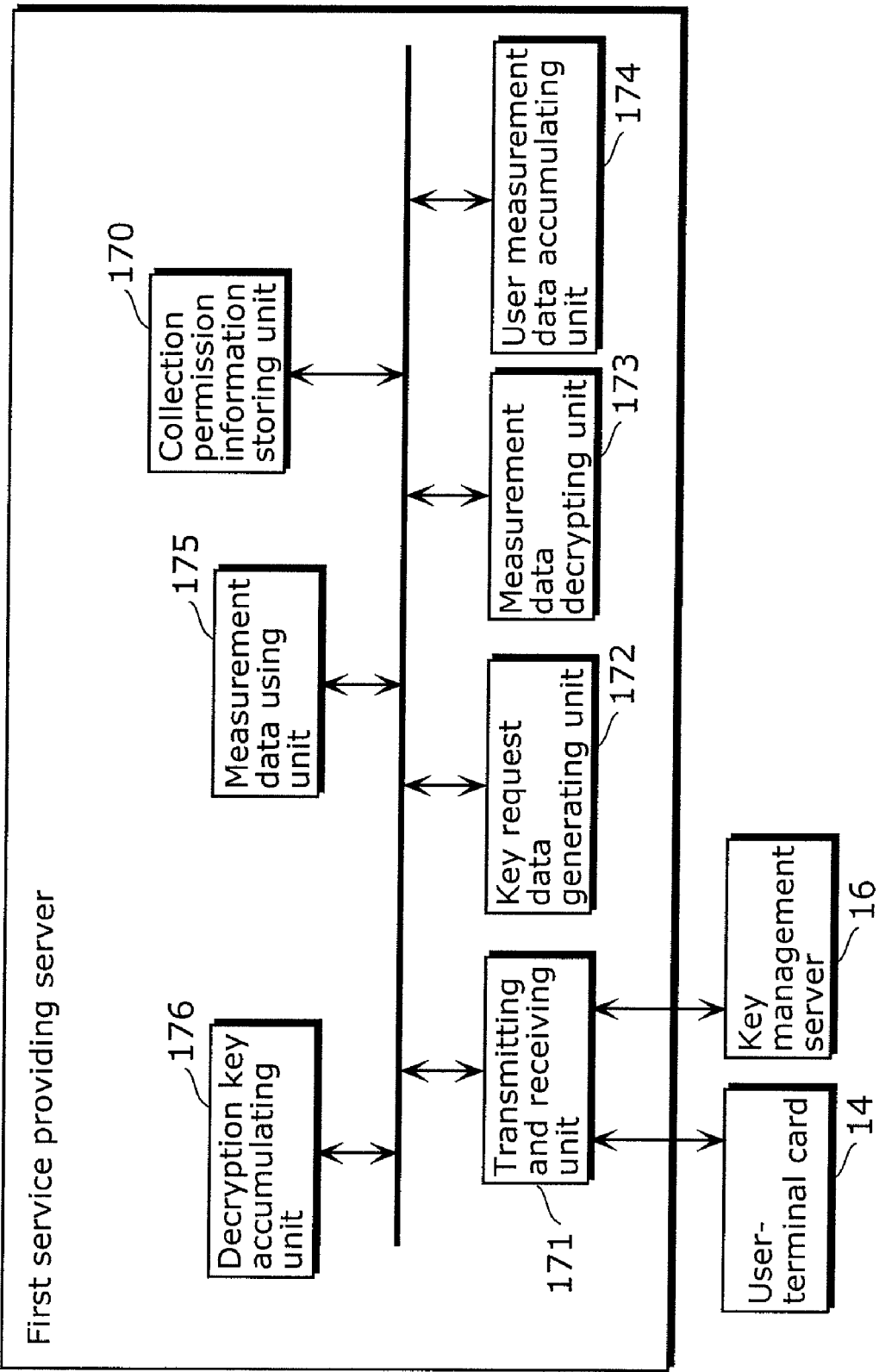
FIG. 11 illustrates a block diagram of a functional configuration of the first service providing server according to the first to third embodiments.

Hereinafter, the configuration of the first service providing server 17a will be described. The description of the configurations of the second service providing server 17b and the third service providing server 17c is omitted herein because of the similar configuration as that of the first service providing server 17a. FIG. 11 schematically illustrates a functional configuration of the first service providing server 17a.

(Collection Permission Information Storing Unit 170)

Collection permission information 26 including information identifying the first service providing server 17a and information identifying health information that permits the first service providing server 17a to collect is stored in a collection permission information storing unit 170.

Figure 12:
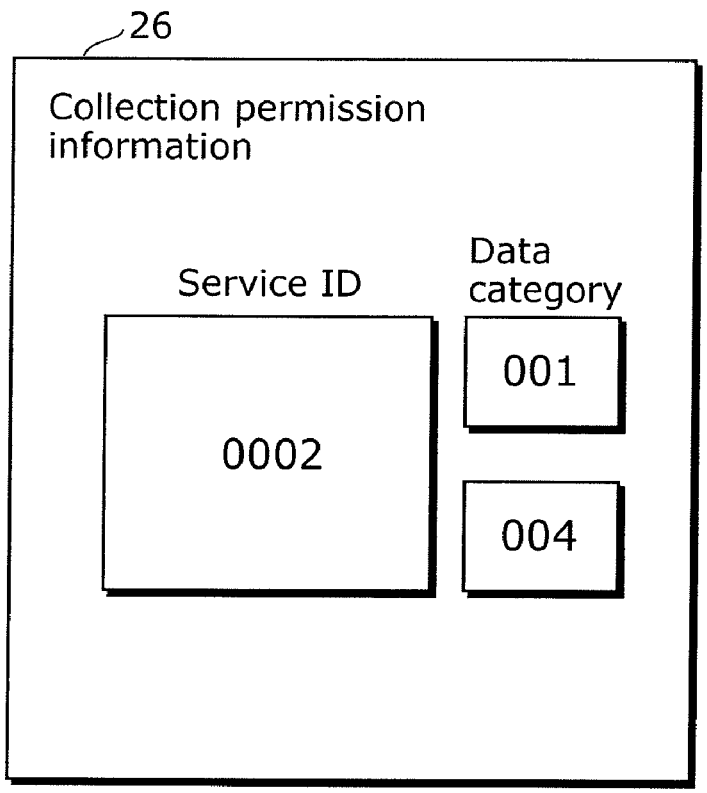
FIG. 12 shows an example of collection permission information according to the first to third embodiments.

FIG. 12 shows an example of the collection permission information 26. The collection permission information 26 indicates that the first service providing server 17a identified by the service ID "0002" is permitted to collect measurement data having the data categories "001" (body weight) and "004" (blood pressure).

(Transmitting and Receiving Unit 171)

A transmitting and receiving unit 171 is an example of a communicating unit, and transmits and receives data to and from the user-terminal card 14 and the key management server 16 through the external network 15. The transmitting and receiving unit 171 transmits, for example, key request data 27 generated by a key request data generating unit 172 to the key management server 16.

(Key Request Data Generating Unit 172)

Figure 13:
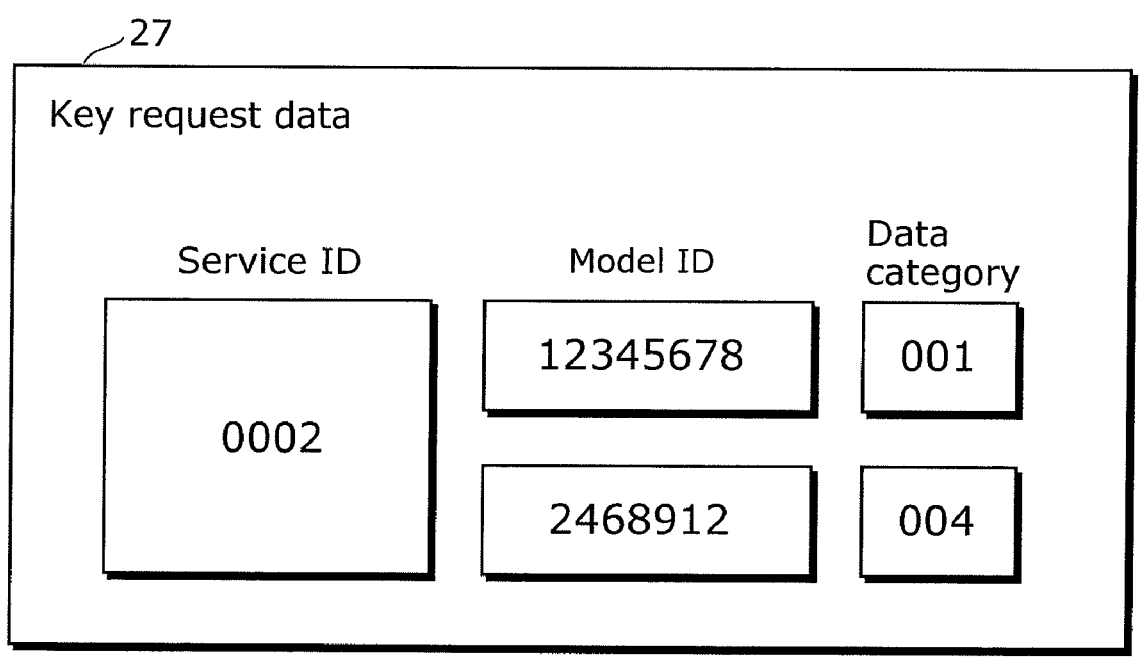
FIG. 13 shows an example of key request data according to the first and third embodiments.

The key request data generating unit 172 generates the key request data 27 for requesting the key management server 16 to transmit a decryption key for decrypting the encrypted measurement data received from the user-terminal card 14. The key request data 27 includes information identifying a measuring apparatus, information identifying a category of health information, and information identifying a service providing server. FIG. 13 shows an example of the key request data 27. As in FIG. 13, the key request data 27 includes a service ID of a service providing server, and a model ID and a data category included in user-terminal-card transmission data. The key request data 27 in FIG. 13 indicates that the first service providing server 17a having the service ID "0002" requests a decryption key corresponding to a measuring apparatus of the model ID "2468912" and the data category "004".

(Measurement Data Decrypting Unit 173)

The measurement data decrypting unit 173 decrypts encrypted measurement data using a decryption key obtained from the key management server 16. Details of the decryption will be described later.

(User Measurement Data Accumulating Unit 174)

The user measurement data accumulating unit 174 is an example of a storing unit, and accumulates the model ID, the data category, and encrypted measurement data that are received from the user-terminal card 14. Furthermore, the user measurement data accumulating unit 174 accumulates the measurement data obtained by decrypting the encrypted measurement data.

(Measurement Data Using Unit 175)

The measurement data using unit 175 provides the user with a service using the measurement data decrypted by the measurement data decrypting unit 173.

(Decryption Key Accumulating Unit 176)

Figure 14:
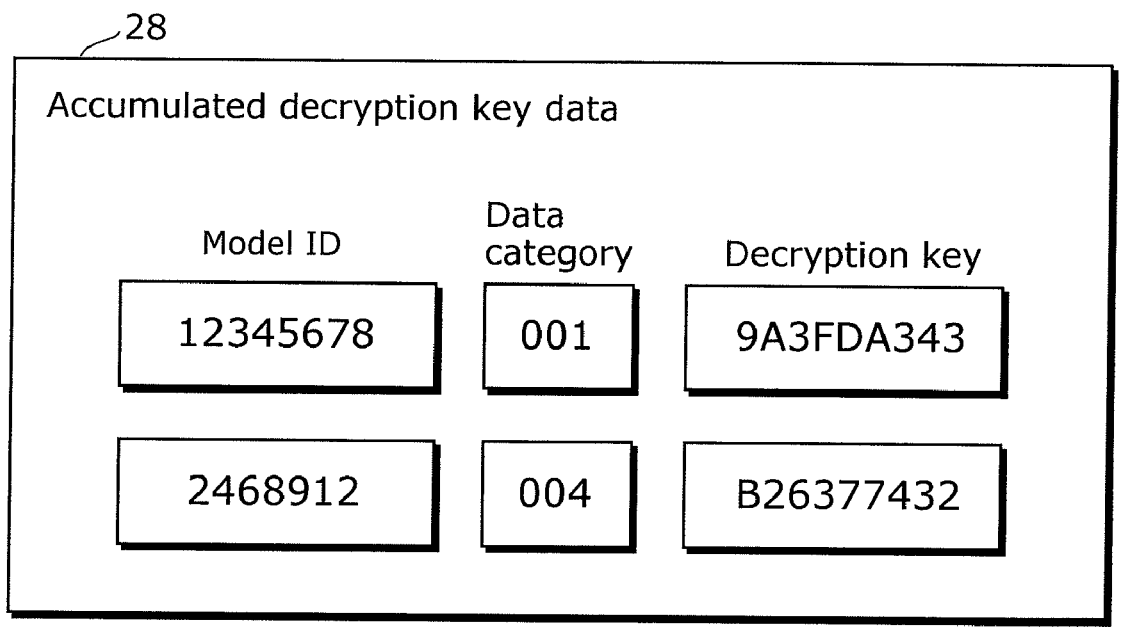
FIG. 14 shows an example of accumulated decryption key data according to the first and third embodiments.

The decryption key accumulating unit 176 accumulates a decryption key received from the key management server 16. FIG. 14 shows an example of accumulated decryption key data 28 accumulated by the decryption key accumulating unit 176. As shown in FIG. 14, the accumulated decryption key data 28 includes the model IDs, the data categories, and decryption keys. For example, the accumulated decryption key data 28 indicates that a decryption key for measurement data corresponding to the model ID "12345678" and the data category "001" (body weight) is "9A3FDA343".

<Configuration of Key Management Server 16>

Figure 15:
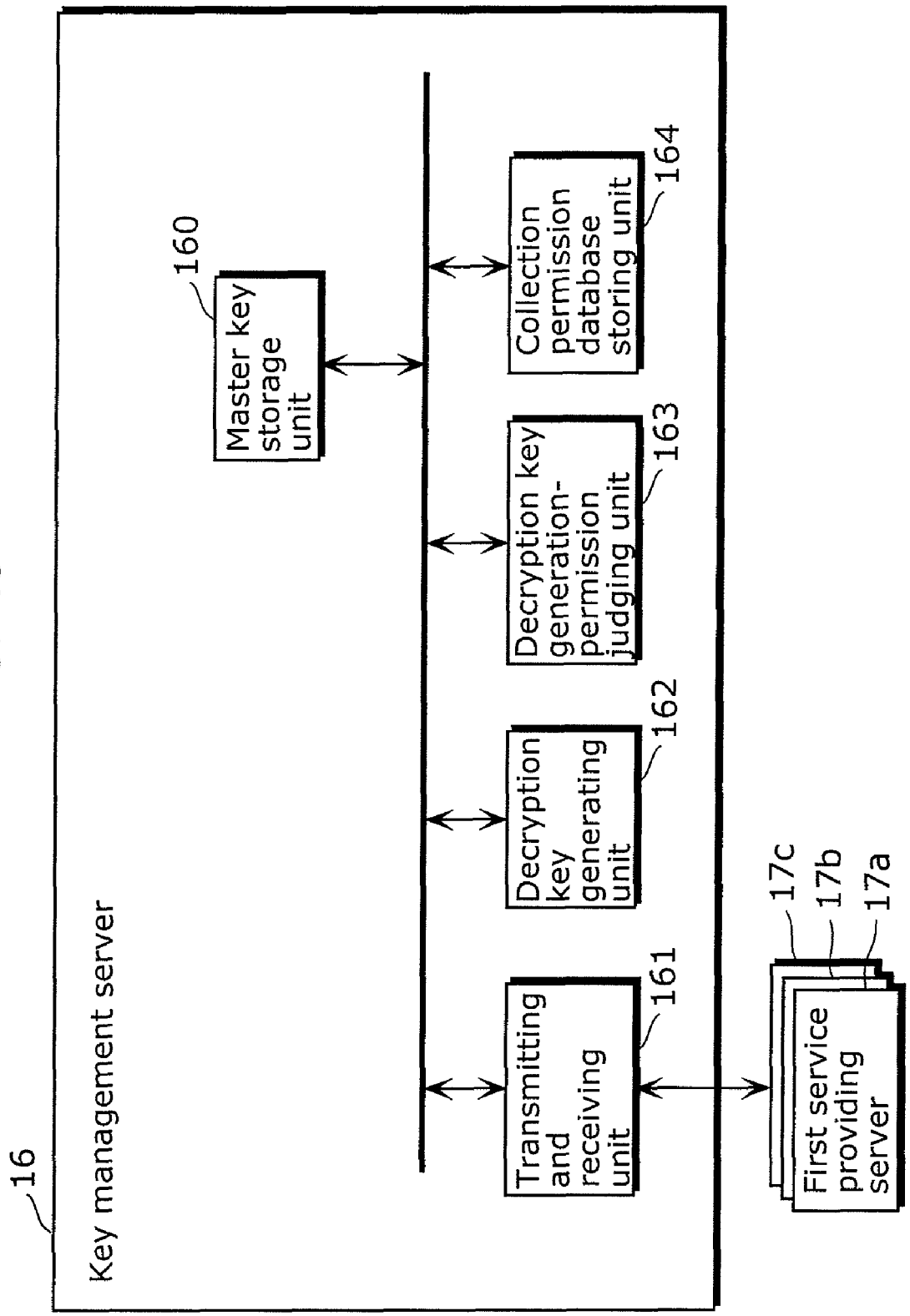
FIG. 15 illustrates a block diagram of a functional configuration of the key management server according to the first embodiment.

FIG. 15 schematically illustrates a functional configuration of the key management server 16.

(Master Key Storage Unit 160)

The master key storage unit 160 is an example of a master key holding unit, and stores a master key. The master key is shared by the measuring-apparatus cards.

(Transmitting and Receiving Unit 161)

The transmission and receiving unit 161 transmits and receives data to and from the first service providing server 17a, the second service providing server 17b, and the third service providing server 17c through the external network 15. The transmission and receiving unit 161, for example, transmits a decryption key generated by a decryption key generating unit 162 to the first service providing server 17a according to an instruction from a decryption key generation-permission judging unit 163.

(Decryption Key Generating Unit 162)

The decryption key generating unit 162 is an example of a key generating unit, and generates a decryption key based on a master key stored in the master key storage unit 160, and a model ID and a data category included in the key request data 27, according to a request from a service providing server. In other words, the decryption key generating unit 162 generates, as a decryption key, a key identical to an encryption key for use in encrypting measurement data by a measuring-apparatus card. Details of the generating of a key will be described later. Here, the decryption key generating unit 162 may generate a decryption key using a master key and a model ID, as the encryption key generating unit 113 included in each of the measuring-apparatus cards.

(Decryption Key Generation-Permission Judging Unit 163)

The decryption key generation-permission judging unit 163 is an example of a control unit, and judges whether or not a decryption key is generated using a collection permission database 29 stored in a collection permission database storing unit 164, in response to a decryption key request from a service providing server. When judging that a decryption key is generated, the decryption key generation-permission judging unit 163 instructs the decryption key generating unit 162 to generate the decryption key, and instructs the transmission and receiving unit 161 to transmit the generated decryption key.

(Collection Permission Database Storing Unit 164)

Figure 16:
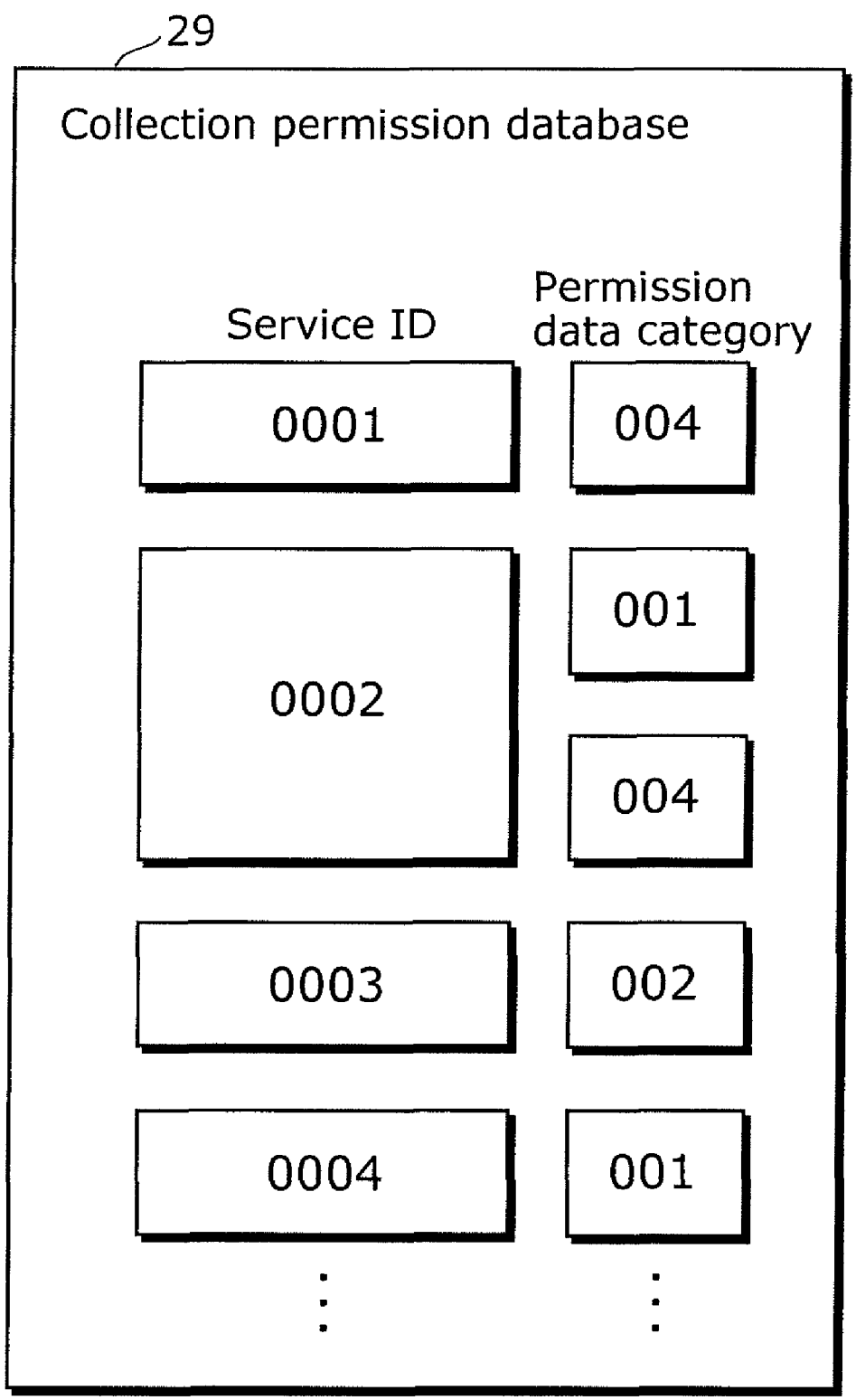
FIG. 16 shows an example of a collection permission database according to the first to third embodiments.

The collection permission database 29 is stored in the collection permission database storing unit 164. The collection permission database 29 stores data categories of health information that each of the service providing servers is permitted to collect. FIG. 16 shows an example of the collection permission database 29. The service IDs identify the service providing servers. Permission data categories are data categories of health information that each of the service providing servers is permitted to collect. Here, assume that a key management center that manages a key management server enters into a contract regarding a permission to collect health information with each of health care service providers in advance, and the collection permission database 29 is set based on details of the contract.

Next, various operations of the health care system 1 having the aforementioned configuration will be described.

Figure 17:
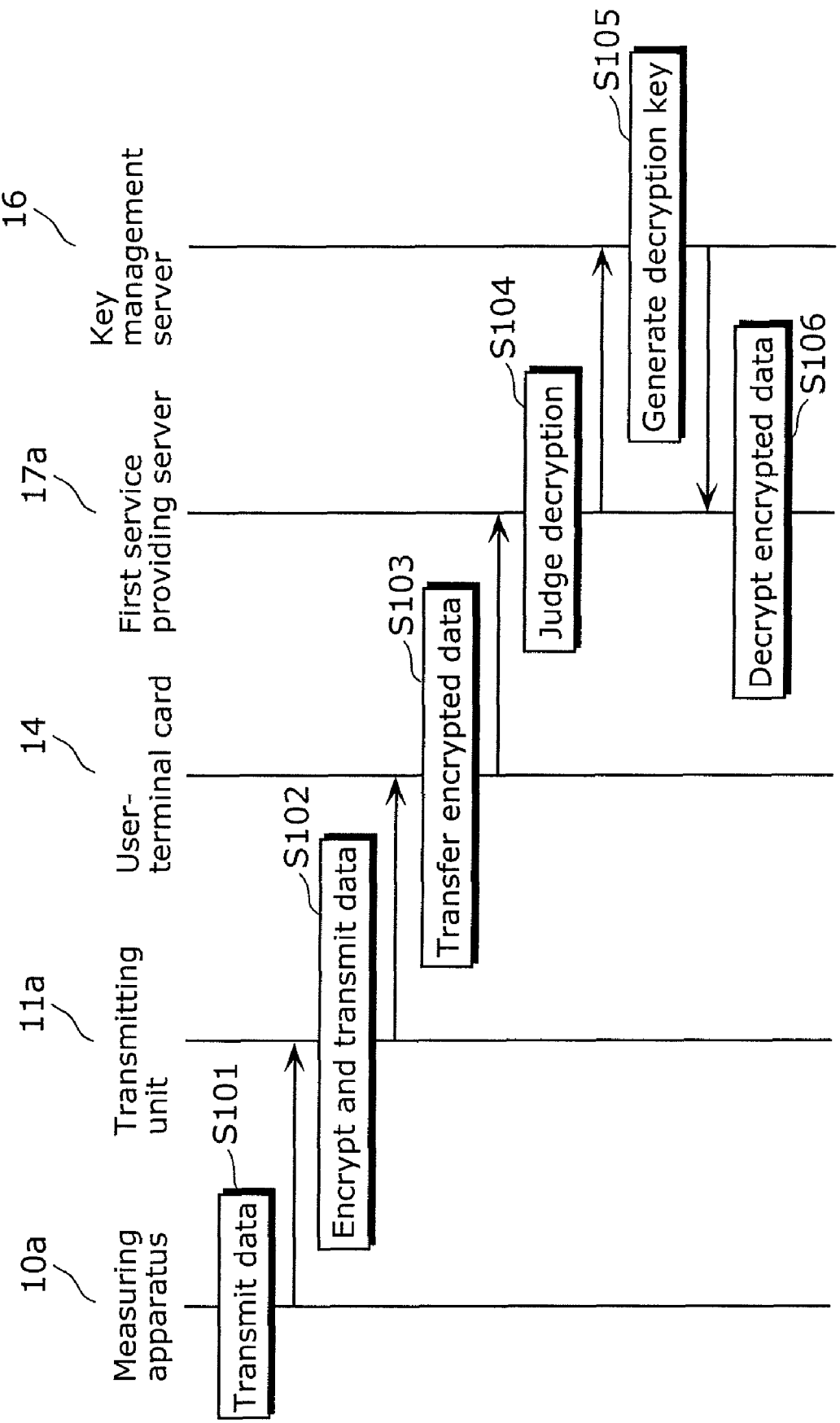
FIG. 17 shows sequences of entire processing in the health care system according to the first to third embodiments.

FIG. 17 shows sequences of entire processing in the health care system 1.

First, the measuring apparatus 10a measures the user for health information. Then, the measuring apparatus 10a transmits measuring-apparatus transmission data including at least a model ID, a data category, and measurement data to the measuring-apparatus card 11a (Step S101).

Next, the measuring-apparatus card 11a encrypts the measurement data included in the received measuring-apparatus transmission data. Then, the measuring-apparatus card 11a transmits the measuring-apparatus-card transmission data 21 including a model ID, a data category, and the encrypted measurement data to the user-terminal card 14 (Step S102).

Next, the user-terminal card 14 identifies a service ID corresponding to the model ID and data category included in the measuring-apparatus-card transmission data 21. Then, the user-terminal card 14 transfers the user-terminal-card transmission data that includes the encrypted measurement data corresponds to the model ID and the data category to a service providing server corresponding to the identified service ID (here, the first service providing server 17a)(Step S103).

Next, the first service providing server 17a judges whether or not to decrypt the encrypted measurement data. Then when judging the data to be decrypted, the first service providing server 17a transmits, to the key management server 16, the key request data 27 including the service ID, the model IDs, and the data categories that are included in the received user-terminal-card transmission data (Step S104).

Next, the key management server 16 generates a decryption key corresponding to the key request data 27 when the received key request data 27 satisfies a predetermined condition, and transmits decryption key data including the generated decryption key to the first service providing server 17a (Step S105).

Next, the first service providing server 17a decrypts the encrypted measurement data using a decryption key included in the decryption key data (Step S106).

Next, detailed operations of the measuring apparatus 10a, the measuring-apparatus card 11a, the user-terminal card 14, the first service providing server 17a, and the key management server 16 will be described.

<Measuring Health Information Using Measuring Apparatus 10a>

Figure 18:
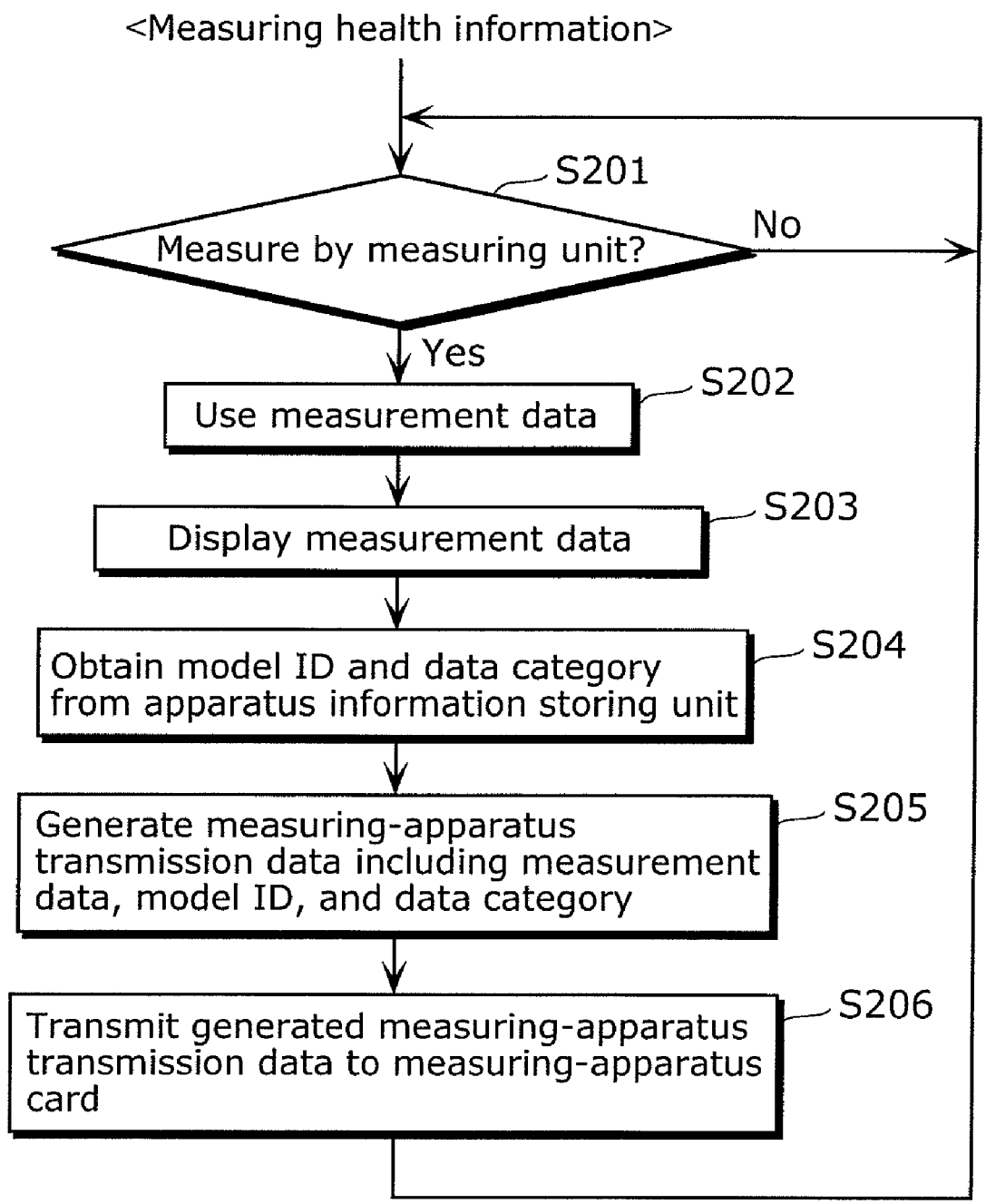
FIG. 18 shows a flowchart indicating measuring of health information using the measuring apparatus according to the first to third embodiments.

FIG. 18 shows a flowchart indicating processes for measuring health information using the measuring apparatus 10a.

First, the first measuring unit 100, the second measuring unit 101, or the third measuring unit 102 judges whether or not to have measured the user for health information (Step S201). Here, when health information of the user has not been measured (No in Step S201), the first measuring unit 100, the second measuring unit 101, or the third measuring unit 102 again judges whether or not to have measured the user for health information (Step S201). On the other hand, when health information of the user has been measured (Yes in Step S201), the first measuring unit 100, the second measuring unit 101, or the third measuring unit 102 uses the health information as measurement data (Step S202).

Next, the display unit 105 displays the generated measurement data (Step S203).

Next, the transmitting unit 106 obtains a model ID and a data category from the apparatus information 20 stored in the apparatus information storing unit 103 (Step S204). For example, in the case of the measurement data generated by the first measuring unit 100, the transmitting unit 106 obtains the model ID "12345678" and the data category "001" from the apparatus information 20 shown in FIG. 3.

Next, the transmitting unit 106 generates measuring-apparatus transmission data including the obtained model ID and data category and the measurement data generated in Step S202 (Step S205). For example, the measurement data generated by the first measuring unit 100 is defined as the first measurement data, the one by the second measuring unit 101 is defined as the second measurement data, and the one by the third measuring unit 102 is defined as the third measurement data. In this case, the transmitting unit 106 obtains the model ID 201, the data categories 202a, 202b, and 202c shown in FIG. 3. Then, the transmitting unit 106 generates the first, second, and third measuring-apparatus transmission data in the following data format, and transmits them to the measuring-apparatus card 11a.

First measuring-apparatus transmission data=(model ID 201, data category 202a, first measurement data)

Second measuring-apparatus transmission data=(model ID 201, data category 202b, second measurement data)

Third measuring-apparatus transmission data=(model ID 201, data category 202c, third measurement data)

Here, "D=(A, B, C)" represents that data D includes data A, B, and C.

Next, the card I/F unit 104 transmits, to the measuring-apparatus card 11a, the generated measuring-apparatus transmission data to the measuring-apparatus card 11a (Step S206). Then, the measuring apparatus 10a repeats the processes from Steps S201 to S206.

As described above, the measuring apparatus 10a transmits, to the measuring-apparatus card 11a, the measuring-apparatus transmission data including measurement data that is health information obtained from the user through measurement.

<Encrypting and Transmitting of Measurement Data Using the Measuring-Apparatus Card 11a>

Next, processing of the measuring-apparatus card 11a that encrypts measurement data obtained by the measuring apparatus 10a and transmits the encrypted measurement data will be described.

Figure 19:
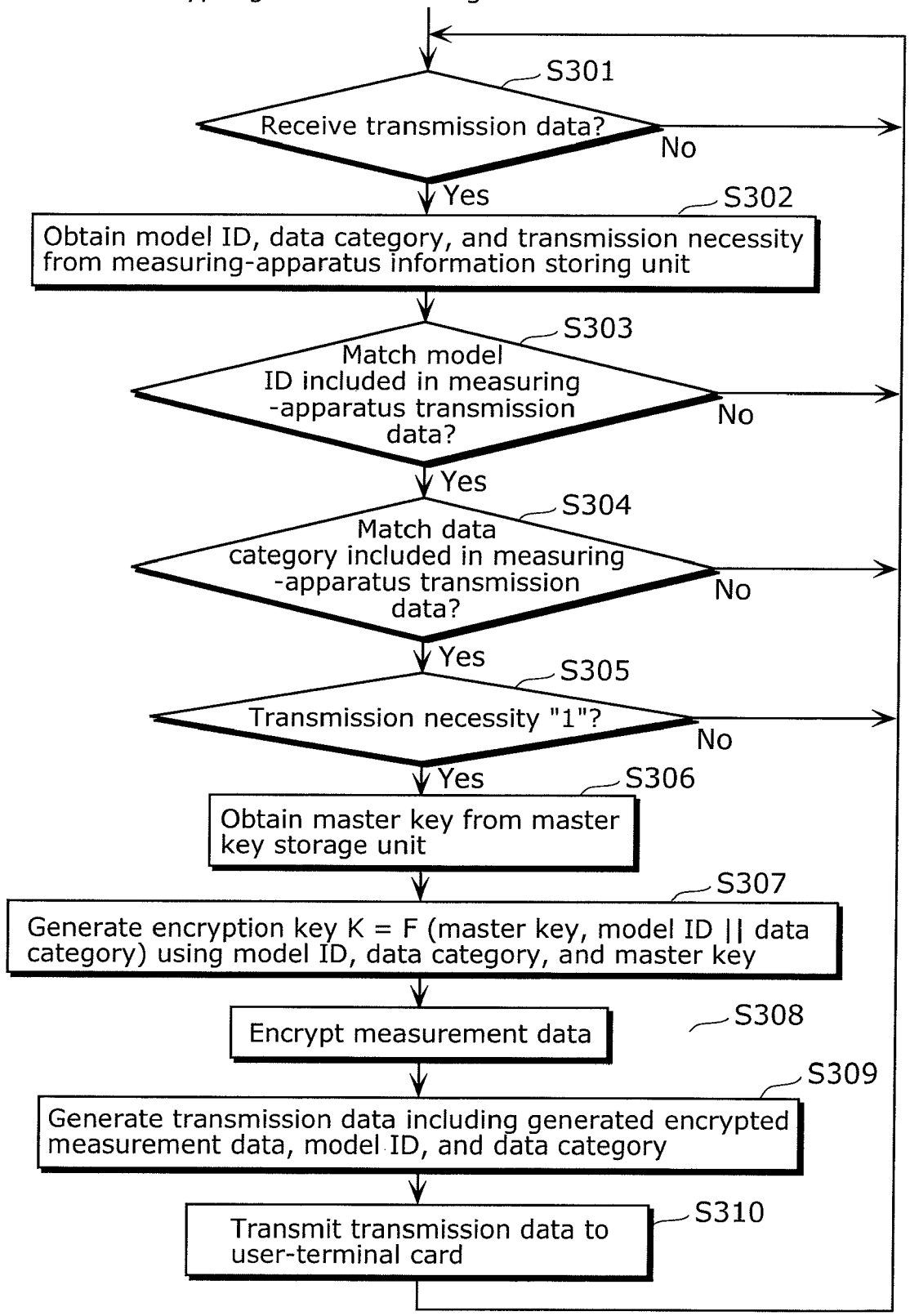
FIG. 19 shows a flowchart indicating encrypting and transmitting measurement data using the measuring-apparatus card according to the first embodiment.

FIG. 19 shows a flowchart indicating the encrypting and transmitting of measurement data using the measuring-apparatus card 11a.

First, the measuring-apparatus I/F unit 110 judges whether or not the measuring-apparatus card 11a receives measuring-apparatus transmission data (Step S301). Here, when the measuring-apparatus card 11a does not receive the data (No in Step S301), again, the measuring-apparatus I/F unit 110 judges whether or not the measuring-apparatus card 11a receives measuring-apparatus transmission data (Step S301). On the other hand, upon receipt of the data (Yes in Step S301), the encryption judging unit 115 obtains a model ID, a data category, and a transmission necessity from the measuring-apparatus information 22 stored in the measuring-apparatus information storing unit 116 (Step S302).

Next, the encryption judging unit 115 judges whether or not there is a matching model ID included in the measuring-apparatus transmission data among the model IDs obtained from the measuring-apparatus information 22 (Step S303). When there is no matching model ID (No in Step S303), the encryption judging unit 115 discards the measuring-apparatus transmission data. Then, the measuring-apparatus I/F unit 110 judges whether or not the measuring-apparatus card 11a receives measuring-apparatus transmission data (Step S301). When there is a matching model ID (Yes in Step S303), the encryption judging unit 115 judges whether or not a data category corresponding to the model ID matches the data category included in the measuring-apparatus transmission data (Step S304). Here, when the data category corresponding to the model ID does not match the data category included in the measuring-apparatus transmission data (No in Step S304), the encryption judging unit 115 discards the measuring-apparatus transmission data. Then, the measuring-apparatus I/F unit 110 judges whether or not the measuring-apparatus card 11a has received measuring-apparatus transmission data (Step S301). Here, when the data category corresponding to the model ID matches the data category included in the measuring-apparatus transmission data (Yes in Step S304), the encryption judging unit 115 judges whether or not a transmission necessity corresponding to the model ID and the data category indicates "1" (Step S305). When the transmission necessity does not indicate "1" (No in Step S305), the encryption judging unit 115 discards the measuring-apparatus transmission data. Then, the measuring-apparatus I/F unit 110 judges whether or not the measuring-apparatus card 11a has received measuring-apparatus transmission data (Step S301). On the other hand, when the transmission necessity indicates "1" (Yes in Step S305), the encryption key generating unit 113 obtains a master key stored in the master key storage unit 112 (Step S306).

For example, since the transmission necessity corresponding to the first and second measuring-apparatus transmission data in the measuring-apparatus information 22 in FIG. 6 is "1" (need to be transmitted), the measuring-apparatus I/F unit 110 judges that the first measurement data included in the first transmission data and the second measurement data included in the second transmission data need to be encrypted and transmitted to the user-terminal card 14. On the other hand, since the transmission necessity corresponding to the third measuring-apparatus transmission data is "0" (need not to be transmitted), the third measurement data need to be neither encrypted nor transmitted to the user-terminal card 14.

Although the encryption judging unit 115 discards, without encryption, measurement data that is not necessary to be transmitted to the user-terminal card 14, in other words, health information that is not necessary to be transmitted for use in a health care service, the measurement data may be accumulated in a local accumulating unit within the user terminal 13, the user-terminal card 14, or the measuring-apparatus card 11a. The encryption judging unit 115 may judge whether or not health information is accumulated in a local accumulating unit based on information for judgment. Furthermore, the measurement data accumulated in the local accumulating unit may be encrypted in the same manner as described above. Furthermore, the encryption judging unit 115 may judge whether or not to encrypt measurement data accumulated in a local accumulating unit, based on information defined for judging whether or not to be encrypted. Furthermore, the encryption judging unit 115 may judge whether or not to encrypt measurement data to be transmitted to the user-terminal card 14, based on information defined for judging whether or not to be encrypted.

Next, the encryption key generating unit 113 generates an encryption key using the model ID, the data category, and the master key (Step S307).

Then, the encryption processing unit 111 encrypts measurement data included in the measuring-apparatus transmission data, using the generated encryption key to generate the encrypted measurement data (Step S308). Here, details of encryption processing on measurement data by the encryption processing unit 111 will be described later.

Next, the encryption processing unit 111 generates the measuring-apparatus-card transmission data 21 including the generated encrypted measurement data, and the model ID and data category that correspond to the encrypted measurement data (Step S309).

Next, the transmitting and receiving unit 114 transmits the measuring-apparatus card transmission data 21 to the user-terminal card 14 (Step S310). Then, the measuring-apparatus card 11a repeats the processes from Steps S301 to S310.

As described above, the measuring-apparatus card 11a generates the encrypted measurement data obtained by receiving measurement data from the measuring apparatus 10a and encrypting the received data. Furthermore, the measuring-apparatus card 11a transmits, to the user-terminal card 14, the measuring-apparatus-card transmission data 21 including the generated encrypted measurement data, the model ID that is information identifying a measuring apparatus, and the data category that is information identifying a category of health information.

Next, the details of encryption processing on transmission data by the encryption processing unit 111 (Steps S307 and 308 in FIG. 19) will be described. The encryption key generating unit 113 generates an encryption key K indicated below, using a model ID and a data category included in measuring-apparatus transmission data to be encrypted. Then, the encryption key generating unit 113 transfers the generated encryption key K to the encryption processing unit 111.

$K=F(\text{master key,model ID included in the measuring-apparatus transmission data}\|\text{data category})$ Here, F represents a one-way function. Furthermore, "C=F (A, B)" represents an expression of obtaining C as a result of calculation of the one-way function F using data A and B. Furthermore, "A∥B" represents the concatenated data of A and B. For example, when A=131313 and B=242424, A∥B=131313242424. Furthermore, the master key is obtained from the master key storage unit 112.

Next, the encryption processing unit 111 encrypts measurement data D included in the measuring-apparatus transmission data, using the encryption key K generated by the encryption key generating unit 113.

In other words, "E=Enc(K,D)" is calculated. In this case, "Enc(K,D)" represents a result of encryption on the data D using the encryption key K.

As described above, encrypted measurement data E is generated using the measurement data.

<Transferring of Encrypted Measurement Data Using User-Terminal Card 14>

Next, processing when the user-terminal card 14 transfers the encrypted measurement data received from the measuring-apparatus card 11a to a service providing server will be described.

Figure 20:
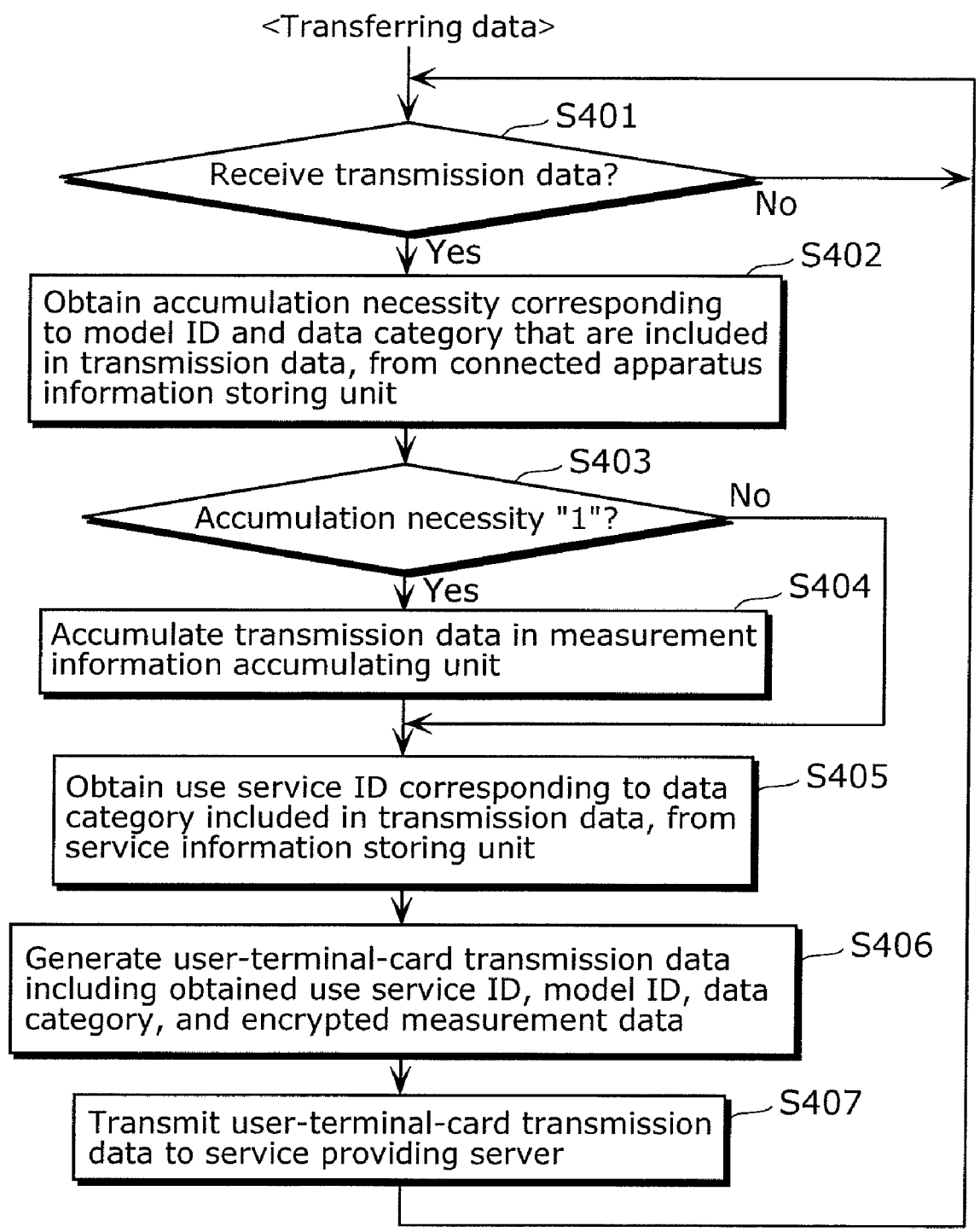
FIG. 20 shows a flowchart indicating transferring data to the user-terminal card according to the first and third embodiments.

FIG. 20 shows a flowchart indicating transferring of data to the user-terminal card 14.

First, the first transmission and receiving unit 142 judges whether or not the user-terminal card 14 has received the measuring-apparatus-card transmission data 21 from the measuring-apparatus card 11a through the internal network 12 (Step S401). Here, when the user-terminal card 14 has not received the measuring-apparatus-card transmission data 21 (No in Step S401), again, the first transmitting and receiving unit 142 judges whether or not the user-terminal card 14 has received measuring-apparatus-card transmission data 21 (Step S401). Here, when the user-terminal card 14 has received the measuring-apparatus-card transmission data 21 (Yes in Step S401), the first transmitting and receiving unit 142 obtains an accumulation necessity corresponding to the model ID and data category that are included in the measuring-apparatus-card transmission data 21 from the connected apparatus information 23 stored in the connected apparatus information storing unit 144 (Step S402).

Next, the first transmitting and receiving unit 142 judge whether or not the obtained accumulation necessity is "1" (Step S403). Here, when the obtained accumulation necessity is "1" (Yes in Step S403), the first transmitting and receiving unit 142 accumulates the measuring-apparatus-card transmission data 21 in the measurement information accumulating unit 141 (Step S404). On the other hand, when the obtained accumulation necessity is not "1" (No in Step S403), the first transmitting and receiving unit 142 proceeds to a process in Step S405 without accumulating the measuring-apparatus-card transmission data 21 in the measurement information accumulating unit 141.

More specifically, as shown in FIG. 9, the first transmitting and receiving unit 142 accumulates, for each model ID and each data category, only the encrypted measurement data having accumulation necessity data that indicates "1" and that is included in the connected apparatus information 23, as the accumulated measurement data 24 to be accumulated in the measurement information accumulating unit 141.

Next, the first transmitting and receiving unit 142 obtains a service ID corresponding to a data category included in the measuring-apparatus-card transmission data 21, from the service information 25 stored in the service information storing unit 145 (Step S405). For example, when a data category included in the measuring-apparatus-card transmission data 21 is "001", the first transmitting and receiving unit 142 obtains the service ID "0002" from the service information 25 in FIG. 10.

Next, the first transmitting and receiving unit 142 generates user-terminal-card transmission data including the service ID obtained in Step S405, the model ID and the data category that are included in the measuring-apparatus-card transmission data 21, and the encrypted measurement data (Step S406).

Then, the second transmitting and receiving unit 143 transmits the generated user-terminal-card transmission data to a service providing server identified by a service ID (Step S407). Here, the second transmitting and receiving unit 143 may transmit the accumulated measurement data 24 accumulated in the measurement information accumulating unit 141 to a service providing server on a regular basis.

For example, the user-terminal card 14 transmits health information having the data category "001" (body weight) and the data category "004" (blood pressure) to the first service providing server 17a identified by the service ID "0002" by referring to the service information 25 in FIG. 10. More specifically, the user-terminal card 14 obtains data sets (each combination of a model ID, a data category, and encrypted measurement data) respectively corresponding to the data categories "001" and "004, from the accumulated measurement data 24 accumulated in the measurement information accumulating unit 141. Then, the user-terminal card 14 transmits the obtained data sets to the first service providing server 17a as the user-terminal-card transmission data.

<Decrypting Encrypted Measurement Data Using First Service Providing Server 17a>

Next, described is judging whether or not to decrypt encrypted measurement data included in the received user-terminal-card transmission data and decrypting the encrypted measurement data, using the first service providing server 17a.

Figure 21:
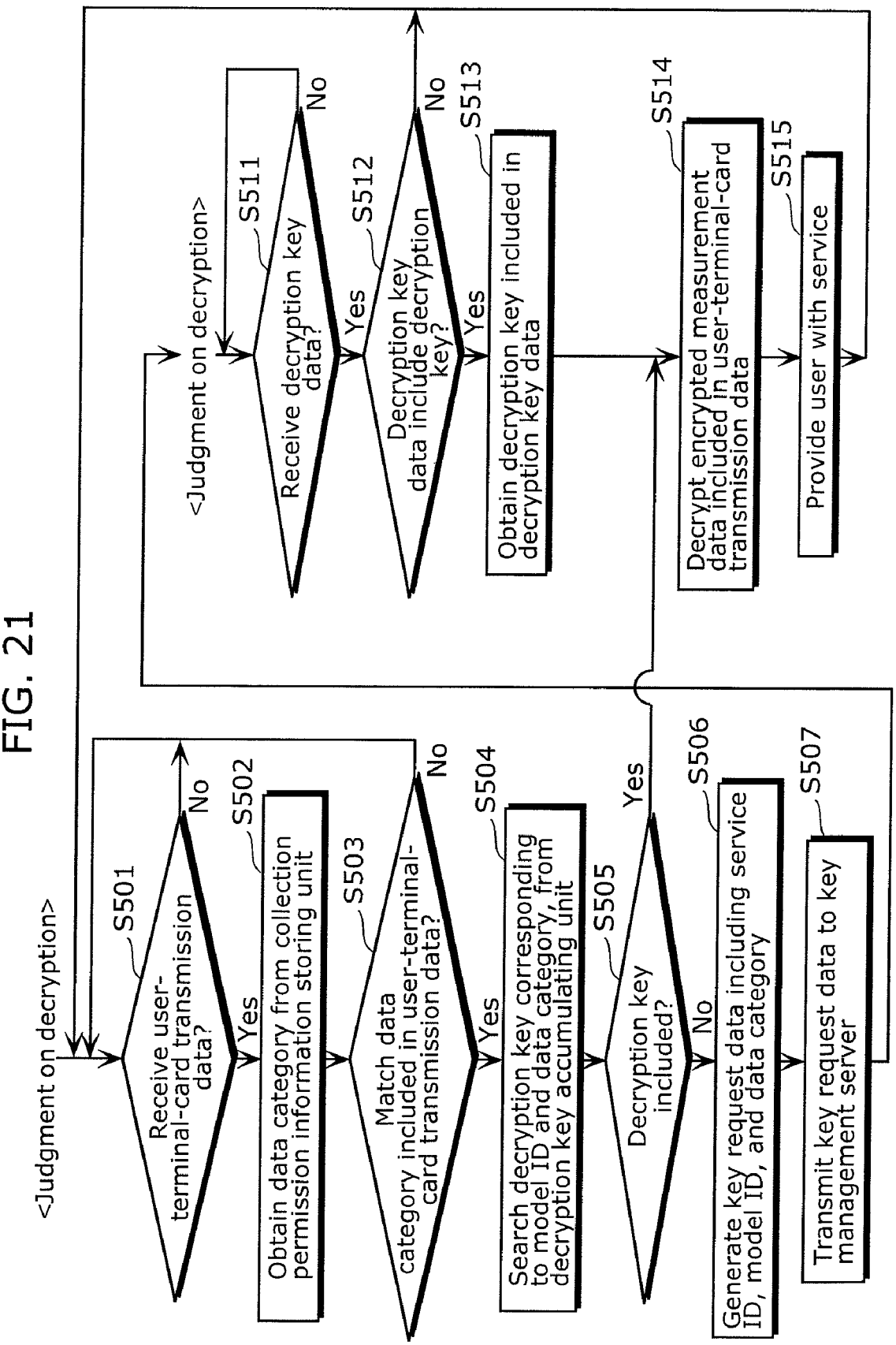
FIG. 21 shows a flowchart indicating judgment on decryption and the decryption by the first service providing server according to the first and third embodiments.

FIG. 21 shows a flowchart indicating judgment on the decryption and the decryption by the first service providing server 17a. First, the judgment of decryption by the first service providing server 17a will be described.

The transmitting and receiving unit 171 judges whether or not the first service providing server 17a has received user-terminal-card transmission data from the user-terminal card 14 through the external network 15 (Step S501). Here, when the first service providing server 17a has not received the user-terminal-card transmission data (No in Step S501), again, the transmitting and receiving unit 171 judges whether or not the first service providing server 17a has received user-terminal-card transmission data (Step S501). On the other hand, when the first service providing server 17a has received the user-terminal-card transmission data (Yes in Step S501), the transmitting and receiving unit 171 obtains a data category that is stored in the collection permission information storing unit 170 and is included in the collection permission information 26 (Step S502). The transmitting and receiving unit 171 obtains, for example, the data categories "001" and "004" from the collection permission information 26 shown in FIG. 12.

Next, the transmitting and receiving unit 171 judges whether or not the data category included in the received user-terminal-card transmission data matches the data category obtained in Step S502 (Step S503). Here, when the data categories do not match (No in Step S503), the transmitting and receiving unit 171 judges that the encrypted measurement data is not decrypted, and again judges whether or not the first service providing server 17a has received user-terminal-card transmission data (Step S501). On the other hand, when the data categories match (Yes in Step S503), the transmitting and receiving unit 171 searches the accumulated decryption key data 28 accumulated in the decryption key accumulating unit 176, for a decryption key corresponding to the model ID and data category included in the user-terminal-card transmission data (Step S504).

As a result of the search in Step S504, when the accumulated decryption key data 28 includes a decryption key corresponding to the model ID and data category included in the user-terminal-card transmission data (Yes in Step S505), the measurement data decrypting unit 173 decrypts the encrypted measurement data included in the user-terminal-card transmission data, using the decryption key (Step S514). On the other hand, when the accumulated decryption key data 28 does not include a decryption key corresponding to the model ID and data category included in the user-terminal-card transmission data (No in Step S505), the key request data generating unit 172 generates the key request data 27 including the service ID for identifying the first service providing server 17a, and the model ID and the data category included in the user-terminal-card transmission data (Step S506).

Next, the transmitting and receiving unit 171 transmits the key request data 27 to the key management server 16 through the external network 15 (Step S507).

As described above, the transmitting and receiving unit 171 included in the first service providing server 17a checks whether or not the first service providing server 17a is authorized to retrieve a data category from the user-terminal-card transmission data, refer to the collection permission information 26 stored in the collection permission information storing unit 170, and decrypt the encrypted measurement data included in the received user-terminal-card transmission data. The transmitting and receiving unit 171 of the first service providing server 17a, for example, judges that the first service providing server 17a can collect health information having the data categories "001" (body weight) and "004"

(blood pressure) by referring to the collection permission information 26 shown in FIG. 12. In other words, when the received user-terminal-card transmission data includes the health information having the data categories "001" (body weight) and "004" (blood pressure), the transmitting and receiving unit 171 of the first service providing server 17a judges that the first service providing server 17a is authorized to decrypt such health information and collect the decrypted health information.

As described above, the transmitting and receiving unit 171 checks that the first service providing server 17a is authorized to decrypt the encrypted measurement data included in the received user-terminal-card transmission data. Then, the key request data generating unit 172 generates key request data using a model ID and a data category that are included in the user-terminal-card transmission data, and the service ID of the first service providing server 17a. In other words, a service ID of a service providing server that generates key request data is added to the key request data. For example, the service ID "0002" of the first service providing server 17a is added to the key request data 27 shown in FIG. 13. The model ID and the data category included in the user-terminal-card transmission data are copied to the key request data 27. The transmitting and receiving unit 171 transmits the generated key request data 27 to the key management server 16.

Next, the decryption by the first service providing server 17a will be described.

First, the transmitting and receiving unit 171 judges whether or not the first service providing server 17a has received decryption key data from the key management server 16 through the external network 15 (Step S511). Here, when the first service providing server 17a has not received the decryption key data (No in Step S511), again, the transmitting and receiving unit 171 judges whether or not the first service providing server 17a has received decryption key data (Step S511). On the other hand, when the first service providing server 17a has received the decryption key data (Yes in Step S511), the transmitting and receiving unit 171 judges whether or not the decryption key data includes a decryption key (Step S512).

Here, when the decryption key data does not include a decryption key (No in Step S512), the transmitting and receiving unit 171 again judges whether or not the first service providing server 17a has received decryption key data (Step S511). On the other hand, when the decryption key data includes a decryption key (Yes in Step S512), the measurement data decrypting unit 173 obtains the decryption key included in the decryption key data (Step S513).

Next, the measurement data decrypting unit 173 decrypts the encrypted measurement data included in the user-terminal-card transmission data, using the obtained decryption key (Step S514). More specifically, the measurement data decrypting unit 173 decrypts encrypted measurement data E using a decryption key K as expressed by a following equation.

$$D=Dec(K,E)$$

Next, the measurement data using unit 175 provides the user with a service using the measurement data decrypted by the measurement data decrypting unit 173 (Step S515). More specifically, the measurement data using unit 175 accumulates the decrypted measurement data D obtained from the equation, in the user measurement data accumulating unit 174 for each user. Then, the measurement data using unit 175 provides a user with a service, such as health advice, based on the accumulated measurement data.

Then, the first service providing server 17a repeats the processes from Steps S501 to S515.

As described above, the first service providing server 17a requests the transmission of a decryption key for decrypting measurement data from the key management server 16. Furthermore, the first service providing server 17a decrypts the measurement data using the decryption key obtained from the key management server 16.

<Generating a Decryption Key by Key Management Server 16>

Next, the generating of a decryption key using the received key request data 27 by the key management server 16 will be described.

Figure 22:
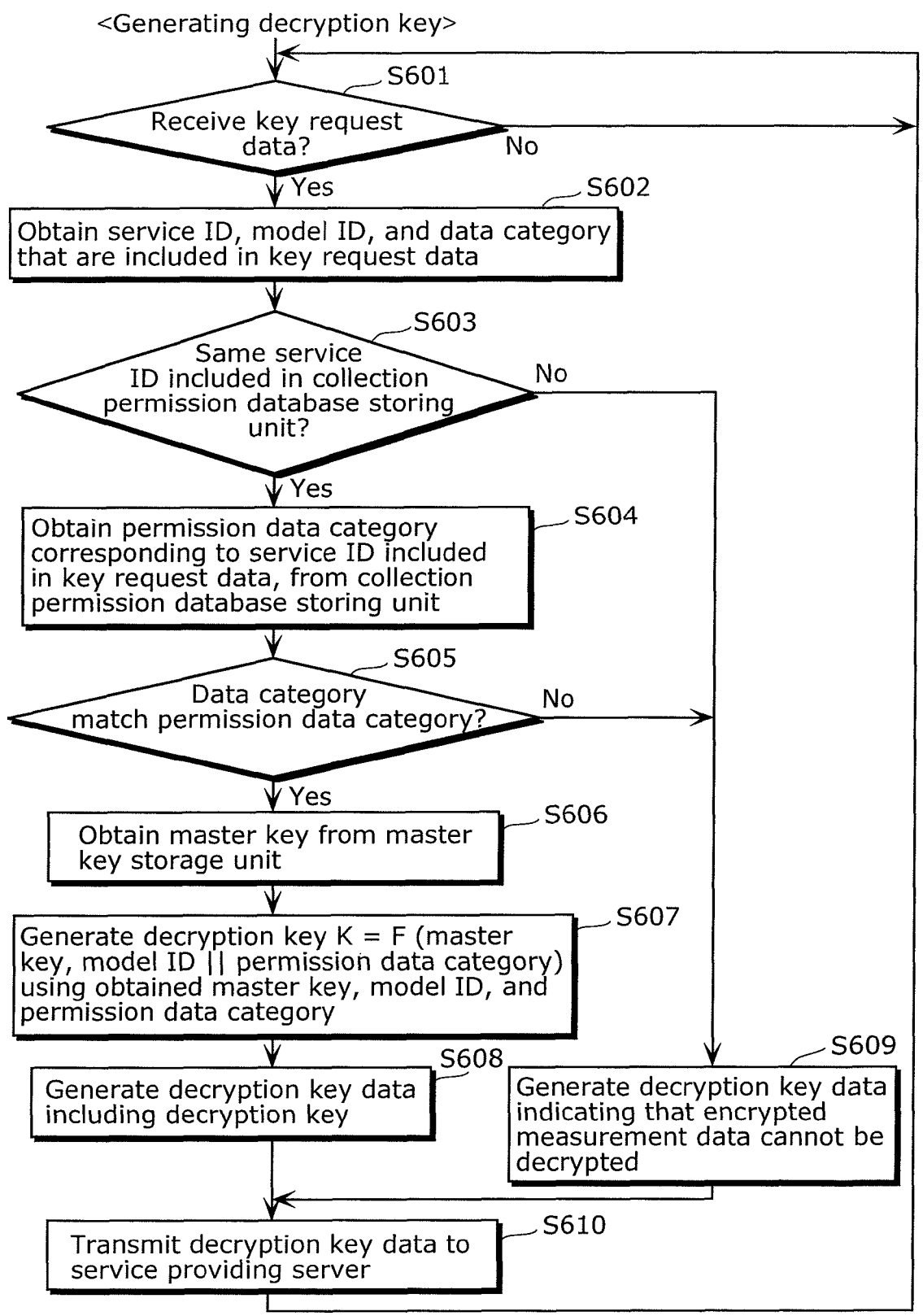
FIG. 22 shows a flowchart indicating generating of a decryption key by the key management server according to the first embodiment.

FIG. 22 shows a flowchart indicating generating of a decryption key by the key management server 16.

First, the transmitting and receiving unit 161 judges whether or not the key management server 16 has received the key request data 27 from a service providing server through the external network 15 (Step S601). Here, when the first service providing server 17a has not received the key request data 27 (No in Step S601), again, the transmitting and receiving unit 161 judges whether or not the key management server 16 has received the key request data 27 (Step S601). On the other hand, when the key management server 16 has received the key request data 27 (Yes in Step S601), the decryption key generation-permission judging unit 163 obtains the service ID, the model IDs, and the data categories that are included in the key request data 27 (Step S602).

Next, the decryption key generation-permission judging unit 163 judges whether or not the key request data 27 is valid.

In other words, the decryption key generation-permission judging unit 163 first judges whether or not the service ID included in the key request data 27 is also included in the collection permission database 29 stored in the collection permission database storing unit 164 (Step S603). Here, when the service ID is not included in the collection permission database 29 (No in Step S603), the decryption key generating unit 163 generates decryption key data indicating that a service providing server that has transmitted the key request data 27 cannot decrypt encrypted measurement data (cannot decrypt) (Step S609). Here, when the service ID is included in the collection permission database 29 (Yes in Step S603), the decryption key generating unit 163 obtains, from the collection permission database 29, a permission data category corresponding to the service ID included in the key request data 27 (Step S604).

Next, the decryption key generation-permission judging unit 163 judges whether or not the data category included in the key request data 27 matches the permission data category obtained in Step S604 (Step S605). Here, when the data category does not match the permission data category (No in Step S605), the decryption key generating unit 162 generates decryption key data indicating that a service providing server that has transmitted the key request data 27 cannot decrypt encrypted measurement data (cannot decrypt) (Step S609). On the other hand, when the data category matches the permission data category (Yes in Step S605), the decryption key generating unit 162 obtains a master key stored in the master key storage unit 160 (Step S606).

For example, since the key request data 27 in FIG. 13 includes the service ID "0002", the permission data categories "001" and "004" can be obtained by searching the collection permission database 29 shown in FIG. 16. On the other hand, the accumulated decryption key data 28 includes both of the data categories "001" and "004" that are the categories obtained as a result of the search. Thus, the decryption key generation-permission judging unit 163 generates decryption key generation-permission data as follows, and notifies the decryption key generating unit 162.

Decryption key generating permission data=(permission data category,model ID)=(001, 12345678) and (004, 2468912)

Next, the decryption key generating unit 162 generates a decryption key using the model ID, the data category, and the master key (Step S607). More specifically, the decryption key generating unit 162 generates a decryption key K based on the received decryption key generation-permission data according to a following equation. Here, data stored in the master key storage unit 160 is used as a master key.

$K=F$(master key,model ID included in the decryption key generation-permission data||permission data category)

For example, the decryption key K corresponding to the permission data category "004" may be calculated using a following equation.

$K=F$(master key,2468912||004)

Next, the decryption key generating unit 162 generates decryption key data including the generated decryption key (Step S608).

Then, the transmitting and receiving unit 161 transmits the decryption key data generated in Steps S608 and S609 to a service providing server (Step S610). The transmitting and receiving unit 161 transmits, for example, the decryption key K calculated in the aforementioned manner to the first service providing server 17*a*.

Then, the key management server 16 repeats the processes from Steps S601 to S610.

As described above, with the health care system 1 according to the first embodiment, the number of encryption processing in a measuring apparatus does not increase even when a health service to be used increases. In other words, the encryption processing is performed once per health information regardless of the number of health care services to be used. Accordingly, the first embodiment can achieve the health care system in which encryption processing in a measuring apparatus does not increase with an additional service to be used.

Furthermore, the health care system 1 according to the first embodiment includes the key management server 16 that transmits a decryption key for decrypting predetermined encrypted measurement data only to a service providing server to be a destination of the measurement data. Thus, when a measuring-apparatus card (for example, the measuring-apparatus card 11*a*) encrypts measurement data obtained by a measuring apparatus (for example, the measuring apparatus 10*a*) using a predetermined encryption key, there is no need to change a category of an encryption key to be used to encrypt measurement data according to a service providing server that is the final destination of the data. In other words, as long as a measuring-apparatus card encrypts data using a shared encryption key to transmit the data, only a service providing server selected by the key management server 16 can decrypt the encrypted measurement data using the shared decryption key. As a result, the health care system 1 of the first embodiment can eliminate encryption processing for encrypting measurement data using different encryption keys according to a category of each server that provides a service.

Furthermore, upon receipt of the key request data 27 from a service providing server (for example, the first service providing server 17*a*), the key management server 16 judges whether or not a data category and a service ID included in the key request data 27 match a data category and a service ID included in the collection permission database 29 stored in the collection permission database storing unit 164. When they match each other, the key management server 16 transmits a decryption key to the corresponding service providing server. Thereby, since the key management server 16 has only to store, in the collection permission database storing unit 164, a table (collection permission database 29) showing correspondence between data categories and service IDs, the number of tables held by the key management server 16 can be reduced.

Furthermore, the measuring-apparatus card (for example, the measuring-apparatus card 11*a*) and the key management server 16 generate a predetermined encryption key and a decryption key corresponding to the predetermined encryption key, using a shared master key. Thus, when the measuring-apparatus card passes a model ID for identifying a measuring apparatus to a service providing server (for example, the first service providing server 17*a*), and the service providing server passes the model ID to the key management server 16, the key management server 16 can generate a decryption key corresponding to the predetermined encryption key, without transmitting the master key itself through any communication path. Thereby, the health care system 1 of the first embodiment can ensure confidentiality of a decryption key.

Furthermore, since a measuring-apparatus card (for example, the measuring-apparatus card 11*a*) attached to a measuring apparatus (for example, the measuring apparatus 10*a*) includes the encryption key generating unit 113, the encryption processing unit 111, and the master key storage unit 112, there is no need to add substantially, to the measuring apparatus itself, any constituent elements unnecessary for obtaining data through measurement. In other words, since a measuring-apparatus card can generate a predetermined encryption key, generate encrypted measurement data using the generated encryption key, and transmit the generated encrypted vital sign data, the health care system 1 of the first embodiment can provide a service related to health while simplifying the configuration of the measuring apparatus.

Second Embodiment

Next, a health care system according to a second embodiment with reference to drawings will be described.

The health care system 1 according to the second embodiment differs from that of the first embodiment in excluding any data category from measuring-apparatus card transmission data and key request data, and in that a key management server judges whether or not to permit generating of a decryption key using model information database indicating a relationship between a model ID and a data category. Hereinafter, such differences will be mainly described in the second embodiment by omitting points similar to the illustration and description used in the first embodiment.

The entire configuration of the health care system 1 of the second embodiment and the functional configuration of the measuring apparatus 10*a* are the same as those of the first embodiment, and thus the illustration and description are omitted.

<Configurations of Measuring-Apparatus Cards 11*a*, 11*b*, and 11*c*>

(Encryption Processing Unit 111)

Figure 23:
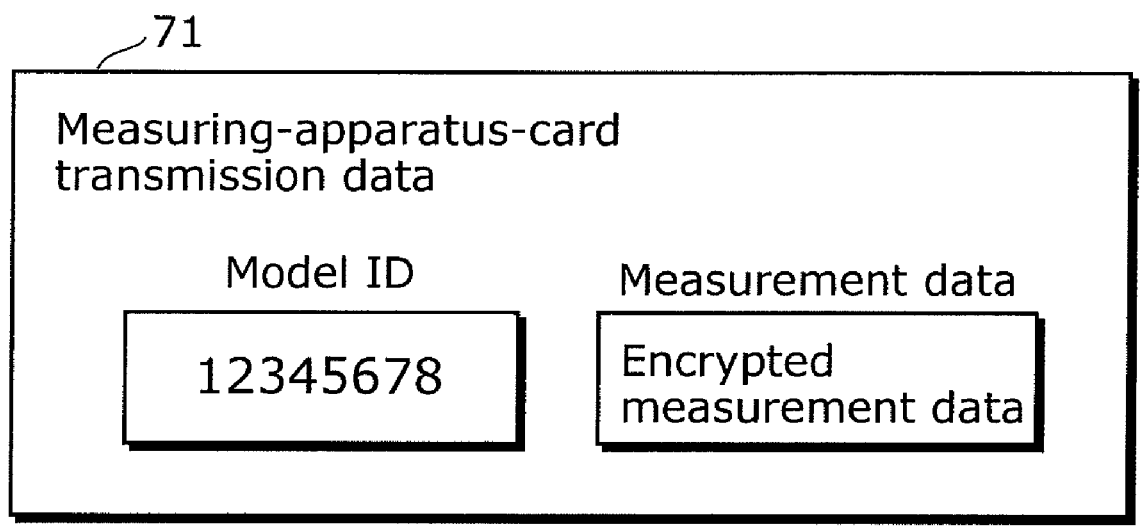
FIG. 23 shows an example of measuring-apparatus-card transmission data according to the second embodiment.

The encryption processing unit 111 is an example of an encrypting unit, and generates encrypted measurement data obtained by receiving measurement data from the measuring apparatus 10a and encrypting the received measurement data using an encryption key generated by the encryption key generating unit 113. Furthermore, the encryption processing unit 111 generates measuring-apparatus-card transmission data 71 including a model ID and encrypted measurement data. FIG. 23 illustrates an example of the measuring-apparatus-card transmission data 71. The measuring-apparatus-card transmission data 71 includes encrypted measurement data and the model ID of the measuring apparatus 10a to which the measuring-apparatus card 11a is attached. In other words, the measuring-apparatus-card transmission data 71 does not include any data category that is included in the measuring-apparatus-card transmission data 21 of the first embodiment.

(Measuring-Apparatus Information Storing Unit 116)

Measuring-apparatus information 72 is stored in the measuring-apparatus information storing unit 116. The measuring-apparatus information 72 includes information regarding the measuring apparatus 10a to which the measuring-apparatus card 11a is attached, and information set according to an instruction from the user-terminal card 14. FIG. 24 illustrates an example of the measuring-apparatus information 72. In the measuring-apparatus information 72, data of transmission necessity is set so as to indicate that only one data category needs to be transmitted. For example, as shown in FIG. 24, only the transmission necessity of the data category "001" is set to 1. Thereby, the encryption processing unit 111 encrypts only measurement data of one data category.

<Configuration of User-Terminal Card 14>

(Connected Apparatus Information Storing Unit 144)

Connected apparatus information 73 is stored in the connected apparatus information storing unit 144. The connected apparatus information 73 includes information identifying a measuring-apparatus card connected to the user-terminal card 14, information of a measuring apparatus to which the measuring-apparatus card is attached, and information of whether or not health information obtained by the measuring apparatus needs to be accumulated. FIG. 25 illustrates an example of the connected apparatus information 73. As shown in FIG. 25, the connected apparatus information 73 includes measuring-apparatus card IDs, model IDs, and accumulation necessities. In other words, the connected apparatus information 73 excludes any data category included in the connected apparatus information 23 of the first embodiment.

<Configurations of First Service Providing Server 17a, Second Service Providing Server 17b, and Third Service Providing Server 17c>

(Key Request Data Generating Unit 172)

Figure 26:
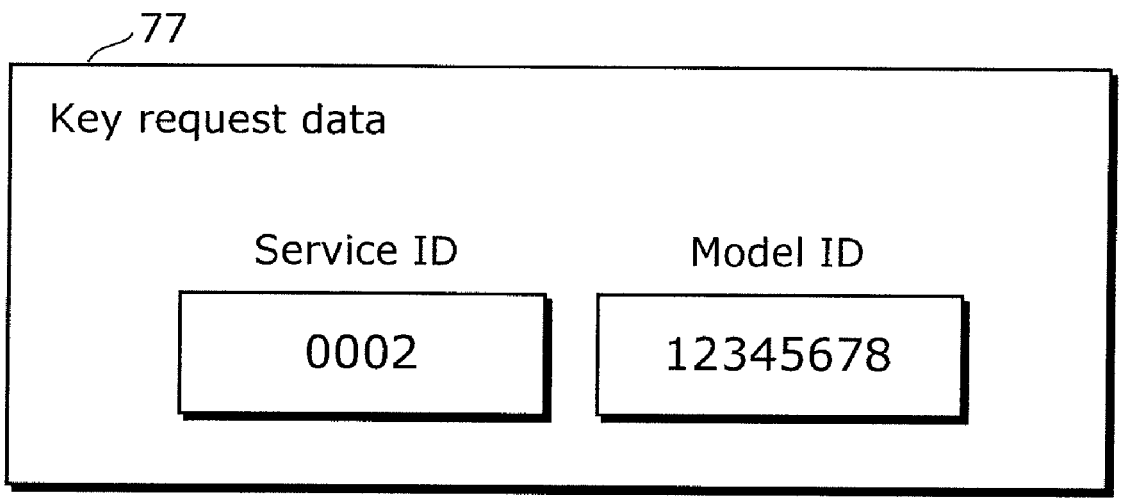
FIG. 26 shows an example of key request data according to the second embodiment.

The key request data generating unit 172 generates key request data 77 for requesting the key management server 16 to transmit a decryption key for decrypting the encrypted measurement data received from the user-terminal card 14. The key request data 77 includes information identifying a measuring apparatus and information identifying a service providing server. FIG. 26 illustrates an example of the key request data 77. As in FIG. 26, the key request data 77 of the second embodiment includes a service ID of a service providing server and a model ID included in user-terminal-card transmission data. In other words, the key request data 77 excludes any data category included in the key request data 27 of the first embodiment.

(Decryption Key Accumulating Unit 176)

Figure 27:
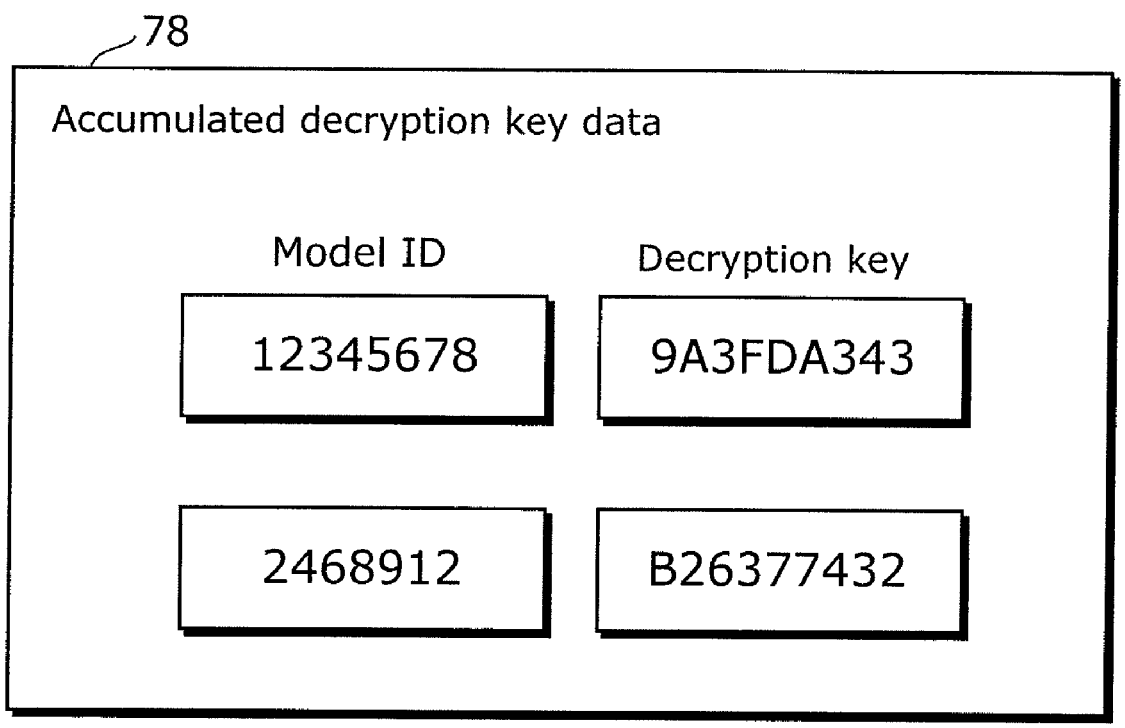
FIG. 27 shows an example of accumulated decryption key data according to the second embodiment.

The decryption key accumulating unit 176 accumulates a decryption key received from the key management server 16. FIG. 27 illustrates an example of accumulated decryption key data 78 accumulated by the decryption key accumulating unit 176. As shown in FIG. 27, the accumulated decryption key data 78 of the second embodiment includes model IDs and decryption keys. In other words, the accumulated decryption key data 78 excludes any data category included in the accumulated decryption key data 28 of the first embodiment.

<Configuration of Key Management Server 16>

Figure 28:
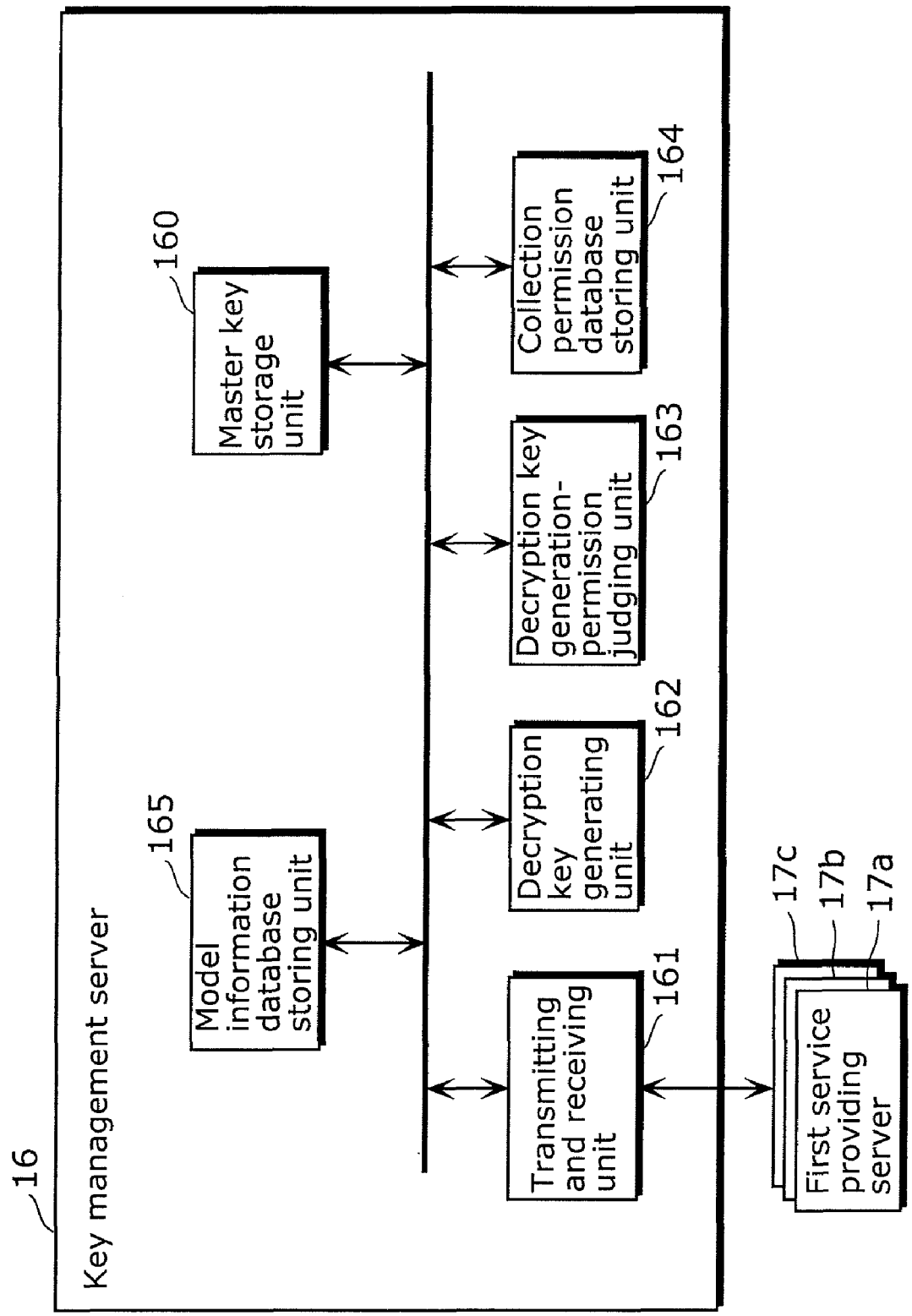
FIG. 28 illustrates a block diagram of a functional configuration of the key management server according to the second embodiment.

FIG. 28 schematically illustrates a functional configuration of the key management server 16. As illustrated in FIG. 28, the key management server 16 of the second embodiment additionally includes a model information database storing unit 165 besides the constituent elements of the key management server 16 of the first embodiment.

(Decryption Key Generation-Permission Judging Unit 163)

The decryption key generation-permission judging unit 163 is an example of a control unit, and judges whether or not a decryption key is generated, using the collection permission database 29 stored in the collection permission database storing unit 164 and a model information database 80 stored in the model information database storing unit 165, in response to a decryption key request from a service providing server. When judging that a decryption key is generated, the decryption key generation-permission judging unit 163 instructs the decryption key generating unit 162 and the transmission and receiving unit 161 to generate the decryption key and transmit the generated decryption key.

(Collection Permission Database Storing Unit 164)

The collection permission database 29 is stored in the collection permission database storing unit 164. The collection permission database 29 stores data categories of health information that each of the service providing servers is permitted to collect.

(Model Information Database Storing Unit 165)

Figure 29:
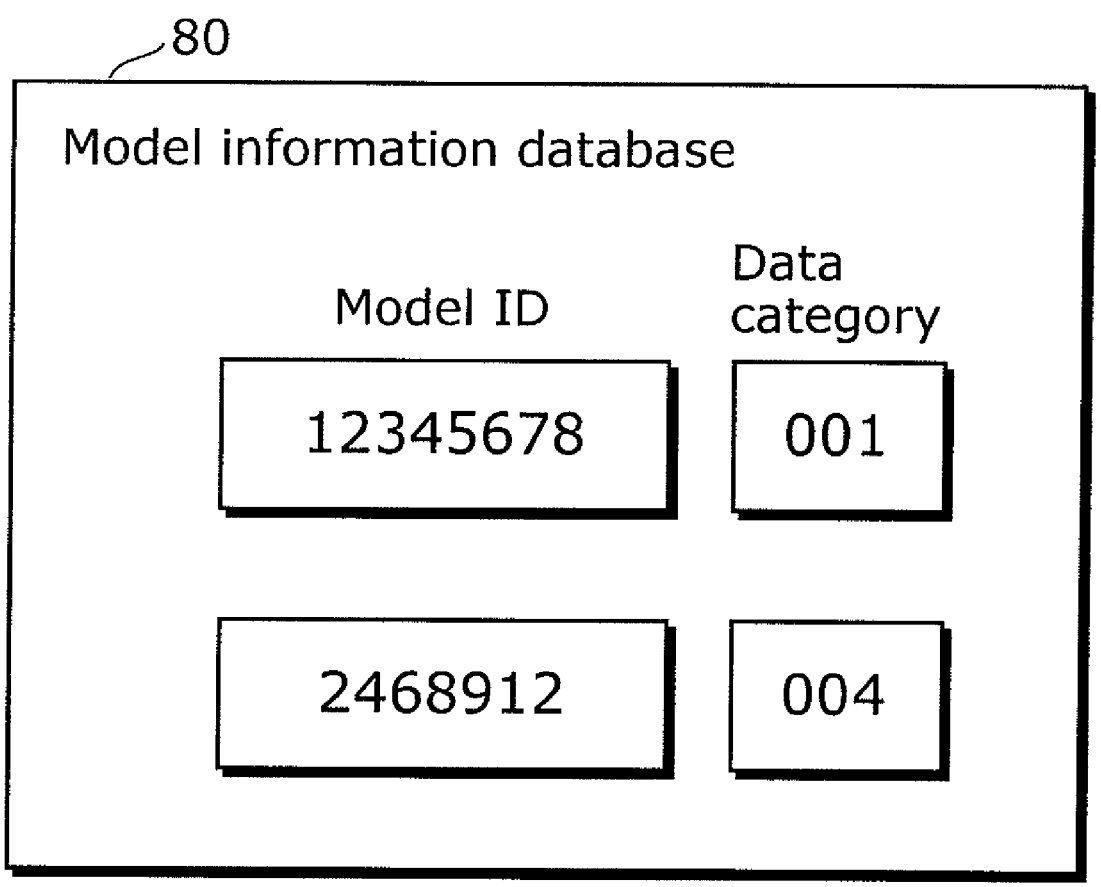
FIG. 29 shows an example of a model information database according to the second embodiment.

The model information database 80 is stored in the model information database storing unit 165. The categories of health information that is obtained by a measuring apparatus in correspondence with information identifying a measuring apparatus are stored in the model information database 80. FIG. 29 illustrates an example of the model information database 80. As shown in FIG. 29, the model IDs and data categories are stored in the model information database 80. For example, the data category corresponding to a measuring apparatus having the model ID "12345678" is "001" (body weight) in the model information database 80.

Next, various operations of the health care system 1 of the second embodiment having the aforementioned configuration will be described.

Since sequences of entire processing of the health care system 1 according to the second embodiment are the same as those of the first embodiment in FIG. 17, the illustration is omitted. The entire processing of the health care system 1 according to the second embodiment will be described using FIG. 17.

First, the measuring apparatus 10a measures the user for health information. Then, the measuring apparatus 10a transmits, to the measuring-apparatus card 11a, measuring apparatus transmission data including a model ID, a data category, and measurement data (Step S101).

Next, the measuring-apparatus card 11a encrypts the measurement data included in the received measuring apparatus transmission data. Then, the measuring-apparatus card 11a transmits, to the user-terminal card 14, the measuring-apparatus-card transmission data 71 including the model ID and the encrypted measurement data (Step S102).

Next, the user-terminal card 14 identifies a service ID corresponding to the model ID included in the measuring-apparatus-card transmission data 71. Then, the user-terminal card 14 transfers, to a service providing server corresponding to the identified service ID (here, the first service providing server 17a), the user-terminal card transmission data including the encrypted measurement data corresponding to the model ID (Step S103).

Next, the first service providing server 17a judges whether or not to decrypt the encrypted measurement data. When judging that the measurement data is decrypted, the first service providing server 17a transmits, to the key management server 16, the key request data 77 including the service ID indicating the server and the model ID included in the received user-terminal card transmission data (Step S104).

Next, the key management server 16 generates a decryption key corresponding to the key request data 77 when the received key request data 77 satisfies a predetermined condition, and transmits decryption key data including the generated decryption key to the first service providing server 17a (Step S105).

Next, the first service providing server 17a decrypts the encrypted measurement data using the decryption key included in the received decryption key data (Step S106).

As described above, the health care system 1 of the second embodiment excludes any data category in the key request data 77 and in the measuring-apparatus card transmission data 71.

Next, detailed operations of the measuring-apparatus card 11a, the user-terminal card 14, the first service providing server 17a, and the key management server 16 will be described. Here, since the operations in the measuring apparatus 10a of the second embodiment are the same as those of the first embodiment, thus the description is omitted. Furthermore, steps in flowcharts of the second embodiment are similarly numbered as those of the first embodiment, and the description is omitted.

<Encrypting and Transmitting of Measurement Data Using Measuring-Apparatus Card 11a>

Processing of the measuring-apparatus card 11a that encrypts measurement data obtained by the measuring apparatus 10a and transmits the encrypted measurement data will be described.

Figure 30:
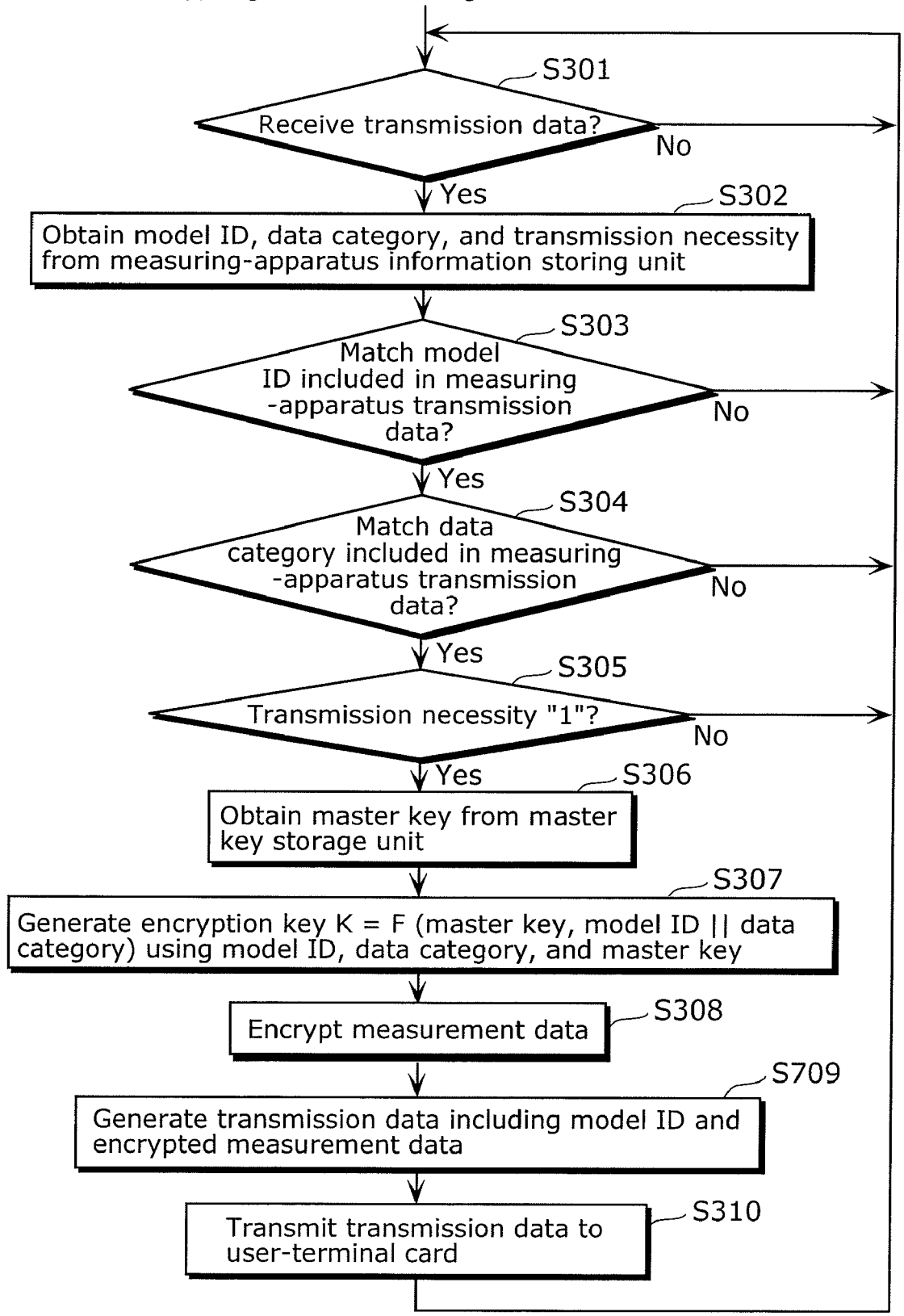
FIG. 30 shows a flowchart indicating encrypting and transmitting measurement data using the measuring-apparatus card according to the second embodiment.

FIG. 30 shows a flowchart indicating the encrypting and transmitting of measurement data using the measuring-apparatus card 11a.

The measuring-apparatus card 11a performs processes in Step S301 to S308 in the same manner as the measuring-apparatus card 11a of the first embodiment. Then, the encryption processing unit 111 generates the generated encrypted measurement data and measuring-apparatus card transmission data including a model ID corresponding to the encrypted measurement data (Step S709).

Next, the transmitting and receiving unit 114 transmits the measuring-apparatus card transmission data 71 to the user-terminal card 14 (Step S310).

<Transfer of Encrypted Measurement Data Using User-Terminal Card 14>

Next, processing when the user-terminal card 14 transfers the encrypted measurement data received from the measuring-apparatus card 11a to a service providing server will be described.

Figure 31:
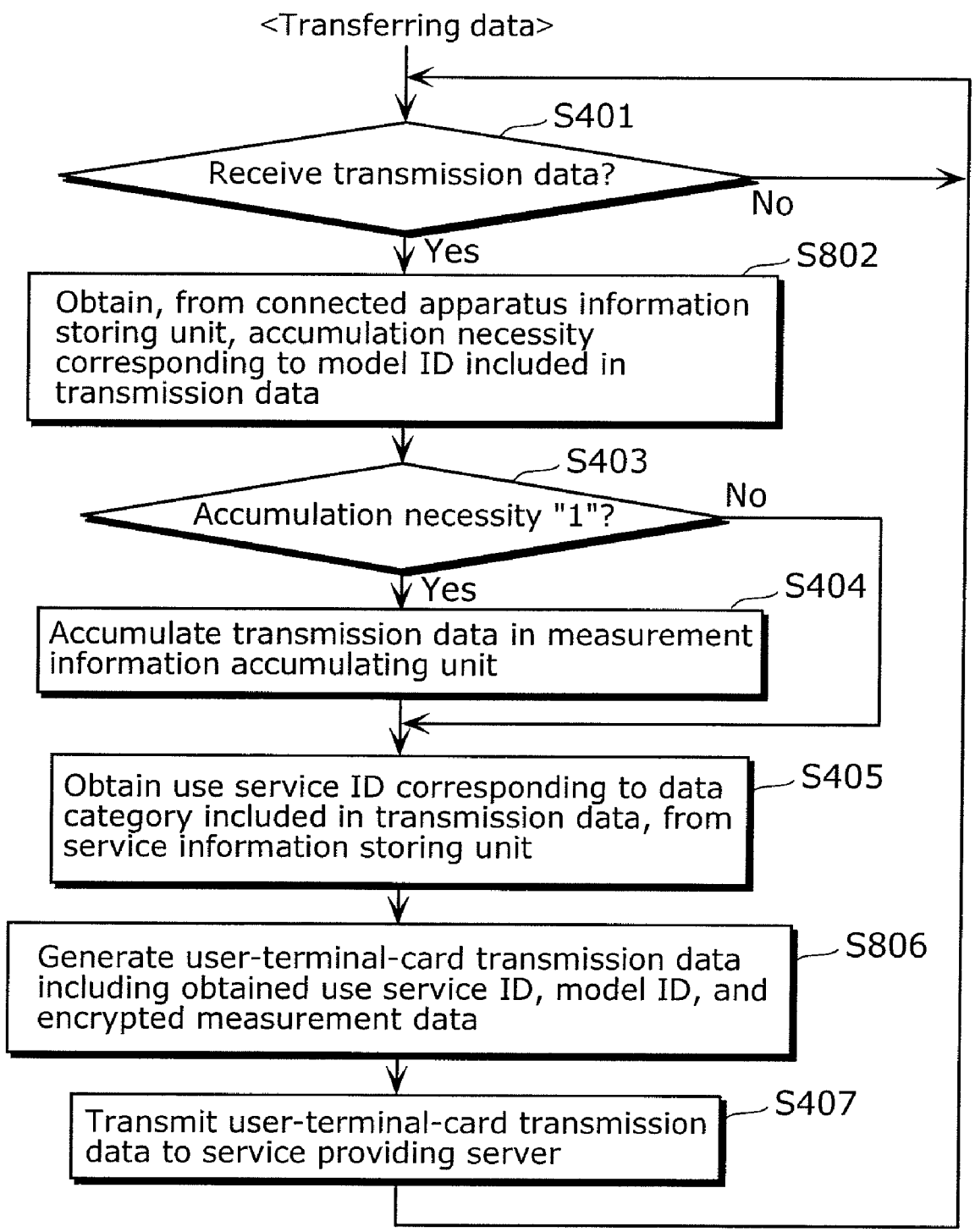
FIG. 31 shows a flowchart indicating transferring data to the user-terminal card according to the second embodiment.

FIG. 31 shows a flowchart indicating transferring of data to the user-terminal card 14.

First, the first transmission and receiving unit 142 judges whether or not the user-terminal card 14 has received the measuring-apparatus card transmission data 71 from the measuring-apparatus card 11a through the internal network 12, as the first transmitting and receiving unit 142 of the first embodiment (Step S401). Here, when the user-terminal card 14 has not received the measuring-apparatus card transmission data 71 (No in Step S401), again, the first transmitting and receiving unit 142 judges whether or not the user-terminal card 14 has received measuring-apparatus card transmission data 71 (Step S401). Here, when the user-terminal card 14 has received the measuring-apparatus card transmission data 71 (Yes in Step S401), the first transmitting and receiving unit 142 obtains an accumulation requirement corresponding to the model ID included in the measuring-apparatus card transmission data 71 from the connected apparatus information 23 stored in the connected apparatus information storing unit 144 (Step S802).

Next, the user-terminal card 14 performs processes in Step S403 to S405 in the same manner as the user-terminal card 11a of the first embodiment.

Next, the first transmitting and receiving unit 142 generates user-terminal card transmission data including the service ID obtained in Step S405, the model ID included in the measuring-apparatus card transmission data 71, and the encrypted measurement data (Step S806).

Then, the second transmitting and receiving unit 143 transmits the generated user-terminal card transmission data to a service providing server corresponding to a service ID (Step S407).

<Decrypting Encrypted Measurement Data Using First Service Providing Server 17a>

Next, described is judging whether or not to decrypt encrypted measurement data included in the received user-terminal card transmission data and decrypting the encrypted measurement data using the first service providing server 17a.

Figure 32:
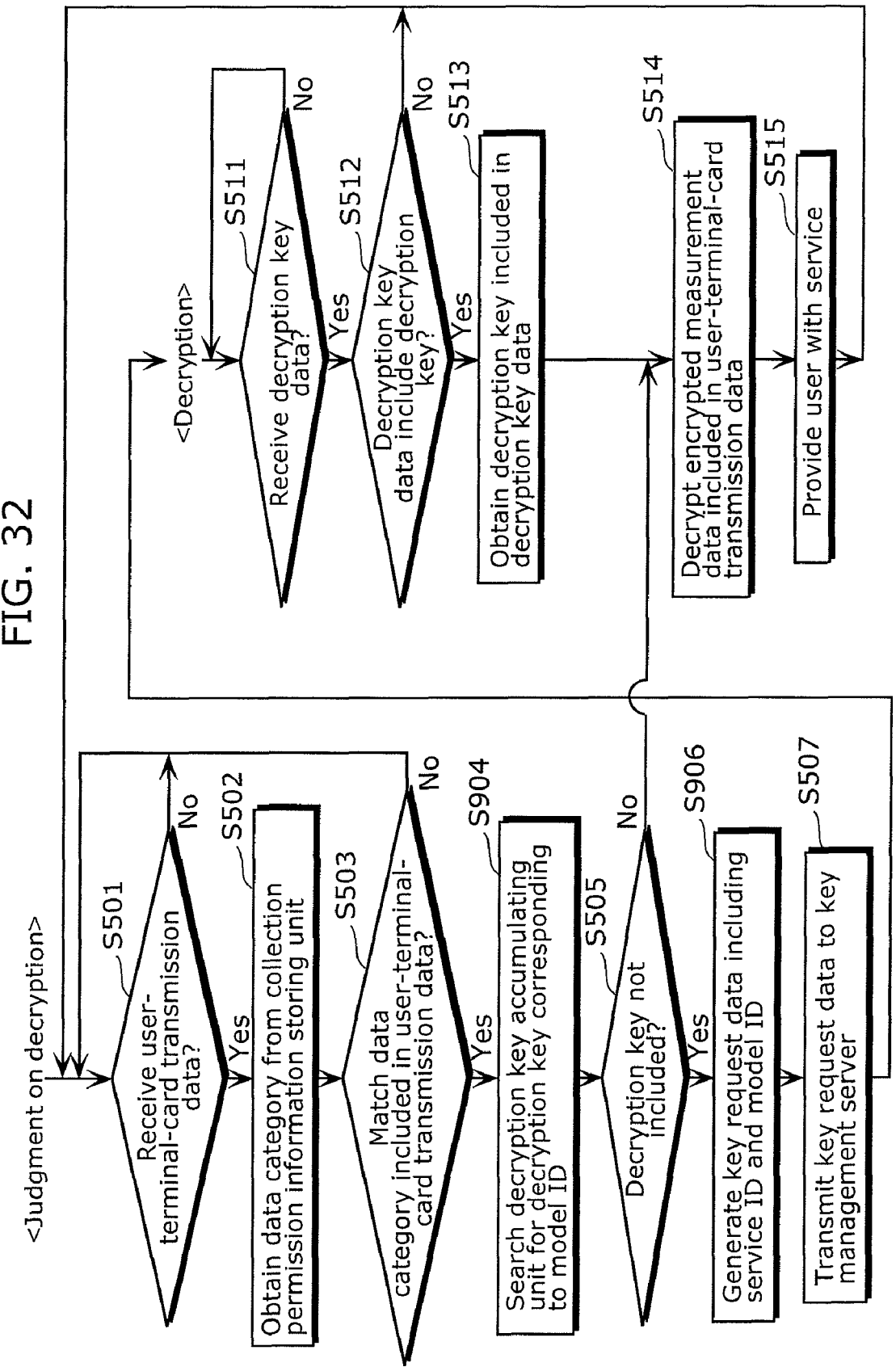
FIG. 32 shows a flowchart indicating judgment on decryption and the decryption by the first service providing server according to the second embodiment.

FIG. 32 shows a flowchart indicating judgment on decryption and the decryption by the first service providing server 17a. Since the encrypted measurement data is decrypted in the same manner as the first embodiment, judgment on the decryption by the first service providing server 17a will be described.

The first service providing server 17a performs the processes Step S501 to S503 as the first service providing server 17a of the first embodiment.

Next, the transmitting and receiving unit 171 searches the accumulated decryption key data 78 accumulated in the decryption key accumulating unit 176 for a decryption key corresponding to the model ID included in the user-terminal card transmission data (Step S904).

As a result of the search in Step S904, when the accumulated decryption key data 78 includes a decryption key corresponding to the model ID included in the user-terminal card transmission data (Yes in Step S505), the measurement data decrypting unit 173 decrypts the encrypted measurement data included in the user-terminal card transmission data, using the decryption key (Step S514). On the other hand, when the accumulated decryption key data 28 does not include a decryption key corresponding to the model ID included in the user-terminal card transmission data (No in Step S505), the key request data generating unit 172 generates the key request data 77 including a service ID for identifying the first service providing server 17a and the model ID included in the user-terminal card transmission data (Step S906).

Next, the transmitting and receiving unit 171 transmits the key request data 77 to the key management server 16 through the external network 15 (Step S507).

<Generating Decryption Key by Key Management Server 16>

Next, the generating of a decryption key by the key management server 16 using the received key request data 77 will be described.

Figure 33:
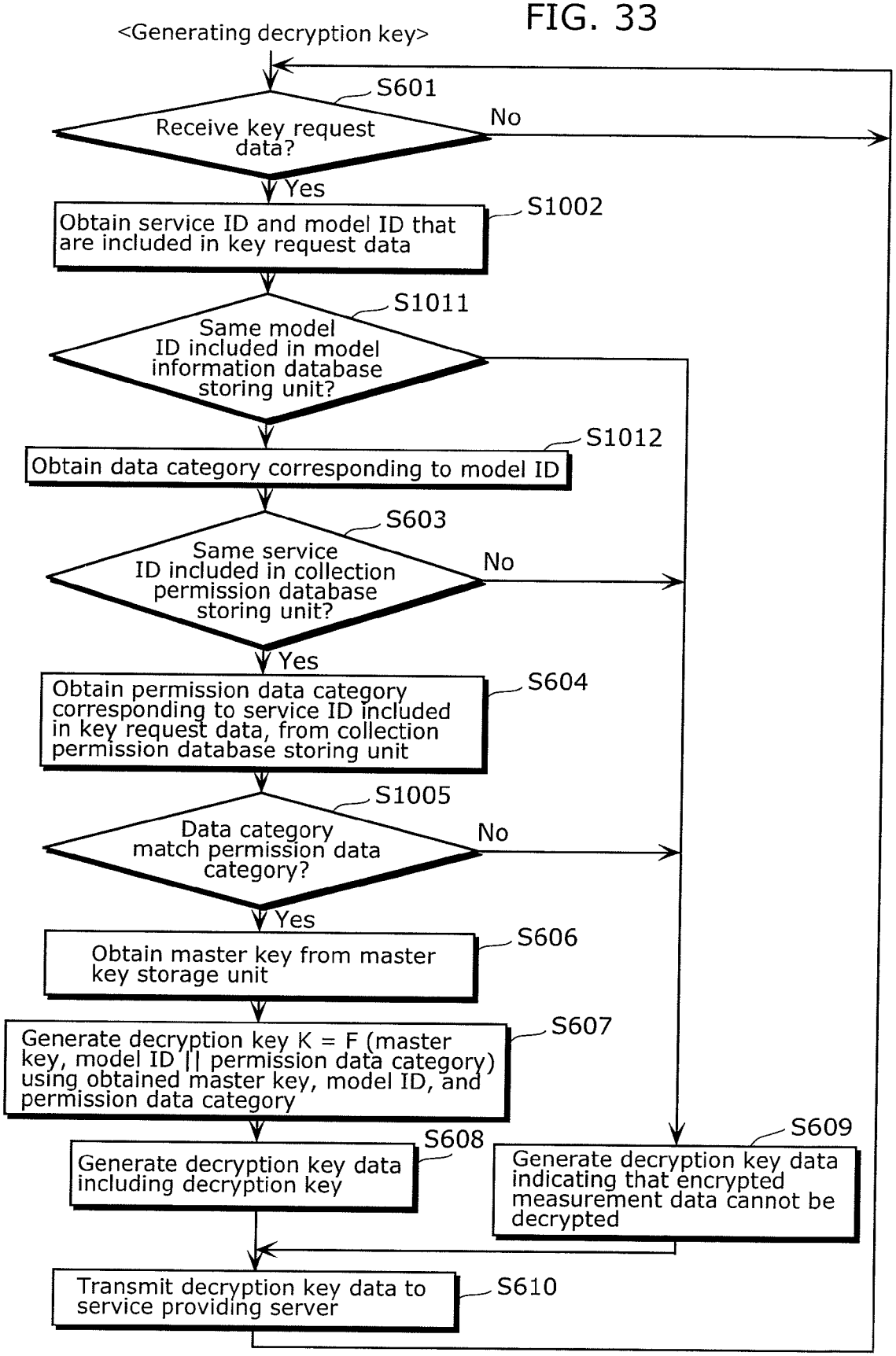
FIG. 33 shows a flowchart indicating generating of a decryption key by the key management server according to the second embodiment.

FIG. 33 shows a flowchart indicating generating of a decryption key by the key management server 16.

First, the transmitting and receiving unit 161 judges whether or not the key management server 16 has received the key request data 77 from a service providing server through the external network 15 (Step S601). Here, when the key management server 16 has not received the key request data 77 (No in Step S601), again, the transmitting and receiving unit 161 judges whether or not the key management server 16 has received the key request data 77 (Step S601). On the other hand, when the key management server 16 has received the key request data 77 (Yes in Step S601), the decryption key generation-permission judging unit 163 obtains a service ID and a model ID that are included in the key request data 77 (Step S1002).

Next, the decryption key generation-permission judging unit 163 judges whether or not the model ID included in the key request data 77 is included in the model information database 80 stored in the model information database storing unit 165 (Step S1011). Here, when the model ID is not included in the model information database 80 (No in Step S1011), the decryption key generating unit 162 generates decryption key data indicating that a service providing server that has transmitted the key request data 77 cannot decrypt encrypted measurement data (Step S609). Here, when the model ID is included in the model information database 80 (Yes in Step S1011), the decryption key generation-permission judging unit 163 obtains, from the model information database 80, a data category corresponding to a service ID included in the key request data 77 (Step S1012).

Next, the decryption key generation-permission judging unit 163 judges whether or not the service ID included in the key request data 77 is also included in the collection permission database 29 stored in the collection permission database storing unit 164 (Step S603). Here, when the service ID is not included in the collection permission database 29 (No in Step S603), the decryption key generating unit 162 generates decryption key data indicating that a service providing server that has transmitted the key request data 77 cannot decrypt encrypted measurement data (cannot decrypt) (Step S609). On the other hand, when the service ID is included in the collection permission database 29 (Yes in Step S603), the decryption key generating unit 163 obtains, from the collection permission database 29, a permission data category corresponding to the service ID included in the key request data 77 (Step S604).

Next, the decryption key generating unit 163 judges whether or not the data category obtained from the model information database 80 in Step S1012 matches the permission data category obtained from the collection permission database 29 in Step S604 (Step S1005). Here, when the data category does not match the permission data category (No in Step S1005), the decryption key generating unit 162 generates decryption key data indicating that a service providing server that has transmitted the key request data 77 cannot decrypt encrypted measurement data (cannot decrypt) (Step S609). On the other hand, when the data category matches the permission data category (Yes in Step S1005), the decryption key generating unit 162 obtains a master key stored in the master key storage unit 160 (Step S606).

The key management server 16 performs the processes in Steps S607 to 610 as in the first embodiment.

As described above, the health care system 1 of the second embodiment can eliminate, in a measuring apparatus, encryption processing for encrypting measurement data using different encryption keys according to a category of each server that provides a service as in the first embodiment.

Furthermore, when the key management server 16 receives key request data 77 from a service providing server (for example, the first service providing server 17a), the key management server 16 according to the second embodiment identifies a data category using the model ID included in the key request data 77. Then, the key management server 16 judges whether or not the identified data category and the service ID included in the key request data 77 match the data category and the service ID that are stored in the collection permission database storing unit 164 and are included in the collection permission database 29. When they match each other, the key management server 16 transmits a decryption key to the corresponding service providing server. Thereby, since the key management server 16 can limit the data categories included in the key request data 77 received from a service providing server to two categories, a model ID and a service ID, an processing amount for the judgment can be reduced.

Third Embodiment

Next, a health care system according to a third embodiment with reference to drawings will be described.

The health care system 1 according to the third embodiment employs a public key cryptography that differs from a symmetric key cryptography in the first embodiment. Hereinafter, such differences will be mainly described in the third embodiment by omitting points similar to the illustration and description used in the first embodiment.

Since the functional configurations of the health care system 1, the measuring apparatus 10a, the user-terminal card 14, the first service providing server 17a are the same as those of the first embodiment, the illustration and description are also omitted.

<Configurations of Measuring-Apparatus Cards 11a, 11b, and 11c>

The measuring-apparatus card 11a of the third embodiment differs from the measuring-apparatus card 11a of the first embodiment in including an encryption key information storage unit 117 instead of the master key storage unit 112.

Figure 34:
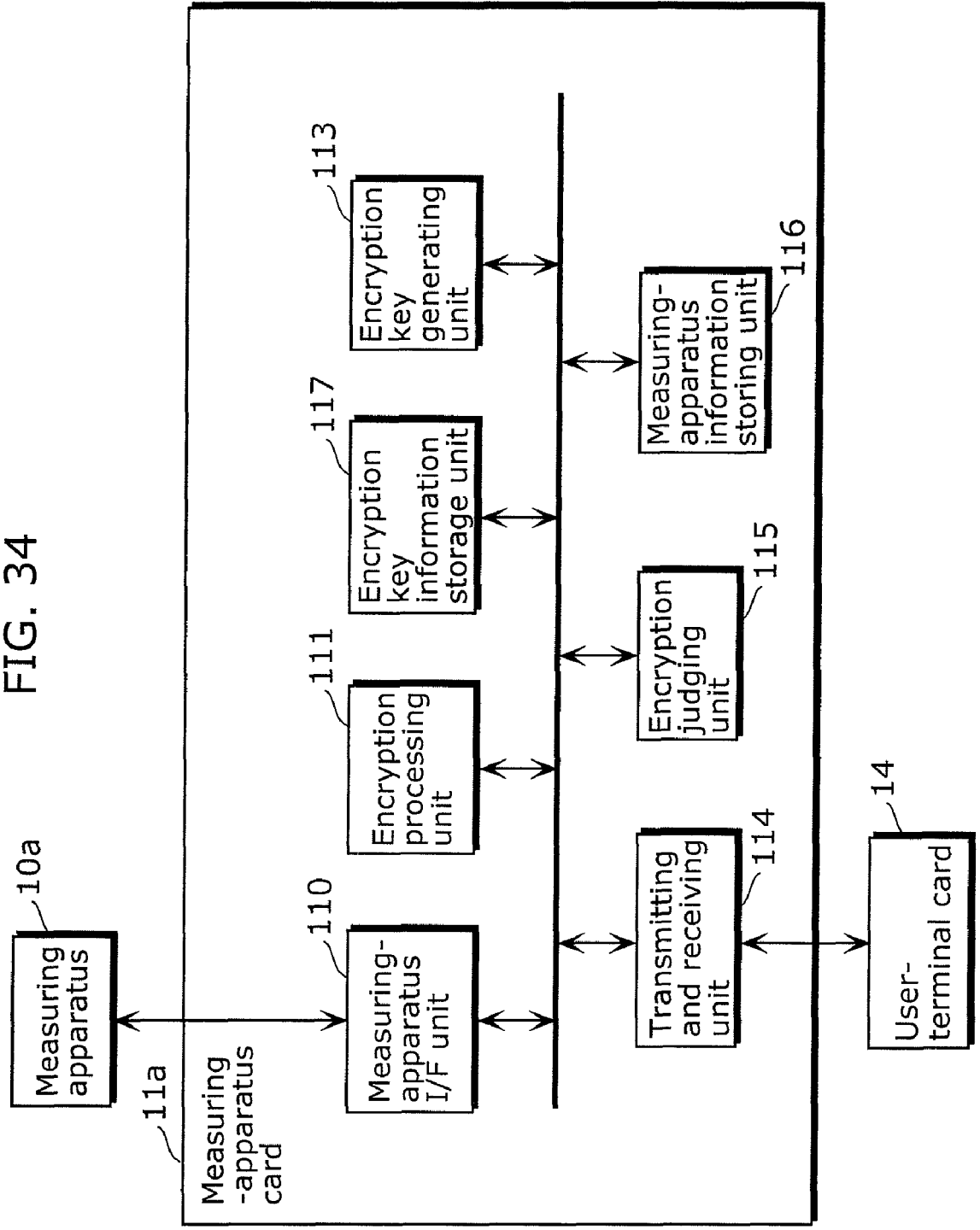
FIG. 34 schematically illustrates a functional configuration of the measuring-apparatus card according to the third embodiment.

FIG. 34 schematically illustrates a functional configuration of the measuring-apparatus card 11a.

(Encryption Key Information Storage Unit 117)

The encryption key information storage unit 117 stores encryption key information for use in generating a public key as an encryption key.

(Encryption Key Generating Unit 113)

The encryption key generating unit 113 is an example of an encryption key generating unit, and generates a public key based on encryption key information, a model ID, and a data category. Known methods in a public key cryptography based on IDs are used for generating a public key. Although the third embodiment describes that the encryption key generating unit 113 generates an encryption key, based on encryption key information, a model ID, and a data category, the health care system 1 according to the present invention is not limited to such a health care system. The health care system 1 according to the present invention may be, for example, a health care system in which the encryption key generating unit generates an encryption key based on encryption key information and a model ID.

<Configuration of Key Management Server 16>

The key management server 16 of the third embodiment differs from the key management server 16 of the first embodiment in including a decryption key information storage unit 166 instead of the master key storage unit 160.

Figure 35:
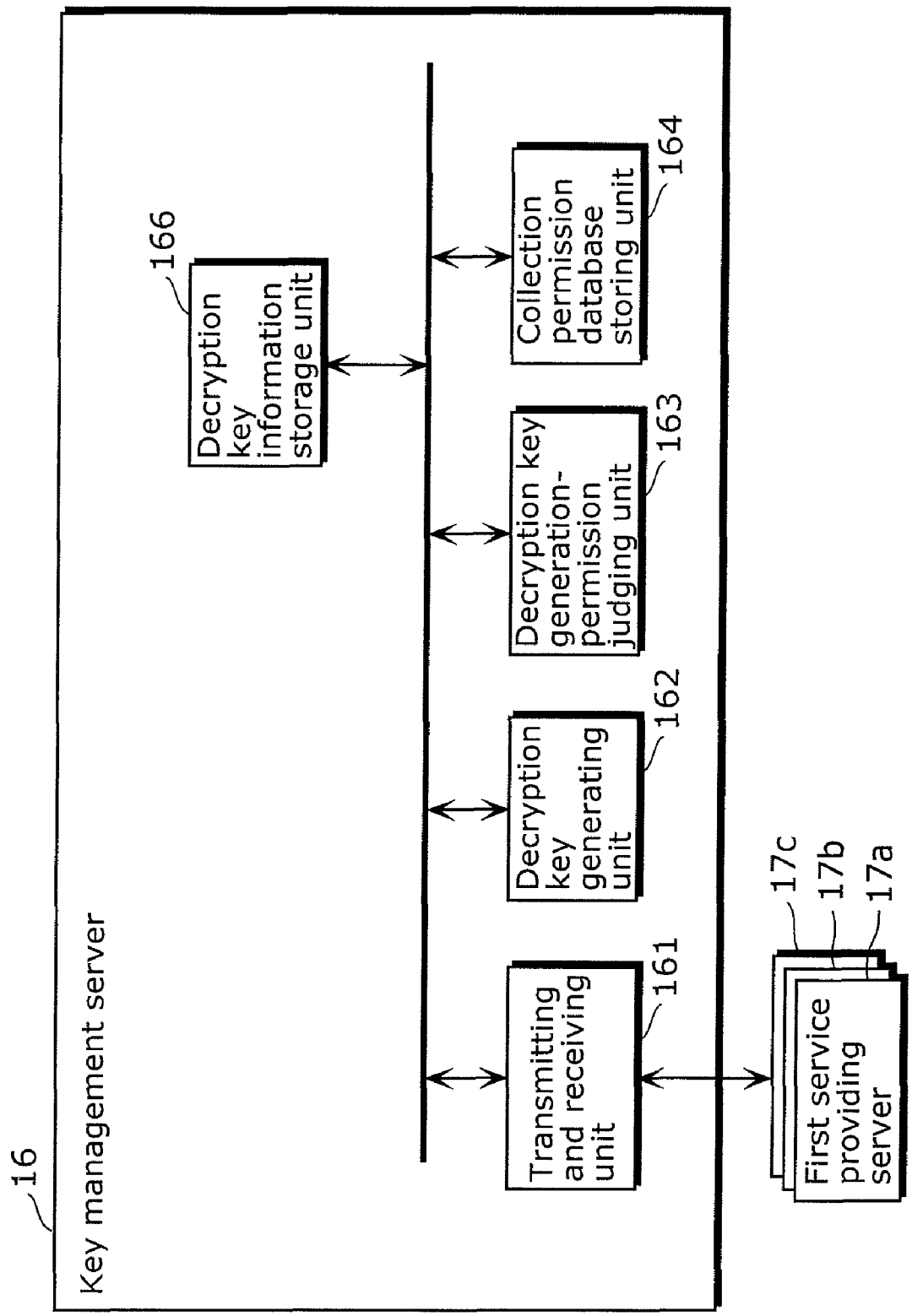
FIG. 35 illustrates a block diagram of a functional configuration of the key management server according to the third embodiment.

FIG. 35 schematically illustrates a functional configuration of the key management server 16.

(Decryption Key Information Storage Unit 166)

Decryption key information for generating a decryption key is stored in the decryption key information storage unit 166 that is an example of a master information storage unit.

(Decryption Key Generating Unit 162)

The decryption key generating unit 162 is an example of a key generating unit, and generates a secret key corresponding to a public key generated by the measuring-apparatus card 11a, based on decryption key information stored in the decryption key information storage unit 166 and a model ID and a data category included in the key request data 27, in response to a request from a service providing server. Known methods in a public key cryptography based on IDs are used for generating a public key. Here, the decryption key generating unit 162 may generate a decryption key based on decryption key information and a model ID, as the encryption key generating unit 113 included in a measuring-apparatus card.

Next, various operations of the health care system 1 having the aforementioned configuration according to the third embodiment will be described.

Detailed operations of the measuring-apparatus card 11a and key management server 16 will be described. Since the operations of the measuring apparatus 10a, the user-terminal card 14, and the first service providing server 17a in the third embodiment are the same as those of the first embodiment, the illustration and description are omitted. Furthermore, steps in flowcharts of the third embodiment are similarly numbered as those of the first embodiment, and the description is omitted.

<Encrypting and Transmitting of Measurement Data Using Measuring-Apparatus Card 11a>

Processing of the measuring-apparatus card 11a that encrypts measurement data obtained by the measuring apparatus 10a and transmits the encrypted measurement data will be described.

Figure 36:
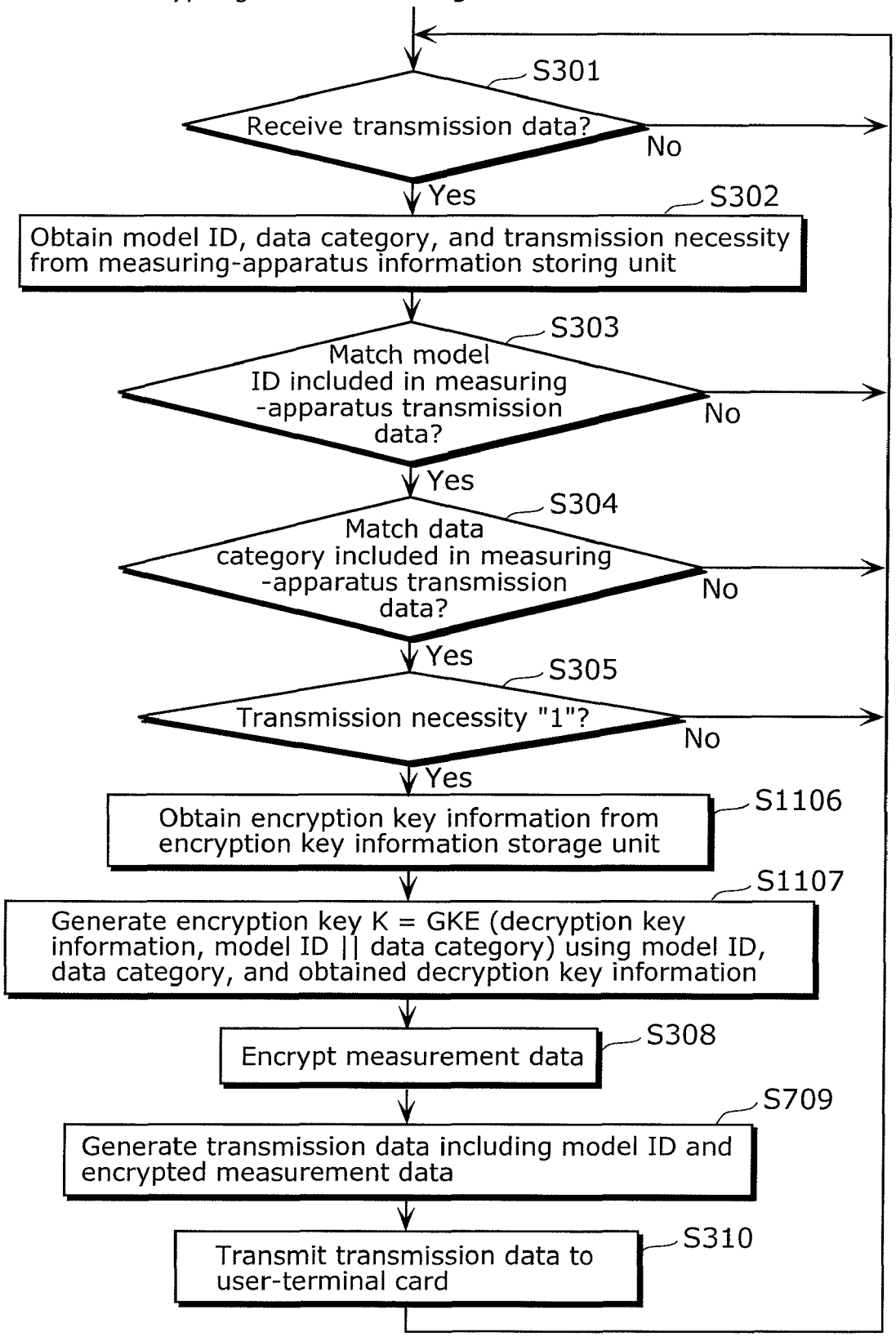
FIG. 36 shows a flowchart indicating encrypting and transmitting measurement data using the measuring-apparatus card according to the third embodiment.

FIG. 36 shows a flowchart indicating the encrypting and transmitting of measurement data using the measuring-apparatus card 11a.

The measuring-apparatus card 11a performs the processes in Step S301 to S305 in the same manner as the measuring-apparatus card 11a of the first embodiment. Then, the encryption key generating unit 113 obtains the encryption key information stored in the encryption key information storage unit 117 (Step S1106).

Next, the encryption key generating unit 113 generates an encryption key using a model ID, a data category, and the obtained encryption key information (Step S1107).

The measuring-apparatus card 11a performs the processes in Step S308 to S310 in the same manner as the measuring-apparatus card 11a of the first embodiment.

<Generating Decryption Key by Key Management Server 16>

Next, generating a decryption key by the key management server 16 using the received key request data 27 will be described.

Figure 37:
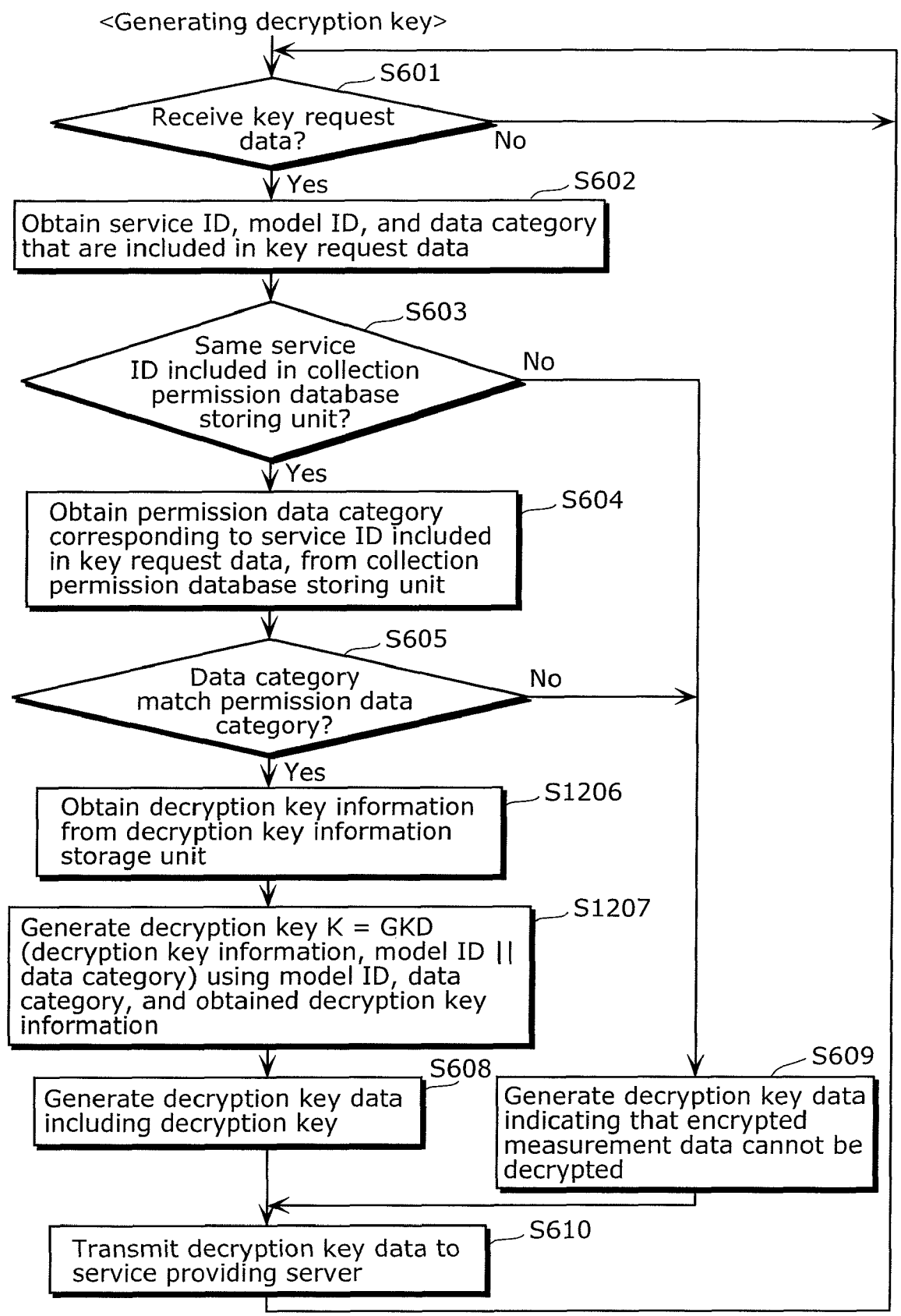
FIG. 37 shows a flowchart indicating generating of a decryption key by the key management server according to the third embodiment.

FIG. 37 shows a flowchart indicating generating of a decryption key by the key management server 16.

The key management server 16 performs the processes in Steps S601 to 605 as in the first embodiment. Then, the decryption key generating unit 162 obtains decryption key information stored in the decryption key information storage unit 166 (Step S1206).

Next, the decryption key generating unit 162 generates a decryption key using the obtained decryption key information, the model ID, and the data category, as a secret key corresponding to the public key generated by the measuring-apparatus card 11a (Step S1207).

The key management server 16 performs the processes in Steps S608 to 610 as in the first embodiment.

As described above, the health care system 1 of the third embodiment can eliminate, in a measuring apparatus, encryption processing for encrypting measurement data using different encryption keys according to a category of each server that provides a service as in the first embodiment.

Furthermore, according to the health care system 1 of the third embodiment, a measuring-apparatus card (for example, the measuring-apparatus card 11a) generates, as a public key, an encryption key for use in encrypting measurement data using a model ID. In other words, the measuring apparatus or the measuring-apparatus card does not have to store any master key. Thus, the health care system 1 of the third embodiment can prevent confidentiality of measurement data from being impaired through analysis on the measuring apparatus or the measuring-apparatus card and disclosure of a master key. Furthermore, a measuring apparatus or a measuring-apparatus card generates a public key using a model ID that is information identifying a measuring apparatus. As long as the key management server 16 holds master information for generating a decryption key, the encrypted measurement data is never decrypted even when the model ID is leaked outside. In other words, the health care system 1 of the third embodiment can ensure confidentiality of measurement data.

(Other Variations)

The present invention is not limited to the aforementioned embodiments obviously. The present invention also include following variations.

(1) A size of each data described above is one of the examples, and other sizes may also be used.

(2) Although data is encrypted in cards, such as a measuring-apparatus card and a user-terminal card, these cards may be integrated into a measuring apparatus or a user terminal. Furthermore, the measuring-apparatus card and the user-terminal card may be memory cards attached to the measuring apparatus and the user terminal.

(3) Although the measuring-apparatus card transmits measurement data that has been encrypted to a user-terminal card immediately soon after the encryption, the measuring-apparatus card may temporarily store the measurement data encrypted and transmit the measurement data to the user-terminal card for each predetermined period.

(4) The measuring-apparatus card generates an encryption key using a model ID, a data category, and a master key each time the measuring-apparatus card encrypts measurement data. When the encryption key generated is temporarily stored in a cache and again measurement data having the same data category is transmitted from the measuring apparatus having the same model ID, the measurement data may be encrypted using the encryption key stored in the cache.

(5) The communication data between a user-terminal card and a service providing server and between the service providing server and a key management server may be encrypted using the Secure Socket Layer (SSL).

(6) A measuring-apparatus card and a user-terminal card carry out not only wireless communication but also wire communication.

(7) Whether or not data is decrypted may be judged not only on a category of health information basis but also on a smaller data unit basis. For example, in addition to a category of health information, whether or not data is decrypted may be judged based on a period of time during which the health information has been obtained through measurement (by setting values, such as 1=indefinite period, 2=2007/10/1 to 2008/3/30, or such as 1=12:00 midnight to 5:00 a.m., 2=6:00 to 11:00 a.m., 3=12:00 noon to 5:00 p.m., 4=6:00 p.m. to 12:00 midnight). Such judgment becomes possible by including a timer or a calendar in a measuring apparatus. Furthermore, the measuring apparatus may control accessing information, depending on registered information of an owner of the measuring apparatus (name, nickname, age, generation, gender, zip code, address). Such access control becomes possible as long as the measuring apparatus has a function for registering owner information.

(8) The apparatus information to be transmitted together with encrypted measurement data may be encrypted or provided with a digital signature. Such processing may be performed by the measuring apparatus or by the management apparatus.

(9) The master key is not limited to one. For example, even when a different master key is set for each manufacturer of a card, the master key of the present invention can be achieved by transmitting a manufacturer ID together with encrypted measurement data.

(10) Each of the above apparatuses is specifically a computer system including a micro processing unit, a ROM, a RAM, a hard disk unit, a display unit, a keyboard, a mouse, and the like. A computer program is stored in the RAM or the hard disk unit. The micro processing unit operates according to the computer program, so that each of the apparatuses fulfills a function. Here, in order to fulfill predetermined functions, the computer program is programmed by combining plural instruction codes each of which indicates an instruction for a computer.

(11) Part or all of the components included in each of the above apparatuses may be included in one system large scale integration (LSI). The system LSI is a super-multifunctional LSI manufactured by integrating components on one chip and is, specifically, a computer system including a micro processing unit, a ROM, a RAM, and the like. The computer program is stored in the RAM. The micro processing unit operates according to the computer program, so that the system LSI fulfills its function.

(12) Part or all of the components included in each of the above apparatuses may be included in an IC card removable from each of the apparatuses or in a stand alone module. The IC card or the module is a computer system including a micro processing unit, a ROM, a RAM, and the like. The IC card or the module may include the above super-multifunctional LSI. The micro processing unit operates according to the computer program, so that the IC card or the module fulfills its function. The IC card or the module may have tamper-resistance.

(13) The present invention may be any of the above methods. Furthermore, the present invention may be a computer program which causes a computer to execute these methods, and a digital signal which is composed of the computer program.

Moreover, in the present invention, the computer program or the digital signal may be recorded on a computer-readable recording medium such as a flexible disk, a hard disk, a CD-ROM, an MO, a DVD, a DVD-ROM, a DVD-RAM, a Blu-ray Disc (BD), and a semiconductor memory. In addition, the digital signal may be recorded on these recording media.

Furthermore, in the present invention, the computer program or the digital signal may be transmitted via an electronic communication line, a wireless or wired communication line, a network represented by the Internet, data broadcasting, and the like.

Moreover, the present invention may be a computer system including a micro processing unit and a memory. The memory may store the above computer program, and the micro processing unit may operate according to the computer program.

Furthermore, the present invention may execute the computer program or the digital signal in another independent computer system by recording the computer program or the digital signal on the recording medium and transmitting the recorded computer program or digital signal, or by transmitting the computer program or the digital signal via the network and the like.

(14) The above embodiments and the above modifications may be combined respectively.

Although only some exemplary embodiments of this invention have been described in detail above, those skilled in the art will readily appreciate that many modifications are possible in the exemplary embodiments without materially departing from the novel teachings and advantages of this invention. Accordingly, all such modifications are intended to be included within the scope of this invention.

INDUSTRIAL APPLICABILITY

The health care system according to the present invention does not increase encryption processing in a measuring apparatus even when the number of services to be used by the user increases. Thus, when the measuring apparatus is a portable terminal that has constraints in its processing load, such health care system is useful.

What is claimed is:

1. A health care system, comprising:
a measuring apparatus that obtains vital sign data through measurement and encrypts the obtained vital sign data;
a server that obtains the encrypted vital sign data from said measuring apparatus and provides a service related to health; and
a key management server that provides a decryption key for decrypting the encrypted vital sign data to said server,
wherein said measuring apparatus includes:
a measuring unit configured to obtain the vital sign data of a user of said measuring apparatus through measurement of the user of said measuring apparatus;
a first storing unit configured to store first identification information identifying said measuring apparatus;
a first key generating unit configured to generate an encryption key using the first identification information;
an encrypting unit configured to encrypt the obtained vital sign data using the encryption key to generate the encrypted vital sign data; and
a first communicating unit configured to transmit, to said server, the first identification information, second identification information, and the encrypted vital sign data, the second identification information identifying a category of the vital sign data, said server includes:

a second storing unit configured to store the first identification information, the second identification information, and the encrypted vital sign data transmitted by said first communicating unit;

a third storing unit configured to store third identification information identifying said server; and a second communicating unit configured to transmit, to said key management server, a request for transmitting to said server a decryption key corresponding to the encryption key, together with the first identification information, the second identification information, and the third identification information, and said key management server includes:

a second key generating unit configured to generate the decryption key corresponding to the encryption key using the first identification information;

a fourth storing unit configured to store fourth identification information identifying a server predetermined as a destination of the decryption key, and fifth identification information indicating the category of the vital sign data in correspondence with the fourth identification information; and a control unit configured to transmit the decryption key to said server, upon receipt of the request for transmitting the decryption key from said server, together with the first identification information, the second identification information, and the third identification information, when the received third identification information matches the stored fourth identification information and the received second identification information matches the fifth identification information stored in said fourth storing unit in correspondence with the matched fourth identification information, wherein said server decrypts the encrypted vital sign data using the decryption key.

2. A health care system, comprising:

a measuring apparatus that obtains vital sign data through measurement and encrypts the obtained vital sign data;

a server that obtains the encrypted vital sign data from said measuring apparatus and provides a service related to health; and a key management server that provides a decryption key for decrypting the encrypted vital sign data to said server, wherein said measuring apparatus includes:

a measuring unit configured to obtain the vital sign data of a user of said measuring apparatus through measurement of the user of said measuring apparatus;

a first storing unit configured to store first identification information identifying said measuring apparatus;

a first key generating unit configured to generate an encryption key using the first identification information;

an encrypting unit configured to encrypt the obtained vital sign data using the encryption key to generate the encrypted vital sign data; and a first communicating unit configured to transmit, to said server, the first identification information and the encrypted vital sign data, said server includes:

a second storing unit configured to store the first identification information and the encrypted vital sign data transmitted by said first communicating unit;

a third storing unit configured to store second identification information identifying said server; and a second communicating unit configured to transmit, to said key management server, a request for transmitting to said server the decryption key corresponding to the encryption key, together with the first identification information and the second identification information, and said key management server includes:

a fourth storing unit in which a category of the vital sign data obtained by said measuring apparatus is stored in correspondence with the first identification information;

a fifth storing unit configured to store a category of the vital sign data managed by said server in correspondence with the second identification information;

a second key generating unit configured to generate the decryption key corresponding to the encryption key using the first identification information; and a control unit configured to transmit the decryption key to said server, upon receipt of, from said server, the request for transmitting the decryption key to said server, together with the first identification information and the second identification information, when the category of vital sign data that is stored in said fourth storing unit and corresponds to the received first identification information matches the category of vital sign data that is stored in said fifth storing unit and corresponds to the received second identification information, wherein said server decrypts the encrypted vital sign data using the decryption key.

3. The health care system according to claim 1, wherein said measuring apparatus includes an encrypting device, and said encrypting device includes said first key generating unit, said encrypting unit, and said first communicating unit.

4. The health care system according to claim 3, wherein said encrypting device is a memory card attached to said measuring apparatus.

5. The health care system according to claim 1, wherein said measuring apparatus further includes a first master key holding unit configured to hold a first master key, said first key generating unit is configured to generate the encryption key using the first identification information and the first master key, said key management server includes a second master key holding unit configured to hold a second master key identical to the first master key, and said second key generating unit is configured to generate the decryption key corresponding to the encryption key, using the first identification information and the second master key.

6. The health care system according to claim 5, wherein said measuring apparatus includes an encrypting device, said encrypting device includes said first key generating unit, said encrypting unit, said first master key holding unit, and said first communicating unit, and said first key generating unit is configured to generate the encryption key using the first identification information and the master key.

7. The health care system according to claim 6, wherein said encrypting device is a memory card attached to said measuring apparatus.

8. The health care system according to claim 1, wherein said first key generating unit is configured to generate the encryption key using the first identification information as a public key, said key management server includes
a master information holding unit configured to hold master information for generating the decryption key, and
said second key generating unit is configured to generate the decryption key as a secret key corresponding to the public key, using the received first identification information and the held master information.

9. The health care system according to claim 2,
wherein said measuring apparatus includes an encrypting device, and
said encrypting device includes said first key generating unit, said encrypting unit, and said first communicating unit.

10. The health care system according to claim 9,
wherein said encrypting device is a memory card attached to said measuring apparatus.

11. The health care system according to claim 2,
wherein said measuring apparatus further includes
a first master key holding unit configured to hold a first master key,
said first key generating unit is configured to generate the encryption key using the first identification information and the first master key,
said key management server includes
a second master key holding unit configured to hold a second master key identical to the first master key, and
said second key generating unit is configured to generate the decryption key corresponding to the encryption key, using the first identification information and the second master key.

12. The health care system according to claim 11,
wherein said measuring apparatus includes an encrypting device,
said encrypting device includes said first key generating unit, said encrypting unit, said first master key holding unit, and said first communicating unit, and
said first key generating unit is configured to generate the encryption key using the first identification information and the master key.

13. The health care system according to claim 12,
wherein said encrypting device is a memory card attached to said measuring apparatus.

14. The health care system according to claim 2,
wherein said first key generating unit is configured to generate the encryption key using the first identification information as a public key,
said key management server includes
a master information holding unit configured to hold master information for generating the decryption key, and
said second key generating unit is configured to generate the decryption key as a secret key corresponding to the public key, using the received first identification information and the held master information.

15. A method for managing a key in a health care system, the health care system including a measuring apparatus, a server, and a key management server, the measuring apparatus obtaining vital sign data through measurement and encrypting the obtained vital sign data, the server obtaining the encrypted vital sign data from the measuring apparatus and provides a service related to health, the key management server transmitting to the server a decryption key for decrypting the encrypted vital sign data, the method comprising:
obtaining at the measuring apparatus the vital sign data of a user of the measuring apparatus through measurement of the user of the measuring apparatus;
generating at the measuring apparatus an encryption key using first identification information identifying the measuring apparatus;
encrypting at the measuring apparatus the obtained vital sign data using the encryption key to generate the encrypted vital sign data; and
transmitting, from the measuring apparatus to the server, the first identification information, second identification information, and the encrypted vital sign data, the second identification information identifying a category of the vital sign data;
storing at the server the first identification information, the second identification information, and the encrypted vital sign data transmitted from the measuring apparatus; and
transmitting, from the server to the key management server, a request for transmitting to the server the decryption key corresponding to the encryption key, together with the first identification information, the second identification information, and third identification information identifying the server; and
transmitting, from the key management server to the server, the decryption key to the server, upon receipt of the request for transmitting the decryption key from the server, together with the first identification information, the second identification information, and the third identification information, when the received third identification information matches fourth identification information and the received second identification information matches fifth identification information, the fourth identification information identifying a server predetermined as a destination of the decryption key, and the fifth identification information indicating the category of the vital sign data managed by the server and being stored in correspondence with the matched fourth identification information,
wherein the server decrypts the encrypted vital sign data using the decryption key.

16. A method for managing information in a health care system, the health care system including a measuring apparatus, a server, and a key management server, the measuring apparatus obtaining vital sign data of a user of the measuring apparatus through measurement of the user of the measuring apparatus and encrypting the obtained vital sign data, the server obtaining the encrypted vital sign data from the measuring apparatus and providing a service related to health, the key management server transmitting to the server a decryption key for decrypting the encrypted vital sign data, the method comprising:
obtaining at the measuring apparatus the vital sign data through measurement;
generating at the measuring apparatus an encryption key using first identification information identifying the measuring apparatus; and
encrypting at the measuring apparatus the obtained vital sign data using the encryption key to generate the encrypted vital sign data;
receiving, at the server from the measuring apparatus, the first identification information and the encrypted vital sign data; and
transmitting, from the server to the key management server, a request for transmitting to the server the decryption key corresponding to the encryption key, together with the first identification information and second identification information identifying the server; and transmitting, from the key management server to the server, the decryption key, upon receipt of, from the server, the request for transmitting the decryption key to the server together with the first identification information and the second identification information, when a category of the vital sign data stored in correspondence with the received first identification information matches a category of the service stored in correspondence with the received second identification information, wherein the server decrypts the encrypted vital sign data using the decryption key.

* * * * *

UNITED STATES PATENT AND TRADEMARK OFFICE
CERTIFICATE OF CORRECTION

| | | |
|---|---|---|
| PATENT NO. | : 7,774,852 B2 | Page 1 of 1 |
| APPLICATION NO. | : 12/249185 | |
| DATED | : August 10, 2010 | |
| INVENTOR(S) | : Kaoru Yokota et al. | |

It is certified that error appears in the above-identified patent and that said Letters Patent is hereby corrected as shown below:

ON THE COVER PAGE

Please insert in section (30) Foreign Application Priority Data

-- Oct. 12, 2007 (JP) ............................... 2007-266742
   Aug. 28, 2008 (JP) ............................... 2008-220207 --

Signed and Sealed this
Eighteenth Day of January, 2011

David J. Kappos
*Director of the United States Patent and Trademark Office*